(12) United States Patent
Li et al.

(10) Patent No.: US 11,291,720 B2
(45) Date of Patent: *Apr. 5, 2022

(54) ANTI-CTLA4 MONOCLONAL ANTIBODY OR ITS ANTIGEN BINDING FRAGMENTS, PHARMACEUTICAL COMPOSITIONS AND USES

(71) Applicant: AKESO BIOPHARMA, INC., Guangdong (CN)

(72) Inventors: Baiyong Li, Guangdong (CN); Yu Xia, Guangdong (CN); Zhongmin Wang, Guangdong (CN); Peng Zhang, Guangdong (CN); Xinghua Pang, Guangdong (CN)

(73) Assignee: AKESO BIOPHARMA, INC., Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/562,236

(22) Filed: Sep. 5, 2019

(65) Prior Publication Data

US 2020/0206346 A1    Jul. 2, 2020

Related U.S. Application Data

(63) Continuation of application No. 15/500,744, filed as application No. PCT/CN2015/085721 on Jul. 31, 2015, now Pat. No. 10,449,251.

(30) Foreign Application Priority Data

Aug. 1, 2014 (CN) .......................... 201410377352.9

(51) Int. Cl.
| | |
|---|---|
| *A61K 39/395* | (2006.01) |
| *C12N 15/63* | (2006.01) |
| *C12N 5/10* | (2006.01) |
| *C07K 19/00* | (2006.01) |
| *C07K 16/28* | (2006.01) |
| *G01N 33/577* | (2006.01) |
| *A61K 49/00* | (2006.01) |

(52) U.S. Cl.
CPC ...... *A61K 39/39541* (2013.01); *A61K 39/395* (2013.01); *C07K 16/28* (2013.01); *C07K 16/2896* (2013.01); *C07K 19/00* (2013.01); *C12N 5/10* (2013.01); *C12N 15/63* (2013.01); *G01N 33/577* (2013.01)

(58) Field of Classification Search
USPC ............ 424/9.1, 9.2, 130.1, 141.1; 536/23.1, 536/23.53
See application file for complete search history.

(56) References Cited

U.S. PATENT DOCUMENTS

| | | | |
|---|---|---|---|
| 4,816,567 A | 3/1989 | Cabilly et al. | |
| 5,811,097 A | 9/1998 | Allison et al. | |
| 5,855,887 A | 1/1999 | Allison et al. | |
| 5,977,318 A | 11/1999 | Linsley et al. | |
| 6,051,227 A | 4/2000 | Allison et al. | |
| 6,682,736 B1 | 1/2004 | Hanson et al. | |
| 6,984,720 B1 | 1/2006 | Korman et al. | |
| 7,109,003 B2 | 9/2006 | Hanson et al. | |
| 7,132,281 B2 | 11/2006 | Hanson et al. | |
| 7,411,057 B2 | 8/2008 | Hanson et al. | |
| 7,452,535 B2 | 11/2008 | Davis et al. | |
| 7,465,446 B2 | 12/2008 | Lowy et al. | |
| 7,595,048 B2 | 9/2009 | Honjo et al. | |
| 7,605,238 B2 | 10/2009 | Korman et al. | |
| 7,744,875 B2 | 6/2010 | Lowy et al. | |
| 7,807,797 B2 | 10/2010 | Hanson et al. | |
| 7,824,679 B2 | 11/2010 | Hanson et al. | |
| 8,008,449 B2 | 8/2011 | Korman et al. | |
| 8,017,714 B2 | 9/2011 | Uhrich | |
| 8,129,508 B2 | 3/2012 | Arunakumari et al. | |
| 8,142,778 B2 | 3/2012 | Davis et al. | |
| 8,143,379 B2 | 3/2012 | Hanson et al. | |
| 8,168,170 B2 | 5/2012 | Myatt | |
| 8,263,073 B2 | 9/2012 | Korman et al. | |
| 8,318,916 B2 | 11/2012 | Korman et al. | |
| 8,435,516 B2 | 5/2013 | Huang et al. | |
| 8,491,895 B2 | 7/2013 | Hanson et al. | |
| 8,697,847 B2 | 4/2014 | Arunakumari et al. | |
| 8,728,474 B2 | 5/2014 | Honjo et al. | |
| 8,765,415 B2 | 7/2014 | Arunakumari et al. | |

(Continued)

FOREIGN PATENT DOCUMENTS

| | | |
|---|---|---|
| CN | 1328571 A | 12/2001 |
| CN | 101074264 A | 11/2007 |

(Continued)

OTHER PUBLICATIONS

Office Action dated Dec. 17, 2019 in corresponding CA Appl. No. 2,956,000.
Office Action dated Mar. 10, 2020 in corresponding SA Appl. No. 517380820.
Office Action dated Apr. 2, 2019 in corresponding NZ Appl. No. 729158.
Office Action dated Oct. 11, 2019 in corresponding NZ Appl. No. 729158.
Office Action dated Sep. 13, 2019 in corresponding EA Appl. No. 201790288.
Office Action dated Nov. 13, 2019 in corresponding IN Appl. No. 201747003171.
Office Action dated Jan. 21, 2020 in corresponding JP Appl. No. 2019-036646.
Alfthan et al., "Properties of a single-chain antibody containing different linker peptides", Protein Eng. 8:725-731 (1995).

(Continued)

*Primary Examiner* — Gary B Nickol
*Assistant Examiner* — Jegatheesan Seharaseyon
(74) *Attorney, Agent, or Firm* — Faegre Drinker Biddle & Reath LLP

(57) ABSTRACT

The present invention belongs to the fields of tumor therapy and molecular immunology, and provides an anti-CTLA4 monoclonal antibody or antigen binding fragment thereof, a pharmaceutical composition thereof and use thereof. The monoclonal antibody of the present invention can block the binding of CLTA4 to B7, relieve the immunosuppression on the body by CTLA4, and activate T lymphocytes.

35 Claims, 12 Drawing Sheets

Specification includes a Sequence Listing.

(56) References Cited

U.S. PATENT DOCUMENTS

| | | | |
|---|---|---|---|
| 8,779,105 B2 | 7/2014 | Korman et al. | |
| 8,784,815 B2 | 7/2014 | Korman et al. | |
| 8,883,984 B2 | 11/2014 | Hanson et al. | |
| 9,067,999 B1 | 6/2015 | Honjo et al. | |
| 9,073,994 B2 | 7/2015 | Honjo et al. | |
| 9,084,776 B2 | 7/2015 | Korman et al. | |
| 9,119,839 B2 | 9/2015 | Huang et al. | |
| 9,212,224 B2 | 12/2015 | Cogswell et al. | |
| 9,358,289 B2 | 6/2016 | Korman et al. | |
| 9,387,247 B2 | 7/2016 | Korman et al. | |
| 9,393,301 B2 | 7/2016 | Honjo et al. | |
| 9,402,899 B2 | 8/2016 | Honjo et al. | |
| 9,492,539 B2 | 11/2016 | Korman et al. | |
| 9,492,540 B2 | 11/2016 | Korman et al. | |
| 9,714,290 B2 | 7/2017 | Jones et al. | |
| 9,856,320 B2 | 1/2018 | Cogswell et al. | |
| 9,963,508 B2 | 5/2018 | Hanson et al. | |
| 10,030,064 B2 | 7/2018 | Jing et al. | |
| 10,072,082 B2 | 9/2018 | Cogswell et al. | |
| 10,449,251 B2 * | 10/2019 | Li | C07K 16/28 |
| 2003/0086930 A1 | 5/2003 | Mueller et al. | |
| 2005/0042223 A1 | 2/2005 | Lee et al. | |
| 2014/0234331 A1 | 8/2014 | Korman et al. | |
| 2014/0245692 A1 | 9/2014 | Bowers et al. | |
| 2014/0302581 A1 | 10/2014 | Arunakumari et al. | |
| 2015/0079100 A1 | 3/2015 | Roy et al. | |
| 2015/0156025 A1 | 6/2015 | Zhu et al. | |
| 2016/0000863 A1 | 1/2016 | Rodríguez Fernández-Alba et al. | |
| 2016/0158356 A1 | 6/2016 | Honjo et al. | |
| 2016/0222121 A1 | 8/2016 | Johnson et al. | |
| 2016/0257753 A1 | 9/2016 | Korman et al. | |
| 2017/0088615 A1 | 3/2017 | Korman et al. | |
| 2017/0088626 A1 | 3/2017 | Jure-Kunkel et al. | |
| 2017/0158776 A1 | 6/2017 | Feltquate et al. | |

FOREIGN PATENT DOCUMENTS

| | | |
|---|---|---|
| CN | 103221544 A | 7/2013 |
| CN | 103547595 A | 1/2014 |
| CN | 104479019 A | 4/2015 |
| EP | 0865293 A1 | 9/1998 |
| EP | 1141028 A2 | 10/2001 |
| EP | 1212422 A2 | 6/2002 |
| EP | 1262193 A1 | 12/2002 |
| EP | 1513794 A2 | 3/2005 |
| EP | 1537878 A1 | 6/2005 |
| EP | 1639010 A2 | 3/2006 |
| EP | 1869067 A1 | 12/2007 |
| EP | 1896582 A1 | 3/2008 |
| EP | 2112166 A2 | 10/2009 |
| EP | 2161336 A1 | 3/2010 |
| EP | 2206517 A1 | 7/2010 |
| EP | 2240204 A1 | 10/2010 |
| EP | 2243493 A1 | 10/2010 |
| EP | 2418278 A2 | 2/2012 |
| EP | 2439272 A2 | 4/2012 |
| EP | 2439273 A2 | 4/2012 |
| EP | 2501822 A2 | 9/2012 |
| EP | 2850102 A1 | 3/2015 |
| EP | 3049442 A1 | 8/2016 |
| EP | 3114144 A1 | 1/2017 |
| EP | 3142697 A1 | 3/2017 |
| EP | 3214175 A1 | 9/2017 |
| EP | 3309175 A1 | 4/2018 |
| JP | 2008-074859 A | 4/2008 |
| JP | 2013-032387 A | 2/2013 |
| JP | 2014-500004 A | 1/2014 |
| JP | 2014-512809 A | 5/2014 |
| KR | 10-2014-0033013 A | 3/2014 |
| WO | WO-95/33770 A1 | 12/1995 |
| WO | WO-96/34090 A1 | 10/1996 |
| WO | WO-97/20574 A1 | 6/1997 |
| WO | WO-98/42752 A1 | 10/1998 |
| WO | WO-2000037504 A2 | 6/2000 |
| WO | WO-01/14424 A2 | 3/2001 |
| WO | WO-01/54732 A1 | 8/2001 |
| WO | WO-03/086459 A1 | 10/2003 |
| WO | WO-2004/004771 A1 | 1/2004 |
| WO | WO-04/029069 A2 | 4/2004 |
| WO | WO-05/003298 A2 | 1/2005 |
| WO | WO-05/092380 A2 | 10/2005 |
| WO | WO-06/110277 A1 | 10/2006 |
| WO | WO-06/121168 A1 | 11/2006 |
| WO | WO-07/113648 A2 | 10/2007 |
| WO | WO-09/100140 A1 | 8/2009 |
| WO | WO-11/044180 A1 | 4/2011 |
| WO | WO-11/045704 A1 | 4/2011 |
| WO | WO-11/062926 A2 | 5/2011 |
| WO | WO-2012038606 A1 | 3/2012 |
| WO | WO-2012120125 A1 | 9/2012 |
| WO | WO-13/003761 A1 | 1/2013 |
| WO | WO-13/142796 A2 | 9/2013 |
| WO | WO-13/173223 A1 | 11/2013 |
| WO | WO-15/048312 A1 | 4/2015 |
| WO | WO-2015/134605 A1 | 9/2015 |
| WO | WO-15/176033 A1 | 11/2015 |
| WO | WO-16/100561 A2 | 6/2016 |
| WO | WO-16/131769 A2 | 8/2016 |
| WO | WO-16/183469 A1 | 11/2016 |
| WO | WO-17/132508 A1 | 8/2017 |

OTHER PUBLICATIONS

Bird et al.,"Single-chain antigen-binding protreins", Science 242:423-426 (1988).

Brummell et al., "Probing the combining site of an anti-carbohydrate antibody by saturation-mutagenesis: role of the heavy-chain CDR3 residues", Biochemistry 32:1180-1187 (1993).

Burks et al., "In vitro scanning saturation mutagenesis of an antibody binding pocket", Proc. Natl Acad. Set USA 94:412-417 (1997).

Calabró et al., "CTLA4 blockade in mesothelioma: finally a competing strategy over cytotoxic/target therapy?" Cancer Immunology Immunotherapy, Springer, Berlin/Heidelberg, vol. 64, No. 1, pp. 105-112 (Sep. 19, 2014).

Choi et al., "Recombinant chimeric OKT3 scFv IgM antibodies mediate immune suppression while reducing T cell activation in vitro", Eur.J.Immunol. 31:94-106 (2001).

Chothia et al., "Conformations of immunoglobulin hypervariable regions", Nature 342:878-883 (1989).

Chothia et al., L"Canonical structures for the hypervariable regions of immunoglobins", J.Mol.Biol. 196:901-917 (1987).

Clark et al., "Antibody humanizaation: a case of the 'Emperor's new clothes'?", Immunol. Today 21:397 402 (2000).

Du et al., "Tumor-specific oncolytic adenoviruses expressing granulocyte macrophage colony-stimulating factor for anti-CTLA4 antibody for the treatment of cancers", Cancer Gene Therapy, vol. 21, No. 8, pp. 340-348 (Jul. 18, 2014).

Examination Report No. 1 dated Oct. 26, 2017 in corresponding AU Appl. No. 2015295936.

Examination Report dated Oct. 5, 2018 in corresponding CL Appl. No. 00250-2017.

Fransen et al., "Controlled local delivery of CTLA-4 blocking antibody induces CD8+ T-cell-dependent tumor eradication and decreases risk of toxic side effects", Clinical Cancer Research, vol. 19, No. 19 pp. 5381-5389 (Oct. 2013).

Fransen et al., "Local immunomodulation for cancer therapy: providing treatment where needed", Oncoimmunology, vol. 2, No. 11, pp. e26493 (Nov. 1, 2013).

Grosso et al., CTLA-4 blockade in tumor models: an overview of preclinical and translational research, Cancer Innum. (2013): 13:5: 1-14.

Hardcastle et al., "Modulation of innate immunity with the anti-CTLA4 antibody ipilimumab (Ipi) in measles virotherapy for glioblastoma", Molecular Therapy, vol. 21, Suppl. 1, pp. S9 (Jun. 2013).

Hodi et al., "Improved survival with ipilimumab in patients with metastatic melanoma", New England Journal of Medicine, vol. 363, No. 8, pp. 711-723 (Aug. 19, 2010).

(56) References Cited

OTHER PUBLICATIONS

Holliger et al., "Diabodies", Proc. Natl. Acad. Sci. USA 90(14): 6444-6448 (1993).
Hu et al., Minibody: a novel engineered anti-carcinoembryonic antigen antibody fragment (single-chain Fv-CH3) which exhibits rapid, high-level targeting of Xenografts, Cancer Res. 56:3055-3061 (1996).
Huston et al., "Protein engineering of antibody binding sites: recovery of specific activity in an antidigoxin single-chain Fv analogue produced in *Escherichia coli*", Proc.Natl.Acad.Sci.USA 85:5879-5883 (1988).
International Search Report dated Nov. 20, 2015 in corresponding International Appl. No. PCT/CN2015/085721.
Jones et al., "Replacing the complementarity-determining regions in a human antibody with those from a mouse", Nature 321:522 525 (1986).
Kipriyanov et al., "Bispecific tandem diabody for tumor therapy with improved antigen binding and pharmacokinetics", J.Mol. Biol. 293:41-56 (1999).
Kobayashi et al., "Tryptophan H33 plays an important role in pyrimidine (6-4) pyrimidone photoproduct binding by a high-affinity antibody", Kobayashi, Protein Eng.12 (10):879-884 (1999).
Kohler et al., "Continuous cultures of fused cells secreting antibody of predefined specificity", Nature 256:495 (1975).
Lipson et al., "Ipilimumab: an anti-CTLA-4 antibody for metastatic melanoma", Clin. Cancer Res. 17(22) (2011).
Maki et al., "A pilot study of anti-CTLA4 antibody ipilimumab in patients with synovial sarcoma", *Sarcoma*, vol. 2013, Article ID 168145, pp. 1-8 (2013).
Mellman et al., "Cancer immunotherapy comes of age", *Nature*, vol. 480, No. 7378, pp. 480-489 (Jan. 1, 2011).
Menzies et al., "Recent advances in melanoma systemic therapy. BRAF inhibitors, CTLA4 antibodies and beyond", *European Journal of Cancer*, vol. 49, No. 15, pp. 3229-3241 (Oct. 1, 2013).
Morrison et al., "Chimeric human antibody molecules: mouse antigen-binding domains with human constant region domains", Proc. Natl. Acad. Sci. USA?81:6851 6855 (1984).
Myers et al., "Optimal alignments in linear space", Comput. Appl Biosci. 4:11-17 (1988).
Needleman et al., "A general method applicable to the search for similarities in the amino acid sequence of two proteins", J. Mol .Biol. 48:443-453 (1970).
Office Action dated Mar. 14, 2017 in corresponding CO Appl. No. NC2017/0000754.
Office Action dated Apr. 11, 2017 in corresponding VN Appl. No. 1-2017-00481.
Office Action dated Dec. 28, 2017 in corresponding CA Appl. No. 2,956,000.
Office Action dated Jul. 3, 2018 in corresponding EA Appl. No. 201790288.
Office Action dated Jul. 30, 2018 in corresponding GE Appl. No. AP2015014437.
Office Action dated Sep. 4, 2018 in corresponding JP Appl. No. 2017-525666.
Office Action dated Sep. 6, 2017 in corresponding TH Appl. No. 1701000544.
Office Action dated May 9, 2018 in corresponding KR Appl. No. 10-2017-7005688.
Poljak et al., "Production and structure of diabodies", Structure 2:1121-1123 (1994).
Presta et al., "Antibody engineering", Curr. Op. Struct. Biol. 2:593 596 (1992).
Previous Search Results in priority application No. CN201410377352 http://cpquery.sipo.gov.cn.
Riechmann et al.?"Reshaping human antibodies for therapy", Nature 332:323 329 (1988).
Search Report dated Jan. 30, 2017 in corresponding PA Appl. No. 91482-01.
Shao et al., "Nanoparticle-based immunotherapy for cancer", *ACS NANO*, vol. 9, No. 1, 27, pp. 16-30 (Jan. 27, 2015).
Supplementary Search Report dated Feb. 13, 2018 in corresponding EP Appl. No. 15827441.5.
Ward et al., "Binding activities of a repertoire of single immunoglobulin variable domains secreted from *Escherichia coli*", Nature 341: 544-546 (1989).
Written Opinion dated Feb. 5, 2018 in corresponding SG Appl. No. 11201700819Q.
Xu et al., Preparation and characterization of a chimeric anti-human CTLA-4 monoclonal antibody, Second Military Medical University, Shanghai 200433, China (2012).
Office Action dated Dec. 28, 2018 in corresponding EA App. No. 201790288.
Marri et al., Human Biochemistry, "Mir" 1993, vol. 1, p. 34.
Office Action dated Mar. 12, 2020 in corresponding PE Appl. No. 000155-2017/DIN.
Office Action dated Apr. 20, 2020 in corresponding CN Appl. No. 201580040171.X.
Extended European Search Report dated Apr. 7, 2020 in corresponding EP Appl. No. 17844198.6.
Zhou et al., "CTLA-4 monoclonal antibody-targeted passive immunotherapy for tumor," *Chinese Clinical Oncology*, 2013, 18(3): 268-272 [Partial translation].
Persson et al., "Intratumoral Expression of CTLA4 Monoclonal Antibody Induces Immunosuppressive NKT Cells in a Mouse Model of Breast Cancer with Tolerance to Her2/neu," *Molecular Therapy*, 2011, 19(Suppl 1): S88-S89.
Hanaizi et al., "The European Medicines Agency review of ipilimumab (Yervoy) for the treatment of advanced (unresectable or metastatic) melanoma in adults who have received prior therapy: Summary of the scientific assessment of the Committee for Medicinal Products for Human Use," *European Journal of Cancer*, 2012, 48(2): 237-242.
Office Action dated Jun. 2, 2020 in corresponding BB Appl. No. 2001/1872.
Office Action dated Sep. 15, 2020 in corresponding BR Appl. No. BR112017002080.
Office Action dated May 29, 2020 in corresponding PH Appl. No. 1/2017/500190.
Office Action dated Nov. 13, 2020 in corresponding MD Appl. No. a20170022.
Office Action dated Dec. 23, 2020 in corresponding VN Appl. No. 1-2017-00481.
Office Action dated Oct. 23, 2020 in corresponding SA Appl. No. 517380820.
Office Action dated Jul. 16, 2020 in corresponding MX Appl. No. MX/a/2017/001446.
Office Action dated Dec, 18, 2020 in corresponding MX Appl. No. MX/a/2017/001446 [Translation only].
Office Action dated May 20, 2020 in corresponding MD Appl. No. a20170022.
Office Action dated Feb. 8, 2021 in corresponding CA Appl. No. 2,956,000.
Office Action dated Jan. 19, 2021 in corresponding HN Appl. No. 2017-000149.
Office Action dated Jan. 25, 2021 in corresponding CN Appl. No. 201580040171.X.
Office Action dated Dec. 16, 2020 in corresponding EP Appl. No. 17844198.6.
Examination Report dated Jun. 28, 2021 in corresponding AE Appl. No. P6000071/2017.
Search Report dated Jun. 28, 2021 in corresponding AE Appl. No. P6000071/2017.
Notice of Grant dated Jul. 23, 2021 in corresponding BZ Appl. No. 892.17.
Office Action dated May 25, 2021 in corresponding CN Appl. No. 201580040171.X.
Office Action dated Jun. 9, 2021 in corresponding DO Appl. No. P2017-0031.
Extended European Search Report dated Jun. 29, 2021 in corresponding EP Appl. No. 20216429.9.
Office Action dated May 19, 2021 in corresponding HN Appl. No. 2017000149.

(56) References Cited

OTHER PUBLICATIONS

Office Action dated Jun. 7, 2021 in corresponding MD Appl. No. a20170022 [Partial translation].
Office Action dated Jul. 6, 2021 in corresponding NI Appl. No. 2017-000008.
Office Action dated Sep. 3, 2021 in corresponding HN Appl. No. 2017000149.
Office Action dated Sep. 9, 2021 in corresponding MY Appl. No. PI 2017000162.
Office Action dated Feb. 17, 2021 in corresponding LK Appl. No. 19169.
Office Action dated Mar. 1, 2021 in corresponding MD Appl. No. a20170022.
Office Action dated Apr. 7, 2021 in corresponding BZ Appl. No. 892.17.
Office Action dated Oct. 6, 2021 in corresponding SV Appl. No. 2017005370.

* cited by examiner

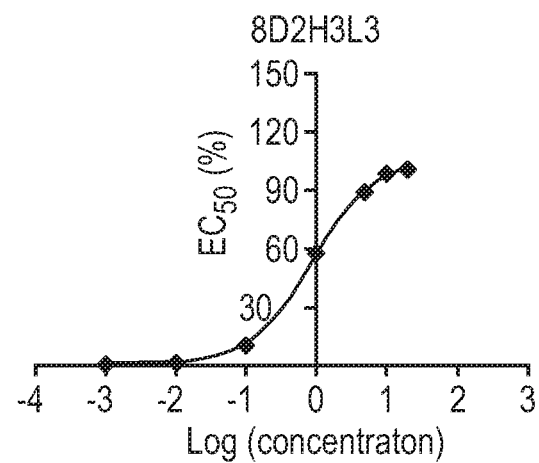
FIG. 15
FIG. 16
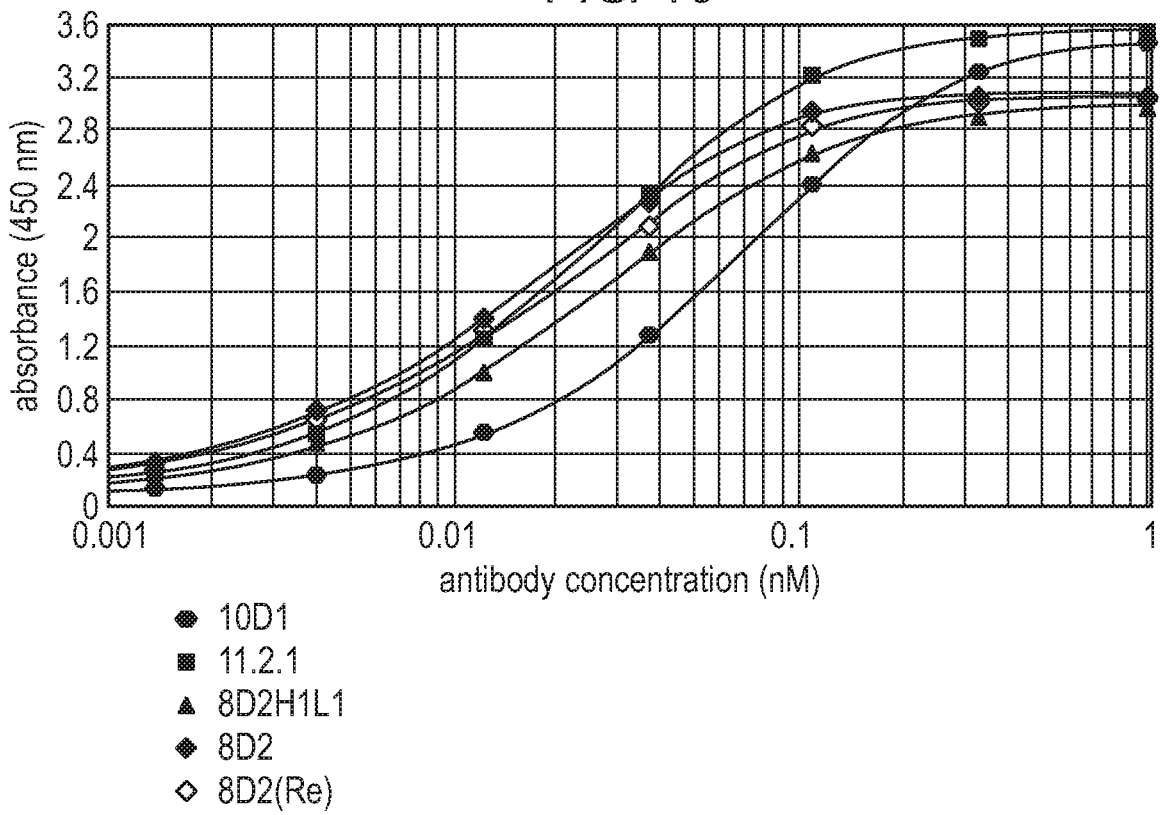

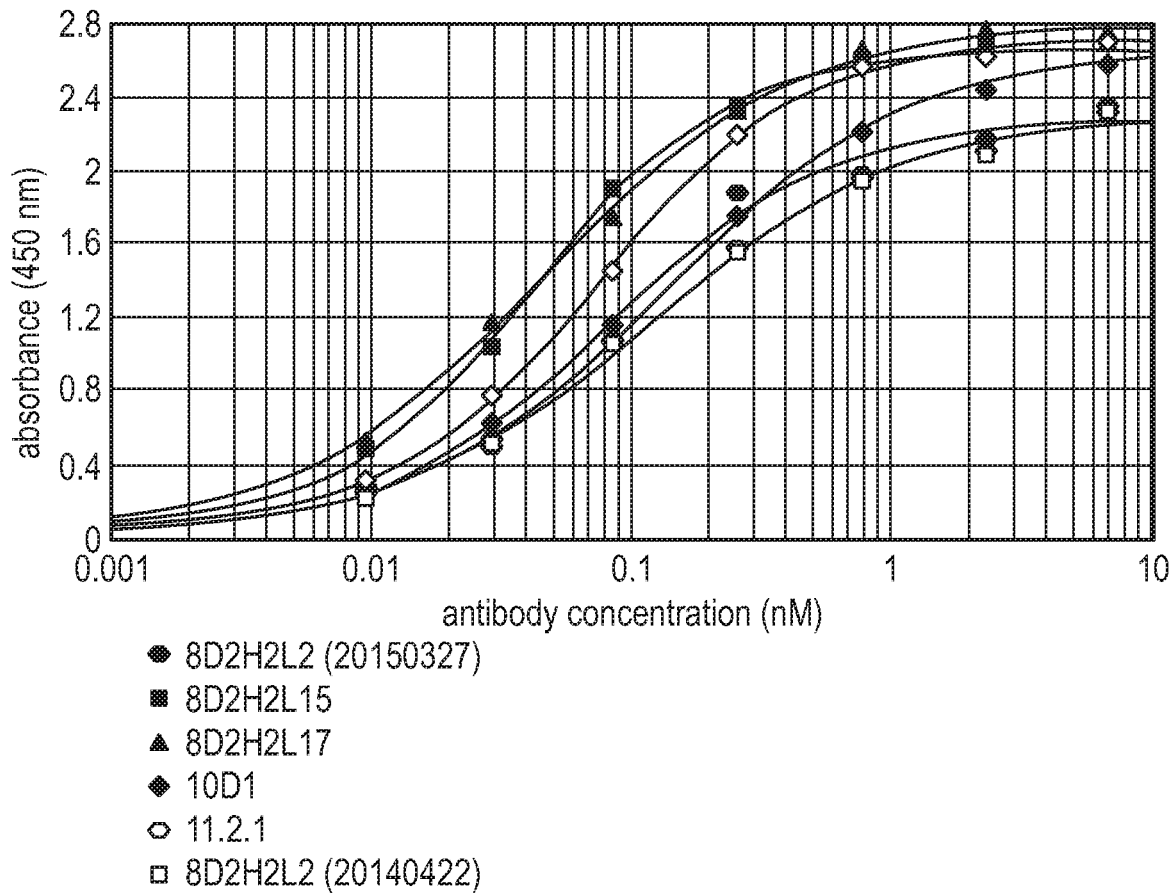
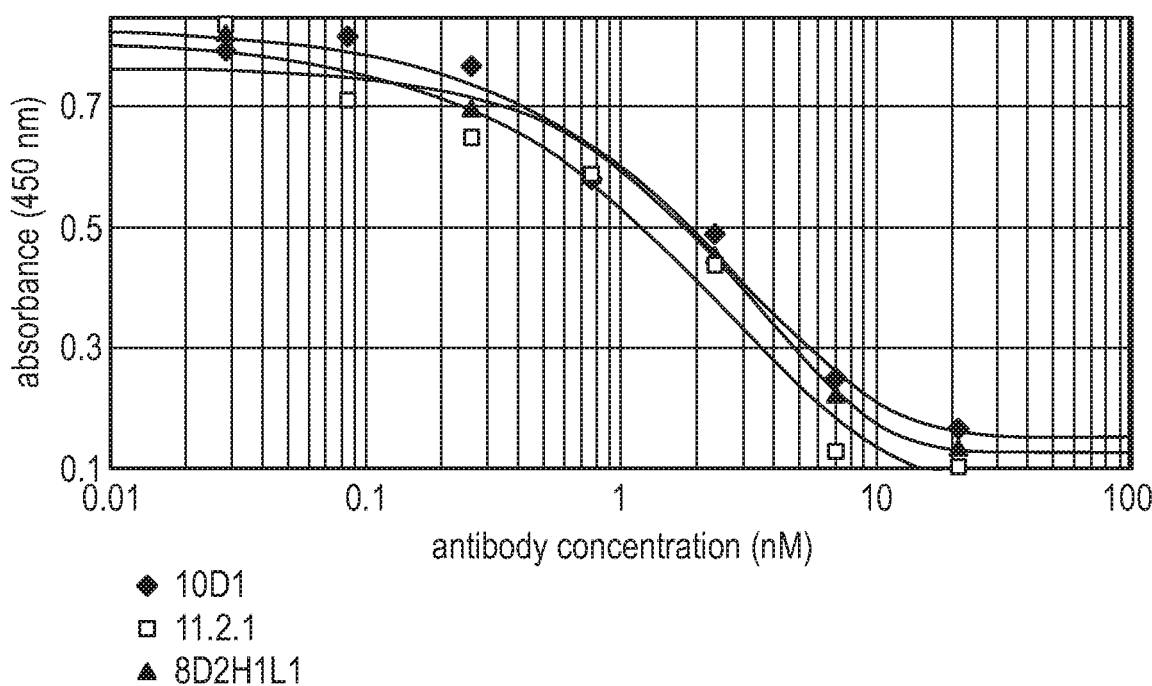

SEQUENCE LISTING

```
<160> NUMBER OF SEQ ID NOS: 34

<210> SEQ ID NO 1
<211> LENGTH: 375
<212> TYPE: DNA
<213> ORGANISM: Artificial sequence
<220> FEATURE:
<223> OTHER INFORMATION: the nucleic acid sequence encoding the CTLA4ECD
      protein

<400> SEQUENCE: 1
gcaatgcacg tggcccagcc tgctgtggta ctggccagca gccgaggcat cgccagcttt      60
gtgtgtgagt atgcatctcc aggcaaagcc actgaggtcc gggtgacagt gcttcggcag     120
gctgacagcc aggtgactga agtctgtgcg gcaacctaca tgatggggaa tgagttgacc     180
ttcctagatg attccatctg cacgggcacc tccagtggaa atcaagtgaa cctcactatc     240
caaggactga gggccatgga cacgggactc tacatctgca aggtggagct catgtaccca     300
ccgccatact acctgggcat aggcaacgga acccagattt atgtaattga tccagaaccg     360
tgcccagatt ctgac                                                      375

<210> SEQ ID NO 2
<211> LENGTH: 125
<212> TYPE: PRT
<213> ORGANISM: Artificial sequence
<220> FEATURE:
<223> OTHER INFORMATION: the amino acid sequence of the CTLA4ECD protein

<400> SEQUENCE: 2

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
        35                  40                  45
```

```
Cys Ala Ala Thr Tyr Met Met Gly Asn Glu Leu Thr Phe Leu Asp Asp
        50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                    85                  90                  95

Leu Met Tyr Pro Pro Pro Tyr Tyr Leu Gly Ile Gly Asn Gly Thr Gln
               100                 105                 110

Ile Tyr Val Ile Asp Pro Glu Pro Cys Pro Asp Ser Asp
               115                 120                 125

<210> SEQ ID NO 3
<211> LENGTH: 364
<212> TYPE: PRT
<213> ORGANISM: Artificial sequence
<220> FEATURE:
<223> OTHER INFORMATION: the amino acid sequence of the CTLA4ECD-mFc
      chimeric protein

<400> SEQUENCE: 3

Ala Met His Val Ala Gln Pro Ala Val Val Leu Ala Ser Ser Arg Gly
 1               5                  10                  15

Ile Ala Ser Phe Val Cys Glu Tyr Ala Ser Pro Gly Lys Ala Thr Glu
                20                  25                  30

Val Arg Val Thr Val Leu Arg Gln Ala Asp Ser Gln Val Thr Glu Val
            35                  40                  45

Cys Ala Ala Thr Tyr Met Met Gly Asn Glu Leu Thr Phe Leu Asp Asp
        50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                    85                  90                  95

Leu Met Tyr Pro Pro Pro Tyr Tyr Leu Gly Ile Gly Asn Gly Thr Gln
               100                 105                 110

Ile Tyr Val Ile Asp Pro Glu Pro Cys Pro Asp Ser Asp Glu Asn Leu
               115                 120                 125

Tyr Phe Gln Gly Pro Arg Gly Pro Thr Ile Lys Pro Cys Pro Pro Cys
   130                 135                 140

Lys Cys Pro Ala Pro Asn Leu Leu Gly Gly Pro Ser Val Phe Ile Phe
145                 150                 155                 160

Pro Pro Lys Ile Lys Asp Val Leu Met Ile Ser Leu Ser Pro Ile Val
               165                 170                 175

Thr Cys Val Val Val Asp Val Ser Glu Asp Asp Pro Asp Val Gln Ile
               180                 185                 190

Ser Trp Phe Val Asn Asn Val Glu Val His Thr Ala Gln Thr Gln Thr
           195                 200                 205

His Arg Glu Asp Tyr Asn Ser Thr Leu Arg Val Val Ser Ala Leu Pro
       210                 215                 220

Ile Gln His Gln Asp Trp Met Ser Gly Lys Glu Phe Lys Cys Lys Val
225                 230                 235                 240

Asn Asn Lys Asp Leu Pro Ala Pro Ile Glu Arg Thr Ile Ser Lys Pro
                245                 250                 255

Lys Gly Ser Val Arg Ala Pro Gln Val Tyr Val Leu Pro Pro Pro Glu
               260                 265                 270

Glu Glu Met Thr Lys Lys Gln Val Thr Leu Thr Cys Met Val Thr Asp
           275                 280                 285
```

```
         Phe Met Pro Glu Asp Ile Tyr Val Glu Trp Thr Asn Asn Gly Lys Thr
             290                 295                 300

Glu Leu Asn Tyr Lys Asn Thr Glu Pro Val Leu Asp Ser Asp Gly Ser
         305                 310                 315                 320

Tyr Phe Met Tyr Ser Lys Leu Arg Val Glu Lys Lys Asn Trp Val Glu
                         325                 330                 335

Arg Asn Ser Tyr Ser Cys Ser Val Val His Glu Gly Leu His Asn His
                     340                 345                 350

His Thr Thr Lys Ser Phe Ser Arg Thr Pro Gly Lys
                     355                 360

<210> SEQ ID NO 4
<211> LENGTH: 1092
<212> TYPE: DNA
<213> ORGANISM: Artificial sequence
<220> FEATURE:
<223> OTHER INFORMATION: the nucleic acid sequence encoding the
      CTLA4ECD-mFc chimeric protein

<400> SEQUENCE: 4
gcaatgcatg tcgcacagcc tgcagtggtc ctggcaagct ccaggggaat cgctagcttc        60
gtgtgcgaat acgcttcccc aggcaaggca accgaggtcc gggtgacagt cctgagacag      120
gccgacagcc aggtgacaga agtctgcgcc gctacttata tgatgggcaa cgagctgacc      180
tttctggacg atagcatttg taccgggaca tctagtggaa accaagtgaa tctgaccatc      240
cagggcctgc gcgctatgga cacagggctg tacatttgta agtggagct gatgtatccc       300 cctccatact atctgggaat cggcaacggg acccagatct acgtgattga tcctgaacca      360
tgccccgact ccgatgagaa tctgtatttc cagggaccac gaggcccac aattaagcca       420 tgtcccccett gcaaatgtcc tgcaccaaac ctgctgggag gaccaagcgt gttcatcttt      480
ccacccaaga tcaaggacgt gctgatgatc tcactgagcc ccattgtgac ctgcgtggtc      540
gtggacgtga gcgaggacga tcctgatgtg cagatcagtt ggttcgtcaa caatgtggaa      600
gtccacacag ctcagactca gacccatagg gaggattaca atagtactct gcgcgtcgtg      660
tcagcactgc ccattcagca ccaggactgg atgagcggca aggagttcaa gtgcaaagtg      720
aacaacaagg atctgccccgc acctatcgag agaactattt ccaagcctaa agggtctgtg     780 agggcccca c aggtgtatgt cctgcctcca cccgaggaag atgactaa gaaacaggtg       840 acactgactt gtatggtcac cgacttcatg cccgaagata tctacgtgga gtggactaac      900
aatgggaaga ccgaactgaa ctataaaaat acagagcctg tgctggactc agatggaagc      960
tactttatgt atagcaagct gcgagtggaa aagaaaaact gggtcgagcg aacagctac      1020 tcttgtagtg tggtccacga agggctgcat aatcaccaca ccactaaatc attctcccga     1080
actccaggca aa                                                        1092

<210> SEQ ID NO 5
<211> LENGTH: 345
<212> TYPE: DNA
<213> ORGANISM: Artificial sequence
<220> FEATURE:
<223> OTHER INFORMATION: the nucleic acid sequence encoding the heavy
      chain variable domain of the monoclonal antibody 8D2

<400> SEQUENCE: 5
gaggtgaaac tggacgaaac tggcggggg ctggtgcagc ccggacgacc tatgaagctg        60
tcatgcgtcg ccagcggctt cacctttagc gacaactgga tgaattgggt gaggcagagc      120
```

```
ccagagaagg ggctggaatg gctggctcag atccgcaaca aaccctacaa ttatgagacc        180
tactattctg acagtgtgaa gggccggttc acaatttcca gagacgattc taaaagctcc        240
gtctacctgc agatgaacaa tctgagaggc aagatatgg ggatctacta ttgcacagca         300
cagttcgctt attggggaca gggcactctg gtcacagtct ccgcc                       345

<210> SEQ ID NO 6
<211> LENGTH: 115
<212> TYPE: PRT
<213> ORGANISM: Artificial sequence
<220> FEATURE:
<223> OTHER INFORMATION: the amino acid sequence of the heavy chain
      variable domain of the monoclonal antibody 8D2

<400> SEQUENCE: 6

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Asn
            20                  25                  30

Trp Met Asn Trp Val Arg Gln Ser Pro Glu Lys Gly Leu Glu Trp Leu
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Gly Glu Asp Met Gly Ile Tyr
                85                  90                  95

Tyr Cys Thr Ala Gln Phe Ala Tyr Trp Gly Gln Gly Thr Leu Val Thr
            100                 105                 110

Val Ser Ala
        115

<210> SEQ ID NO 7
<211> LENGTH: 318
<212> TYPE: DNA
<213> ORGANISM: Artificial sequence
<220> FEATURE:
<223> OTHER INFORMATION: the nucleic acid sequence encoding the light
      chain variable domain of the monoclonal antibody 8D2

<400> SEQUENCE: 7
gacattcaga tgacacagag tcctgcttcc ctgagtgcct cagtggggga gaccgtcaca         60
atcacttgcg gcacctctga aaacatctac ggcgggctga attggtatca gcggaagcag        120
ggcaaaagtc cccagctgct gatcttcgga gcaacaaacc tggccgacgg catgagctcc        180
cggtttagcg gtccggatc tggcagacag tacagcctga agatttctag tctgcaccca         240
gacgatgtgg ctacttacta ttgccagaat gtcctgagga gtcccttcac ctttgggtca        300
ggaacaaagc tggagatc                                                      318

<210> SEQ ID NO 8
<211> LENGTH: 106
<212> TYPE: PRT
<213> ORGANISM: Artificial sequence
<220> FEATURE:
<223> OTHER INFORMATION: the amino acid sequence of the light chain
      variable domain of the monoclonal antibody 8D2

<400> SEQUENCE: 8

Asp Ile Gln Met Thr Gln Ser Pro Ala Ser Leu Ser Ala Ser Val Gly
```

```
  1               5                  10                 15
Glu Thr Val Thr Ile Thr Cys Gly Thr Ser Glu Asn Ile Tyr Gly Gly
                    20                 25                 30

Leu Asn Trp Tyr Gln Arg Lys Gln Gly Lys Ser Pro Gln Leu Leu Ile
            35                 40                 45

Phe Gly Ala Thr Asn Leu Ala Asp Gly Met Ser Ser Arg Phe Ser Gly
        50                 55                 60

Ser Gly Ser Gly Arg Gln Tyr Ser Leu Lys Ile Ser Ser Leu His Pro
65                  70                 75                 80

Asp Asp Val Ala Thr Tyr Tyr Cys Gln Asn Val Leu Arg Ser Pro Phe
                85                 90                 95

Thr Phe Gly Ser Gly Thr Lys Leu Glu Ile
                100                105

<210> SEQ ID NO 9
<211> LENGTH: 345
<212> TYPE: DNA
<213> ORGANISM: Artificial sequence
<220> FEATURE:
<223> OTHER INFORMATION: the nucleic acid sequence encoding the heavy
      chain variable domain of the monoclonal antibody 8D2H1L1

<400> SEQUENCE: 9
gaagtgcagc tggtcgagtc cggggggggc ctggtgcagc caggaggatc aatgcgactg      60
agctgcgccg cttccggctt caccttcagc gacaactgga tgaattgggt caggcaggca    120
ccaggaaagg gactggagtg gctggcacag atccgcaaca aaccttacaa ctacgaaact    180
tactacagcg actccgtgaa ggggcggttc accatttcta gagacgattc taaaaacagt    240
gtgtacctgc agatgaatag cctgaagacc gaggatacag gagtctacta ttgtaccgca    300
cagtttgctt attgggggca gggcactctg gtgacagtct cttca                    345

<210> SEQ ID NO 10
<211> LENGTH: 115
<212> TYPE: PRT
<213> ORGANISM: Artificial sequence
<220> FEATURE:
<223> OTHER INFORMATION: the amino acid sequence of the light chain
      variable domain of the monoclonal antibody 8D2H1L1

<400> SEQUENCE: 10

Glu Val Gln Leu Val Glu Ser Gly Gly Gly Leu Val Gln Pro Gly Gly
1               5                  10                 15

Ser Met Arg Leu Ser Cys Ala Ala Ser Gly Phe Thr Phe Ser Asp Asn
                20                 25                 30

Trp Met Asn Trp Val Arg Gln Ala Pro Gly Lys Gly Leu Glu Trp Leu
            35                 40                 45

Ala Gln Ile Arg Asn Lys Pro Tyr Asn Tyr Glu Thr Tyr Tyr Ser Asp
        50                 55                 60

Ser Val Lys Gly Arg Phe Thr Ile Ser Arg Asp Asp Ser Lys Asn Ser
65                  70                 75                 80

Val Tyr Leu Gln Met Asn Ser Leu Lys Thr Glu Asp Thr Gly Val Tyr
                85                 90                 95

Tyr Cys Thr Ala Gln Phe Ala Tyr Trp Gly Gln Gly Thr Leu Val Thr
                100                105                110

Val Ser Ser
        115
```

```
<210> SEQ ID NO 11
<211> LENGTH: 321
<212> TYPE: DNA
<213> ORGANISM: Artificial sequence
<220> FEATURE:
<223> OTHER INFORMATION: the nucleic acid sequence encoding the light
      chain variable domain of the monoclonal antibody 8D2H1L1

<400> SEQUENCE: 11
gacattcaga tgactcagag cccttcaagc ctgtccgcat ctgtgggcga ccgagtcacc      60
atcacatgca gaacctccga gaacatctac ggcgggctga attggtatca gcgaaagcag     120
gggaaaagtc ccaagctgct gatctacggg gcaacaaacc tggccagcgg aatgagctcc     180
agattcagtg gatcaggcag cgggacagat tatactctga aaatttctag tctgcaccca     240
gacgatgtgg caacctacta ttgccagaat gtcctgaggt cacccttcac ctttggaagc     300
ggcacaaaac tggagatcaa g                                               321

<210> SEQ ID NO 12
<211> LENGTH: 107
<212> TYPE: PRT
<213> ORGANISM: Artificial sequence
<220> FEATURE:
<223> OTHER INFORMATION: the amino acid sequence of the light chain
      variable domain of the monoclonal antibody 8D2H1L1

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30

Leu Asn Trp Tyr Gln Arg Lys Gln Gly Lys Ser Pro Lys Leu Leu Ile
        35                  40                  45

Tyr Gly Ala Thr Asn Leu Ala Ser Gly Met Ser Ser Arg Phe Ser Gly
    50                  55                  60

Ser Gly Ser Gly Thr Asp Tyr Thr Leu Lys Ile Ser Ser Leu His Pro
65                  70                  75                  80

Asp Asp Val Ala Thr Tyr Tyr Cys Gln Asn Val Leu Arg Ser Pro Phe
                85                  90                  95

Thr Phe Gly Ser Gly Thr Lys Leu Glu Ile Lys
            100                 105

<210> SEQ ID NO 13
<211> LENGTH: 345
<212> TYPE: DNA
<213> ORGANISM: Artificial sequence
<220> FEATURE:
<223> OTHER INFORMATION: the nucleic acid sequence encoding the heavy
      chain variable domain of the monoclonal antibody 8D2H2L2, 8D2H2L15
      or 8D2H2L17

<400> SEQUENCE: 13
gaagtgcagc tggtcgagtc cggggggggc ctggtgcagc caggaggatc aatgcgactg      60
agctgcgccg cttccggctt caccttcagc gacaactgga tgaattgggt caggcaggca     120
ccaggaaagg gactggagtg gctggcacag atccgcaaca aaccttacaa ctacgaaact     180
tactacagcg cctccgtgaa ggggcggttc accatttcta gagacgattc taaaaacagt     240
gtgtacctgc agatgaatag cctgaagacc gaggatacag gagtctacta ttgtaccgca     300
cagtttgctt attgggggca gggcactctg gtgacagtct cttca                    345
```

```
<210> SEQ ID NO 14
<211> LENGTH: 115
<212> TYPE: PRT
<213> ORGANISM: Artificial sequence
<220> FEATURE:
<223> OTHER INFORMATION: the amino acid sequence of the heavy chain
      variable domain of the monoclonal antibody 8D2H2L2, 8D2H2L15 or
      8D2H2L17

<400> SEQUENCE: 14
```

Glu Val Gln Leu Val Glu Ser Gly Gly Gly Leu Val Gln Pro Gly Gly
1               5                   10                  15

Ser Met Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Leu
        35                  40                  45

Ala Gln Ile Arg Asn Lys Pro Tyr Asn Tyr Glu Thr Tyr Tyr Ser Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Ala Gln Phe Ala Tyr Trp Gly Gln Gly Thr Leu Val Thr
            100                 105                 110

Val Ser Ser
        115

```
<210> SEQ ID NO 15
<211> LENGTH: 321
<212> TYPE: DNA
<213> ORGANISM: Artificial sequence
<220> FEATURE:
<223> OTHER INFORMATION: the nucleic acid sequence encoding the light
      chain variable domain of the monoclonal antibody 8D2H2L2

<400> SEQUENCE: 15
gacattcaga tgactcagag cccttcaagc ctgagtgcct cagtgggaga ccgggtcacc        60
atcacatgca gaaccagcga gaacatctac ggcggcctga actggtatca gcgaaagcca       120
ggcaagagcc ccaagctgct gatctacggg gcaaccaacc tggcctctgg agtgagctcc       180
agattcagcg gcagcggctc tgggaccgac tatactctga ccatttctag tctgcagcct       240
gaagatgtgg caacatacta ttgccagaat gtcctgaggt ccccattcac ctttggatct       300
ggcaccaagc tggagatcaa g                                                 321

<210> SEQ ID NO 16
<211> LENGTH: 107
<212> TYPE: PRT
<213> ORGANISM: Artificial sequence
<220> FEATURE:
<223> OTHER INFORMATION: the amino acid sequence of the light chain
      variable domain of themonoclonal antibody 8D2H2L2

<400> SEQUENCE: 16
```

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30

Leu Asn Trp Tyr Gln Arg Lys Pro Gly Lys Ser Pro Lys Leu Leu Ile
        35                  40                  45

Tyr Gly Ala Thr Asn Leu Ala Ser Gly Val Ser Ser Arg Phe Ser Gly

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Asn Val Leu Arg Ser Pro Phe
                85                  90                  95

Thr Phe Gly Ser Gly Thr Lys Leu Glu Ile Lys
            100                 105

<210> SEQ ID NO 17
<211> LENGTH: 345
<212> TYPE: DNA
<213> ORGANISM: Artificial sequence
<220> FEATURE:
<223> OTHER INFORMATION: the nucleic acid sequence encoding the heavy
      chain variable domain of the monoclonal antibody 8D2H3L3

<400> SEQUENCE: 17
gaggtgcagc tggtcgagtc tggaggcggc ctggtgcagc ccggcgggtc actgcgactg      60
agctgcgccg cttccggctt caccttcagc gacaactgga tgaattgggt gaggcaggca     120
cccgggaagg gctggagtg gtcgctcag atccgcaaca aaccttacaa ttatgagaca       180
gaatacgcag cctctgtgaa ggggcggttc actattagta gagacgatag caagaacagc    240
gcctatctgc agatgaatag cctgaagacc gaagatacag ccgtctacta ttgtacagct    300
cagtttgcat actgggggcca gggaactctg gtgaccgtca gctcc                    345

<210> SEQ ID NO 18
<211> LENGTH: 115
<212> TYPE: PRT
<213> ORGANISM: Artificial sequence
<220> FEATURE:
<223> OTHER INFORMATION: the amino acid sequence of the heavy chain
      variable domain of the monoclonal antibody 8D2H3L3

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Val
        35                  40                  45

Ala Gln Ile Arg Asn Lys Pro Tyr Asn Tyr Glu Thr Glu Tyr Ala Ala
    50                  55                  60

Ser Val Lys Gly Arg Phe Thr Ile Ser Arg Asp Asp Ser Lys Asn Ser
65                  70                  75                  80

Ala Tyr Leu Gln Met Asn Ser Leu Lys Thr Glu Asp Thr Ala Val Tyr
                85                  90                  95

Tyr Cys Thr Ala Gln Phe Ala Tyr Trp Gly Gln Gly Thr Leu Val Thr
            100                 105                 110

Val Ser Ser
        115

<210> SEQ ID NO 19
<211> LENGTH: 321
<212> TYPE: DNA
<213> ORGANISM: Artificial sequence
<220> FEATURE:
<223> OTHER INFORMATION: the nucleic acid sequence encoding the light
      chain variable domain of the monoclonal antibody 8D2H3L3

<400> SEQUENCE: 19

-continued

```
gacattcaga tgactcagag cccttcttct ctgtccgcat ctgtgggaga ccgggtcacc    60
atcacatgca gagccagcga gaacatctac ggcggcctga actggtatca gcagaagcca   120
ggcaaagctc ccaagctgct gatctacgga gcaacctccc tggcatctgg agtgccatcc   180
cggttcagtg atcaggcag cgggaccgac tatactctga ccattagctc cctgcagcct    240
gaagacttcg ccacatacta ttgccagaac gtgctgaggt ccccattcac ctttggatct   300
ggcaccaagc tggagatcaa g                                              321
```

<210> SEQ ID NO 20
<211> LENGTH: 107
<212> TYPE: PRT
<213> ORGANISM: Artificial sequence
<220> FEATURE:
<223> OTHER INFORMATION: the amino acid sequence of the light chain variable domain of the monoclonal antibody 8D2H3L3

<400> SEQUENCE: 20

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Glu Asn Ile Tyr Gly Gly
            20                  25                  30

Leu Asn Trp Tyr Gln Gln Lys Pro Gly Lys Ala Pro Lys Leu Leu Ile
        35                  40                  45

Tyr Gly Ala Thr Ser Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Asn Val Leu Arg Ser Pro Phe
                85                  90                  95

Thr Phe Gly Ser Gly Thr Lys Leu Glu Ile Lys
            100                 105
```

<210> SEQ ID NO 21
<211> LENGTH: 321
<212> TYPE: DNA
<213> ORGANISM: Artificial sequence
<220> FEATURE:
<223> OTHER INFORMATION: the nucleic acid sequence encoding the light chain variable domain of the monoclonal antibody 8D2H2L15

<400> SEQUENCE: 21

```
gacatccaga tgactcagtc tcccagctcc ctgtccgctt ctgtgggcga tcgggtcact    60
atcacctgta gaaccagcga gaacatttac ggcggactga attggtatca gaggaagccc   120
gggaaaagtc ctaagctgct gatctacgga gcaacaaacc tggcctccgg cgtgtctagt   180
cgcttcagtg gatcaggcag cgggaccgac tatacactga ctatttcaag cctgcagcca   240
gaggatgtgg ccacatacta ttgccagaat gtcctgagcc ggcacccggg atttggctca   300
gggaccaaac tggaaattaa g                                              321
```

<210> SEQ ID NO 22
<211> LENGTH: 107
<212> TYPE: PRT
<213> ORGANISM: Artificial sequence
<220> FEATURE:
<223> OTHER INFORMATION: the amino acid sequence of the light chain variable domain of the monoclonal antibody 8D2H2L15

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30

Leu Asn Trp Tyr Gln Arg Lys Pro Gly Lys Ser Pro Lys Leu Leu Ile
        35                  40                  45

Tyr Gly Ala Thr Asn Leu Ala Ser Gly Val Ser Ser Arg Phe Ser Gly
    50                  55                  60

Ser Gly Ser Gly Thr Asp Tyr Thr Leu Thr Ile Ser Ser Leu Gln Pro
65              70                  75                      80

Glu Asp Val Ala Thr Tyr Tyr Cys Gln Asn Val Leu Ser Arg His Pro
                85                  90                  95

Gly Phe Gly Ser Gly Thr Lys Leu Glu Ile Lys
            100                 105
```

<210> SEQ ID NO 23
<211> LENGTH: 321
<212> TYPE: DNA
<213> ORGANISM: Artificial sequence
<220> FEATURE:
<223> OTHER INFORMATION: the nucleic acid sequence encoding the light
      chain variable domain of the monoclonal antibody 8D2H2L17

<400> SEQUENCE: 23

```
gacatccaga tgactcagtc acccagctcc ctgagtgctt cagtgggcga tcgggtcact      60
atcacctgta gaaccagcga gaacatttac ggcggactga attggtatca gaggaagccc     120
gggaaaagcc ctaagctgct gatctacgga gcaacaaacc tggcctccgg cgtgtctagt     180
cgcttcagcg gcagcggctc tggaaccgac tatacactga ctatttcaag cctgcagcca     240
gaggatgtgg ccacatacta ttgccagaat gtcctgtcct ctcgacccgg atttggcagt     300
gggaccaaac tggaaattaa g                                               321
```

<210> SEQ ID NO 24
<211> LENGTH: 107
<212> TYPE: PRT
<213> ORGANISM: Artificial sequence
<220> FEATURE:
<223> OTHER INFORMATION: the amino acid sequence of the light chain
      variable domain of the monoclonal antibody 8D2H2L17

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly
            20                  25                  30

Leu Asn Trp Tyr Gln Arg Lys Pro Gly Lys Ser Pro Lys Leu Leu Ile
        35                  40                  45

Tyr Gly Ala Thr Asn Leu Ala Ser Gly Val Ser Ser Arg Phe Ser Gly
    50                  55                  60

Ser Gly Ser Gly Thr Asp Tyr Thr Leu Thr Ile Ser Ser Leu Gln Pro
65              70                  75                      80

Glu Asp Val Ala Thr Tyr Tyr Cys Gln Asn Val Leu Ser Ser Arg Pro
                85                  90                  95

Gly Phe Gly Ser Gly Thr Lys Leu Glu Ile Lys
            100                 105
```

<210> SEQ ID NO 25
<211> LENGTH: 636

<212> TYPE: DNA
<213> ORGANISM: Artificial sequence
<220> FEATURE:
<223> OTHER INFORMATION: the nucleic acid sequence encoding the CTLA4
      protein

<400> SEQUENCE: 25

```
atgggcgtcc tgctgactca gagaaccctg ctgtccctgg tgctggcact gctgtttcct      60
tcaatggctt caatggctat gcatgtggct cagccagcag tggtcctggc aagctccagg     120
gggatcgcca gtttcgtgtg cgagtacgcc tcacctggaa aggctacaga agtccgggtg     180
actgtcctga cacaggctga ctctcaggtg accgaggtct cgccgctac atatatgatg     240
ggcaacgaac tgacctttct ggacgattcc atttgtactg cacctctag tgggaaccaa     300
gtgaatctga ctatccaggg actgcgagca atggacaccg actgtacat ttgcaaagtg     360
gagctgatgt atccccctcc atactatctg ggcatcggga atggaacaca gatctacgtg     420
attgatcccg aaccttgtcc agacagcgat ttcctgctgt ggattctggc agccgtgtca     480
agcggcctgt tctttatag ctttctgctg actgccgtct ccctgtctaa gatgctgaag     540
aaacgatccc ccctgaccac aggggtggtc gtgaaaatgc cacctaccga gcccgagtgc     600
gaaaaacagt tccagccata ctttatccct atcaat                              636
```

<210> SEQ ID NO 26
<211> LENGTH: 212
<212> TYPE: PRT
<213> ORGANISM: Artificial sequence
<220> FEATURE:
<223> OTHER INFORMATION: the amino acid sequence of the CTLA4 protein

<400> SEQUENCE: 26

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Phe Leu Leu Trp Ile Leu Ala Ala Val Ser
145                 150                 155                 160

Ser Gly Leu Phe Phe Tyr Ser Phe Leu Leu Thr Ala Val Ser Leu Ser
                165                 170                 175

Lys Met Leu Lys Lys Arg Ser Pro Leu Thr Thr Gly Val Val Val Lys
            180                 185                 190

Met Pro Pro Thr Glu Pro Glu Cys Glu Lys Gln Phe Gln Pro Tyr Phe
        195                 200                 205
```

```
Ile Pro Ile Asn
    210

<210> SEQ ID NO 27
<211> LENGTH: 8
<212> TYPE: PRT
<213> ORGANISM: Artificial sequence
<220> FEATURE:
<223> OTHER INFORMATION: the amino acid sequence of CDR

<400> SEQUENCE: 27

Gly Phe Thr Phe Ser Asp Asn Trp
1               5

<210> SEQ ID NO 28
<211> LENGTH: 10
<212> TYPE: PRT
<213> ORGANISM: Artificial sequence
<220> FEATURE:
<223> OTHER INFORMATION: the amino acid sequence of CDR

<400> SEQUENCE: 28

Ile Arg Asn Lys Pro Tyr Asn Tyr Glu Thr
1               5                   10

<210> SEQ ID NO 29
<211> LENGTH: 6
<212> TYPE: PRT
<213> ORGANISM: Artificial sequence
<220> FEATURE:
<223> OTHER INFORMATION: the amino acid sequence of CDR

<400> SEQUENCE: 29

Thr Ala Gln Phe Ala Tyr
1               5

<210> SEQ ID NO 30
<211> LENGTH: 6
<212> TYPE: PRT
<213> ORGANISM: Artificial sequence
<220> FEATURE:
<223> OTHER INFORMATION: the amino acid sequence of CDR

<400> SEQUENCE: 30

Glu Asn Ile Tyr Gly Gly
1               5

<210> SEQ ID NO 31
<211> LENGTH: 3
<212> TYPE: PRT
<213> ORGANISM: Artificial sequence
<220> FEATURE:
<223> OTHER INFORMATION: the amino acid sequence of CDR

<400> SEQUENCE: 31

Gly Ala Thr
1

<210> SEQ ID NO 32
<211> LENGTH: 9
<212> TYPE: PRT
<213> ORGANISM: Artificial sequence
<220> FEATURE:
<223> OTHER INFORMATION: the amino acid sequence of CDR

<400> SEQUENCE: 32

Gln Asn Val Leu Arg Ser Pro Phe Thr
```

```
<210> SEQ ID NO 33
<211> LENGTH: 9
<212> TYPE: PRT
<213> ORGANISM: Artificial sequence
<220> FEATURE:
<223> OTHER INFORMATION: the amino acid sequence of CDR

<400> SEQUENCE: 33

Gln Asn Val Leu Ser Arg His Pro Gly
1               5

<210> SEQ ID NO 34
<211> LENGTH: 9
<212> TYPE: PRT
<213> ORGANISM: Artificial sequence
<220> FEATURE:
<223> OTHER INFORMATION: the amino acid sequence of CDR

<400> SEQUENCE: 34

Gln Asn Val Leu Ser Ser Arg Pro Gly
1               5
```

ANTI-CTLA4 MONOCLONAL ANTIBODY OR ITS ANTIGEN BINDING FRAGMENTS, PHARMACEUTICAL COMPOSITIONS AND USES

CROSS-REFERENCE TO RELATED APPLICATIONS

This application is a continuation of prior application Ser. No. 15/500,744, filed Jan. 31, 2017, now U.S. Pat. No. 10,449,251, issued Oct. 22, 2019, which was the National Phase Application of International Application No. PCT/CN2015/085721, filed Jul. 31, 2015, which claims priority from Chinese Patent Application No. CN 201410377352.9, filed Aug. 1, 2014.

REFERENCE TO SEQUENCE LISTING SUBMITTED ELECTRONICALLY

The sequence listing of the present application is submitted electronically via EFS-Web as an ASCII formatted sequence listing with a file name 214572_0001_01_US_592764.txt, creation date of Sep. 5, 2019, and a size of 29 KB. This sequence listing submitted via EFS-Web is part of the specification and is herein incorporated by reference in its entirety.

TECHNICAL FIELD

The present invention belongs to the fields of tumor therapy and molecular immunology. The present invention relates to an anti-CTLA4 monoclonal antibody or antigen binding fragment thereof, a pharmaceutical composition thereof, encoding sequences thereof and a method of and use in diagnosis, prevention, therapy and/or adjuvant therapy using the same.

TECHNICAL BACKGROUND

Cytotoxic T lymphocyte associated antigen 4 (abbreviated as CTLA4) has very close relationship with the CD28 molecule in gene structure, chromosome location, sequence homology and gene expression. Both of them are receptors for the co-stimulative molecule B7, mainly expressed on the surface of activated T cells. However, as co-stimulating signal of lymphocyte activation, CTLA4 has opposite function to CD28. After binding to B7, CTLA4 can inhibit the activation of mouse and human T cells, playing a negative regulating role in the activation of T cells.

CTLA4 mAbs or CTLA4 ligands can prevent CTLA4 from binding to its native ligands, thereby blocking the transduction of the T cell negative regulating signal by CTLA4 and enhancing the responsivity of T cells to various antigens. In this aspect, results from in vivo and in vitro studies are substantially in concert. At present, there are some CTLA4 mAbs (10D1, 11.2.2) being tested in clinical trials for treating prostate cancer, bladder cancer, colorectal cancer, cancer of gastrointestinal tract, liver cancer, malignant melanoma, etc (CTLA-4 blockade in tumor models: an overview of preclinical and translational research. Grosso J F., Jure-Kunkel M N., Cancer Immun. 2013; 13:5. Epub 2013 Jan. 22; U.S. Pat. No. 6,984,720 B1; and U.S. Pat. No. 6,682,736 B1). Among them, 10D1 and 11.2.2 are regarded as among those anti-CTLA4 monoclonal antibodies having best effects.

Interleukin 2 (IL-2) is produced by T cells. It is a growth factor regulating a subgroup of T cells. It is also an important factor modulating immune response. It can promote and activate the expansion of B cells, and involves in antibody reaction, hematopoiesis and tumor surveillance. Recombinant human IL-2 has been approved by US FDA for the treatment of malignant tumors (including melanoma, kidney tumor, etc). It is also under clinical studies of treating chronic viral infection (Pharmacologic administration of interleukin-2. Chavez, A. R., et al., Ann N Y Acad Sci, 2009, 1182: 14-27).

As important factors affecting the function of T cells, CTLA4 and CTLA4 mAbs can produce specific therapeutic effect on diseases by interfering with the immune microenvironment in the body. They have high efficacy and remedy the deficiency of traditional medication, opening a novel pathway of gene therapy. CTLA4 and CTLA4 mAbs are being tested in experiments and various stages of clinical trials. For example, in autoimmune diseases, they effectively inhibited airway hyperresponsiveness in an animal model of asthma, prevented the development of rheumatic diseases, mediated immune tolerance to an allograft in the body, and the like. On the other hand, although biological gene therapy has not shown any adverse effect in short term clinical trials, attention should be paid to the potential effect after long term application. For example, excessive blockade of CTLA4 bound B7 signaling by CTLA4 mAbs may result in the development of autoimmune diseases. As antibodies can specifically bind to their ligands and induce the lysis of target cells or block the progress of pathology, development and utilization of drugs based on antibodies, especially humanized antibodies have important significance in the clinical treatment of malignant tumors and other immune diseases in humans.

At present, there is yet a need to develop novel antibodies blocking the binding of CTLA4 to B7, and their humanized antibodies.

SUMMARY OF THE INVENTION

After intensive studies and creative works by the inventors, recombinant CTLA4 was expressed using a mammal cell expression system, and used as the antigen to immunize mice. Hybridoma cells were obtained by fusing the mouse splenic cells with myeloma cells. After screening a great number of samples by the inventors, a hybridoma cell line capable of secreting and producing a specific monoclonal antibody which specifically binds CTLA4 and can block the binding of CTLA4 to B7 very effectively, was obtained. Furthermore, humanized antibodies were generated. Thus, the following inventions are provided.

One aspect of the present invention relates to a monoclonal antibody or antigen binding fragment thereof, wherein the monoclonal antibody comprises the complementary determining regions (CDR's) selected from the following:

HCDR1 comprising the amino acid sequence of SEQ ID NO: 27,
HCDR2 comprising the amino acid sequence of SEQ ID NO: 28, and
HCDR3 comprising the amino acid sequence of SEQ ID NO: 29;
and/or
LCDR1 comprising the amino acid sequence of SEQ ID NO: 30,
LCDR2 comprising the amino acid sequence of SEQ ID NO: 31, and
LCDR3 comprising an amino acid sequence selected from SEQ ID NO: 32, SEQ ID NO: 33, and SEQ ID NO: 34.

The monoclonal antibody or antigen binding fragment thereof according to any one of the embodiments of the present invention, wherein the amino acid sequence of the heavy chain variable region (VH) of the monoclonal antibody is selected from SEQ ID NO: 6, SEQ ID NO: 10, SEQ ID NO: 14, and SEQ ID NO: 18; and/or the amino acid sequence of the light chain variable region (VL) of the monoclonal antibody is selected from SEQ ID NO: 8, SEQ ID NO: 12, SEQ ID NO: 16, SEQ ID NO: 20, SEQ ID NO: 22, and SEQ ID NO: 24.

The monoclonal antibody or antigen binding fragment thereof according to any one of the embodiments of the present invention, wherein the monoclonal antibody comprises (1) VH as set forth in SEQ ID NO: 6 and VL as set forth in SEQ ID NO: 8;

(2) VH as set forth in SEQ ID NO: 10 and VL as set forth in SEQ ID NO: 12;

(3) VH as set forth in SEQ ID NO: 14 and VL as set forth in SEQ ID NO: 16;

(4) VH as set forth in SEQ ID NO: 18 and VL as set forth in SEQ ID NO: 20;

(5) VH as set forth in SEQ ID NO: 14 and VL as set forth in SEQ ID NO: 22; or (6) VH as set forth in SEQ ID NO: 14 and VL as set forth in SEQ ID NO: 24.

In the present invention, the above groups (1) to (6) show the amino acid sequences of the heavy chain variable region and light chain variable region of 8D2/8D2(Re), 8D2H1L1, 8D2H2L2, 8D2H3L3, 8D2H2L15, and 8D2H2L17, respectively.

Specifically, the methionine (Met) at position 18 in SEQ ID NO: 6, SEQ ID NO: 10, and SEQ ID NO: 14 is independently substituted with an amino acid selected from the following: Leucine (Leu), Valine (Val), Isoleucine (Ile), or Alanine (Ala).

Therapeutic drugs based on antibodies, especially monoclonal antibodies (MAB) have achieved excellent efficacy in the treatment of several diseases. The traditional method to obtain such therapeutic antibody is immunizing an animal with an antigen, obtaining antibodies against the antigen from the immunized animal, or improving an antibody having low affinity to the antigen by affinity maturation. However, such method is Lime consuming and labor consuming, and often fails to target a specific epitope on the antigen.

Antigen binding is dependent on the variable regions of the light chain and heavy chain; the variable region of each chain comprises three hypervariable regions, also called complementarity determining region (CDR) (the heavy chain (H) comprises HCDR1, HCDR2 and HCDR3, and the light chain (L) comprises LCDR1, LCDR2 and LCDR3; for definition, see Kabat et al., Sequences of Proteins of Immunological Interest, Fifth Edition (1991), Vol. 1-3, NIH Publication 91-3242, Bethesda Md.).

The amino acid sequences of the CDRs in the monoclonal antibody sequences of the embodiments (1) to (6) above were analyzed by technical means well known to those skilled in the art, e.g., by VBASE2 database analysis. The results are provided below.

(1) The amino acid sequences of the 3 CDRs of the heavy chain variable region are shown below:

```
                            (SEQ ID NO: 27)
            HCDR1: GFTFSDNW,
                            (SEQ ID NO: 28)
            HCDR2: IRNKPYNYET,
                            (SEQ ID NO: 29)
            HCDR3: TAQFAY.
```

The amino acid sequences of the 3 CDRs of the light chain variable region are shown below:

```
                            (SEQ ID NO: 30)
            LCDR1: ENIYGG,
                            (SEQ ID NO: 31)
            LCDR2: GAT,
                            (SEQ ID NO: 32)
            LCDR3: QNVLRSPFT.
```

2 The amino acid sequences of the 3 CDRs of the heavy chain variable region are shown below:

```
                            (SEQ ID NO: 27)
            HCDR1: GFTFSDNW,
                            (SEQ ID NO: 28)
            HCDR2: IRNKPYNYET,
                            (SEQ ID NO: 29)
            HCDR3: TAQFAY.
```

The amino acid sequences of the 3 CDRs of the light chain variable region are shown below:

```
                            (SEQ ID NO: 30)
            LCDR1: ENIYGG,
                            (SEQ ID NO: 31)
            LCDR2: GAT,
                            (SEQ ID NO: 32)
            LCDR3: QNVLRSPFT.
```

(3) The amino acid sequences of the 3 CDRs of the heavy chain variable region are shown below:

```
                            (SEQ ID NO: 27)
            HCDR1: GFTFSDNW,
                            (SEQ ID NO: 28)
            HCDR2: IRNKPYNYET,
                            (SEQ ID NO: 29)
            HCDR3: TAQFAY.
```

The amino acid sequences of the 3 CDRs of the light chain variable region are shown below:

```
                            (SEQ ID NO: 30)
            LCDR1: ENIYGG,
                            (SEQ ID NO: 31)
            LCDR2: GAT,
                            (SEQ ID NO: 32)
            LCDR3: QNVLRSPFT.
```

(4) The amino acid sequences of the 3 CDRs of the heavy chain variable region are shown below:

HCDR1: GFTFSDNW, (SEQ ID NO: 27)

HCDR2: IRNKPYNYET, (SEQ ID NO: 28)

HCDR3: TAQFAY. (SEQ ID NO: 29)

The amino acid sequences of the 3 CDRs of the light chain variable region are shown below:

LCDR1: ENIYGG, (SEQ ID NO: 30)

LCDR2: GAT, (SEQ ID NO: 31)

LCDR3: QNVLRSPFT. (SEQ ID NO: 32)

(5) The amino acid sequences of the 3 CDRs of the heavy chain variable region are shown below:

HCDR1: GFTFSDNW, (SEQ ID NO: 27)

HCDR2: IRNKPYNYET, (SEQ ID NO: 28)

HCDR3: TAQFAY. (SEQ ID NO: 29)

The amino acid sequences of the 3 CDRs of the light chain variable region are shown below:

LCDR1: ENIYGG, (SEQ ID NO: 30)

LCDR2: GAT, (SEQ ID NO: 31)

LCDR3: QNVLRSPFT. (SEQ ID NO: 33)

(6) The amino acid sequences of the 3 CDRs of the heavy chain variable region are shown below:

HCDR1:
GFTFSDNW, (SEQ ID NO: 27)

HCDR2:
IRNKPYNYET, (SEQ ID NO: 28)

HCDR3:
TAQFAY. (SEQ ID NO: 29)

The amino acid sequences of the 3 CDRs of the light chain variable region are shown below:

LCDR1:
ENIYGG (SEQ ID NO: 30)

LCDR2:
GAT, (SEQ ID NO: 31)

LCDR3:
QNVLSSRPG. (SEQ ID NO: 34)

The monoclonal antibody or antigen binding fragment thereof according to any one of the embodiments of the present invention, wherein the monoclonal antibody or antigen binding fragment thereof is selected from an Fab, an Fab', an F(ab')$_2$, an Fd, an Fv, a dAb, a complementarity determining region fragment, a single chain antibody (e.g., an scFv), a humanized antibody, a chimeric antibody, or a diabody.

The monoclonal antibody or antigen binding fragment thereof according to any one of the embodiments of the present invention, wherein the monoclonal antibody binds the CTLA4 protein with a $K_D$ less than about $10^{-5}$ M, e.g., less than about $10^{-6}$ M, $10^{-7}$ M, $10^{-8}$ M, $10^{-9}$ M, or $10^{-10}$ M or less.

The monoclonal antibody or antigen binding fragment thereof according to any one of the embodiments of the present invention, wherein the monoclonal antibody comprises non-CDR regions, and said non-CDR regions are from an antibody of a species other than murine, e.g., a human.

The monoclonal antibody or antigen binding fragment thereof of the present invention is an anti-CTLA4 monoclonal antibody or antigen binding fragment thereof that can specifically bind CTLA4.

The monoclonal antibody or antigen binding fragment thereof according to any one of the embodiments of the present invention for use in the prevention and/or therapy and/or adjuvant therapy and/or diagnosis of a tumor; specifically, the tumor is selected from melanoma, kidney tumor/renal tumor, prostate cancer, bladder cancer, colorectal cancer, cancer of gastrointestinal tract, and liver cancer/hepatic cancer.

The monoclonal antibody according to any one of the embodiments of the present invention for use in:
blocking the binding of CTLA4 to B7,
regulating (e.g., down-regulating) the activity of CTLA4 or the level of CTLA4,
relieving the immunosuppression on the body by CTLA4, or
an agent activating T lymphocytes or increasing the expression of IL-2 in T lymphocytes.

Another aspect of the present invention relates to an isolated nucleic acid molecule, which comprises a nucleic acid sequence capable of encoding the heavy chain variable region of an antibody, wherein the heavy chain variable region of the antibody comprises CDRs with the amino acid sequences of SEQ ID NOs: 27-29;

specifically, the heavy chain variable region of the antibody has the amino acid sequence as set forth in SEQ ID NO: 6, SEQ ID NO: 10, SEQ ID NO: 14, or SEQ ID NO: 18; more specifically, the nucleic acid molecule has the nucleotide sequence as set forth in SEQ ID NO: 5, SEQ ID NO: 9, SEQ ID NO: 13, or SEQ ID NO: 17.

The present invention further provides isolated nucleic acid molecules, which encode the monoclonal antibody or antigen binding fragment thereof of the present invention. Such nucleic acid molecules can be isolated from the hybridoma cells, or obtained through recombinant technologies of gene engineering or methods of chemical synthesis.

A further aspect of the present invention relates to an isolated nucleic acid molecule, which comprises a nucleic acid sequence capable of encoding the light chain variable region of an antibodies, wherein the light chain variable region of the antibody comprises
1) CDRs with the amino acid sequences of SEQ ID NOs: 30-32;
2) CDRs with the amino acid sequences of SEQ ID NO: 30, SEQ ID NO: 31 and SEQ ID NO: 33; or
3) CDRs with the amino acid sequences of SEQ ID NO: 30, SEQ ID NO: 31 and SEQ ID NO: 34;
specifically, the light chain variable region of the antibody has the amino acid sequence as set forth in SEQ ID NO: 8, SEQ ID NO: 12, SEQ ID NO: 16, SEQ ID NO: 20, SEQ ID NO: 22, or SEQ ID NO: 24;
more specifically, the nucleic acid molecule has the nucleotide sequence as set forth in SEQ ID NO: SEQ ID NO: 7, SEQ ID NO: 11, SEQ ID NO: 15, SEQ ID NO: 19, SEQ ID NO: 21, or SEQ ID NO: 23.

A further aspect of the present invention relates to a vector, which comprises the isolated nucleic acid molecule according to any one the embodiments of the present invention. The vector of the present invention can be a cloning vector or an expression vector. In a preferred embodiment, the vector of the present invention is, for example, a plasmid, a cosmid, a bacteriophage, a coemid, or the like.

A further aspect of the present invention relates to a host cell, which comprises the isolated nucleic acid molecule of any one of the embodiments of the present invention, or the vector according to the present invention. Such host cells include, but are not limited to, prokaryotic cells such as *E. coli* cells, and eukaryotic cells such as yeast cells, insect cells, plant cells, and animal cells (such as mammalian cells, including mouse cells, human cells, or the like). The cells of the present invention can also be a cell line, such as 293T cells.

A further aspect of the present invention relates to a method of preparing the monoclonal antibody or antigen binding fragment thereof according to any one of the embodiments of the present invention, the method comprising the steps of culturing the host cell of the present invention under suitable conditions and recovering the monoclonal antibody or antigen binding fragment thereof from the cell culture.

A further aspect of the present invention relates to a conjugate, which comprises a monoclonal antibody or antigen binding fragment thereof and a conjugated moiety, wherein the monoclonal antibody is a monoclonal antibody or antigen binding fragment thereof according to any one of the embodiments of the present invention, and the conjugated moiety is a detectable label. Specifically, the conjugated moiety is a radioisotope, a fluorescent substance, a luminescent substance, a chromogenic substance, or an enzyme (e.g., horse radish peroxidase).

A further aspect of the present invention relates to a kit, which comprises the monoclonal antibody or antigen binding fragment thereof according to any one of the embodiments of the present invention, or the conjugate according to the present invention; specifically, the kit further comprises a second antibody, which specifically recognizes said monoclonal antibody or antigen binding fragment thereof; optionally, said second antibody further comprises a detectable label, e.g., a radioisotope, a fluorescent substance, a luminescent substance, a chromogenic substance, or an enzyme (e.g., horse radish peroxidase).

A further aspect of the present invention relates to use of the monoclonal antibody or antigen binding fragment thereof according to any one of the embodiments of the present invention in the preparation of a kit for use in detecting the presence or level of CTLA4 in a sample.

A further aspect of the present invention relates to a pharmaceutical composition, which comprises the monoclonal antibody or antigen binding fragment thereof according to any one of the embodiments of the present invention or the conjugate according to the present invention; optionally, it further comprises a pharmaceutically acceptable carrier and/or excipient.

A further aspect of the present invention relates to use of the monoclonal antibody or antigen binding fragment thereof according to any one of the embodiments of the present invention or the conjugate according to the present invention in the preparation of a medicament for use in the prevention and/or therapy and/or adjuvant therapy and/or diagnosis of a tumor; specifically, the tumor is selected from melanoma, kidney tumor/renal tumor, prostate cancer, bladder cancer, colorectal cancer, cancer of gastrointestinal tract, and liver cancer/hepatic cancer.

A further aspect of the present invention relates to use of the monoclonal antibody or antigen binding fragment thereof according to any one of the embodiments of the present invention or the conjugate according to the present invention in the preparation of a following agent:

an agent that detects the presence or level of CTLA4 in a sample,
an agent that blocks the binding of CTLA4 to B7,
an agent that regulates (e.g., down-regulates) the activity of CTLA4 or the level of CTLA4,
an agent that relieves the immunosuppression on the body by CTLA4.
an agent that activates T lymphocytes, or
an agent that increases the expression of IL-2 in T lymphocytes.

A further aspect of the present invention relates to an in vivo or in vitro method comprising the step of administrating to cells an effective amount of the monoclonal antibody or antigen binding fragment thereof according to any one of the embodiments of the present invention or the conjugate according to the present invention, wherein the method is selected from the following:

a method of detecting the presence or level of CTLA4 in a sample,
a method of blocking the binding of CTLA4 to B7,
a method of regulating (e.g., down-regulating) the activity of CTLA4 or the level of CTLA4,
a method of relieving the immunosuppression on the body by CTLA4,
a method of activating T lymphocytes, or
a method of increasing the expression of IL-2 in T lymphocytes.

Said methods can be used for diagnostic or therapeutic purposes, or non-diagnostic or non-therapeutic purposes (e.g., where the sample is a cell sample, rather than a sample from a patient).

A further aspect of the present invention relates to a method of the prevention and/or therapy and/or adjuvant therapy and/or diagnosis of a tumor, comprising administrating to a subject an effective amount of the monoclonal antibody or antigen binding fragment thereof according to any one of the embodiments of the present invention or the conjugate according to the present invention; specifically, the tumor is selected from melanoma, kidney tumor/renal tumor, prostate cancer, bladder cancer, colorectal cancer, cancer of gastrointestinal tract, and liver cancer/hepatic cancer.

In the present invention, unless stated otherwise, scientific and technical terms used herein have the same meaning as commonly understood by those skilled in the art. Moreover, procedures of cell culture, molecular genetics, nucleic acid chemistry, immunology used herein are the widely utilized methodologies in the relevant art. Meanwhile, for purpose of better understanding the present invention, the definitions and explanations of relevant terms are provided below.

As used herein, when reference is made to the amino acid sequence of the CTLA4 protein (Cytotoxic T-Lymphocyte Antigen 4), it includes the full length of the CTLA4 protein, or the extracellular fragment of CTLA4, CTLA4ECD (SEQ ID NO: 2), or a fragment comprising CTLA4ECD; it also includes a fusion protein of CTLA4ECD, e.g., a fragment fused to the Fc protein fragment of a mouse IgG (mFc) (SEQ ID NO: 3). However, as understood by those skilled in the art, a mutation or variation (including, but not limited to, substitution, deletion and/or addition) may be naturally produced in or artificially introduced into the amino acid sequence of the CTLA4 protein, without affecting its biological functions. Therefore, in the present invention, the term "CTLA4 protein" should include all such sequences, including the sequence as set forth in SEQ ID NO: 2, as well as its native or artificial variants. Furthermore, when reference is made to a sequence fragment of the CTLA4 protein, it not only includes a sequence fragment of SEQ ID NO: 2, but also includes the corresponding sequence fragments of its native or artificial variants.

As used herein, unless specifically stated, B7 refers to B7-1 and/or B7-2; and their specific protein sequences refer to the sequences known in the art. Reference can be made to the sequences disclosed in the literatures of the prior art or GenBank, e.g., B7-1 (CD80, NCBI Gene ID: 941), B7-2 (CD86, NCBI Gene ID: 942).

As used herein, the term $EC_{50}$ refers to concentration for 50% of maximal effect, i.e., the concentration causing 50% of the maximal effect.

As used herein, the term "antibody" refers to an immunoglobulin molecule which generally consists of two pairs of polypeptide chains (each pair has a "light" (L) chain and a "heavy" (H) chain). Antibody light chains can be classified as κ and λ light chain. Heavy chains can be classified as μ, δ, γ, α or ε, and the isotypes of antibody are defined as IgM, IgD, IgG, IgA and IgE, respectively. Within a light chain and heavy chain, a variable region and a constant region are joined via a "J" region of about 12 or more amino acids, and heavy chain further comprises a "D" region of about 3 or more amino acids. Each heavy chain consists of a heavy chain variable region ($V_H$) and a heavy chain constant region ($C_H$). The heavy chain constant region consists of 3 domains ($C_H1$, $C_H2$ and $C_H3$). Each light chain consists of a light chain variable region ($V_L$) and a light chain constant region ($C_L$). The light chain constant region consists of a $C_L$ domain. The constant region of antibody can mediate the binding of the immunoglobulin to host tissues or factors, including various cells of the immune system (e.g., effector cells) and the first component of the classical complement system (C1q). $V_H$ and $V_L$ regions can further be subdivided into regions having high variability (referred to as complementarity determining region (CDR)), interspersed with regions called framework regions (FR) which are relatively conserved. Each $V_H$ or $V_L$ consists of 3 CDRs and 4 FRs, arranged by the following order from the amino terminal to the carboxy terminal: FR1, CDR1, FR2, CDR2, FR3, CDR3, FR4. The variable regions ($V_H$ and $V_L$) of each pair of heavy chain/light chain form an antibody binding site, respectively. The assignment of amino acids to each region or domain follows the definition provided in Kabat, Sequences of Proteins of Immunological Interest (National Institutes of Health, Bethesda, Md. (1987 and 1991)), or Chothia & Lesk (1987) J. Mol. Biol. 196: 901-917; Chothia et al. (1989) Nature 342: 878-883. The term "antibody" is not limited by any specific method for producing the antibody. For example, it includes, particularly, recombinant antibodies, monoclonal antibodies and polyclonal antibodies. Antibodies can be antibodies of different isotypes, e.g., IgG (e.g., IgG1, IgG2, IgG3 or IgG4 subtype), IgA1, IgA2, IgD, IgE or IgM antibodies.

As used herein, the term "antigen binding fragment" of antibody refers to a polypeptide comprising a fragment of a full length antibody, which retains the ability to specifically bind to the antigen bound by the full length antibody, and/or to compete with the full length antibody for specifically binding to the antigen. It is also referred to as "antigen binding portion". Generally, see Fundamental Immunology, Ch. 7 (Paul, W., ed., Second Edition. Raven Press, N.Y. (1989)), which is incorporated herein by reference in the entirety for all purposes. Antigen binding fragments of antibodies can be produced by recombinant DNA technique or enzymatic or chemical cleavage of intact antibodies. In some cases, antigen binding fragments include Fab, Fab', F(ab')$_2$, Fd, Fv, dAb and complementarity determining region (CDR) fragment, single chain antibody (e.g., scFv), chimeric antibody, diabody and such polypeptides which comprises at least a portion of the antibody sufficient to confer the ability of specific antigen binding to the polypeptide.

As used herein, the term "Fd fragment" refers to an antibody fragment consisting of the $V_H$ and $C_H1$ domains; the term "Fv fragment" refers to an antibody fragment consisting of the $V_L$ and $V_H$ domains of a single arm of antibody; the term "dAb fragment" refers to an antibody fragment consisting of the $V_H$ domain (Ward et al., Nature 341: 544-546 (1989)); the term "Fab fragment" refers to an antibody fragment consisting of the $V_L$, $V_H$, $C_L$ and $C_H1$ domains; and the term "F(ab')$_2$ fragment" refers to an antibody fragment comprising two Fab fragments connected by disulfide bridges on the hinge region.

In some cases, the antigen binding fragment of antibody is a single chain antibody (e.g., scFv), wherein the $V_L$ and $V_H$ domains pair to each other via a linker which enables production of a single polypeptide chain to form a monovalent molecule (see, e.g., Bird et al., Science 242: 423-426 (1988) and Huston et al., Proc. Natl. Acad. Sci. USA 85: 5879-5883 (1988)). Such scFv molecule can have the general structure: $NH_2$—$V_L$-Linker-$V_H$-COOH or $NH_2$—$V_H$-Linker-$V_L$-COOH. Suitable linkers from the prior art consist of the repeated GGGGS amino acid sequence or its variants. For example, a linker having the amino acid sequence (GGGGS)$_4$ can be used, but its variants can also be used (Holliger et al. (1993) Proc. Natl. Acad. Sci. USA 90: 6444-6448). Other linkers useful in the present invention are described in Alfthan et al. (1995) Protein Eng. 8: 725-731; Choi et al. (2001) Eur. J. Immunol. 31: 94-106; Hu et al. (1996) Cancer Res. 56: 3055-3061; Kipriyanov et al. (1999) J. Mol. Biol. 293: 41-56 and Roovers et al. (2001) Cancer Immunol.

In some cases, the antigen binding fragment of antibody is a diabody (a bivalent antibody), wherein the $V_H$ and $V_L$ domains are expressed on a single polypeptide chain. However, the linker exploited is too short that the two domains on the same chain cannot pair with each other, and are forced to pair with the complemental domain on another chain. By this way, two antigen binding sites are formed (see, e.g., Holliger P. et al., Proc. Natl. Acad. Sci. USA 90: 6444-6448 (1993) and Poljak R. J. et al., Structure 2: 1121-1123 (1994)).

Antigen binding fragments of antibodies (e.g., the above antibody fragments) can be obtained from given antibodies (e.g., the monoclonal antibodies 4B3, 13A10, 12B9, or 4H4 provided in the present invention) using conventional technologies which are known to those skilled in the art (e.g., recombinant DNA technique or enzymatic or chemical cleavage method), and can be screened for specificity in the same way as that of intact antibodies.

Herein, unless explicitly indicted in the context, when reference is made to the term "antibody", it not only includes intact antibodies, but also includes antigen binding fragments of antibodies.

As used herein, the terms "mAb" or "monoclonal antibody" refers to an antibody or antibody fragment from a population of highly homogenous antibody molecules, i.e., the individual antibodies comprising the population are identical except for possible naturally occurring mutations. Monoclonal antibodies are highly specific to a single epitope on the antigen. In contrast to monoclonal antibodies, polyclonal antibody preparations typically include at least two or more different antibodies recognizing different epitopes on the antigen. Monoclonal antibodies can generally be obtained using the hybridoma technique first described by Kohler et al. (Nature, 256: 495, 1975), or can be obtained using the recombinant DNA technique (see U.S. Pat. No. 4,816,567, for example).

As used herein, a monoclonal antibody mentioned with a number is identical with the monoclonal antibody obtained from a hybridoma mentioned with the same number. For example, the monoclonal antibody 4B3 (or 13A10, 12B9 or 4H4) is identical to the antibody obtained from the hybridoma cell line 4B3 (or 13A10, 12B9 or 4H4) or its subclones or descendent cells.

As used herein, the term "chimeric antibody" refers to such an antibody, in which a portion of the light chain and/or heavy chain is derived from an antibody (which can be derived from a particular species or belong to a particular antibody class or subclass), while another portion of the light chain and/or heavy chain is derived from another antibody (which can be derived from an identical or different species or belong to an identical or different antibody class or subclass), as long as it retains the activity to bind to the target antigen (U.S. Pat. No. 4,816,567 awarded to Cabilly et al.; Morrison et al., Proc. Natl. Acad. Sci. USA, 81: 6851-6855 (1984)).

As used herein, the term "humanized antibody" refers to the antibody or antibody fragment obtained after replacing all or some CDRs of a human immunoglobulin (recipient antibody) with CDRs of a non-human antibody (donor antibody), wherein the donor antibody can be a non-human (e.g., mouse, rat or rabbit) antibody having the desired specificity, affinity or reactivity. Furthermore, some amino acid residues of the framework regions (FRs) of the recipient antibody can be replaced with corresponding amino acid residues of the non-human antibody or amino acid residues of other antibodies so as to further improve or optimize the performance of the antibody. For more details about humanized antibodies, see, e.g., Jones et al., Nature, 321: 522-525 (1986); Reichmann et al., Nature, 332: 323-329 (1988); Presta, Curr. Op. Struct. Biol., 2: 593-596 (1992): and Clark. Immunol. Today 21: 397-402 (2000).

As used herein, a "neutralizing antibody" refers to an antibody or antibody fragment that can remove or significantly reduce the virulence of the target virus (e.g., the ability to infect cells).

As used herein, the term "epitope" refers to the prat on an antigen specifically bound by an immunoglobulin or antibody. In the art, "epitope" is also called "antigenic determinant". An epitope or antigenic determinant generally consists of the chemically active surface groups of the molecule, e.g., amino acid or carbohydrate compounds or sugar side chains, and generally has specific three-dimensional structural characteristics and specific charge characteristics. For example, an epitope generally comprises at least 3, 4, 5, 6, 7, 8, 9, 10, 11, 12, 13, 14, or 15 consecutive or inconsecutive amino acids in a distinct spacial conformation. It can be a "linear" or "conformational" epitope. See, e.g., Epitope Mapping Protocols in Methods in Molecular Biology, Vol. 66, G. E. Morris, Ed. (1996). In a linear epitope, all the points of the interaction between the protein and the interacting molecule (e.g., antibody) are present along the primary amino acid sequence of the protein in a line. In a conformational epitope, the interacting points are present as spanning the amino acid residues of the protein which are separate from each other.

As used herein, the term "isolated" means being obtained from the native state by artificial means. If an "isolated" substance or component occurs in the nature, it is likely that its natural environment has changed, or the substance has been isolated from the natural environment, or both. For example, unisolated polynucleotides or polypeptides naturally occur in a living animal in vivo, and identical polynucleotides or polypeptides of high purity isolated from such natural state are described as "isolated". The term "isolated" does not exclude mixture with artificial or synthetic substances, and does not exclude the presence of other impurities which do not affect the activities of the substance.

As used herein, the term "E. coli expression system" refers to an expression system consisting of E. coli (strain) and the vector, wherein E. coli (strain) is derived from strains commercially available, e.g., but not limited to G1698, ER2566, BL21(DE3), B834(DE3), and BLR(DE3).

As used herein, the term "vector" refers to a nucleic acid carrying tool into which a polynucleotide can be inserted. When a vector enables the expression of the protein encoded by the inserted polynucleotide, the vector is called expression vector. A vector can be introduced into a host cell by transformation, transduction or transfection, such that the genetic substance component carried by the vector is expressed in the host cell. Vectors are well known to those skilled in the art, including, but not limited to: plasmid; phagemid: cosmid: artificial chromosome, e.g., yeast artificial chromosome (YAC), bacterial artificial chromosome (BAC) or P1-derived artificial chromosome (PAC); bacteriophage, e.g., λ phage or M13 phage as well as animal virus, and the like. Animal viruses which can be used as a vector, include, but not limited to, retrovirus (including lentivirus), adenovirus, adeno-associated virus, herpes virus (e.g., herpes simplex virus), poxvirus, baculovirus, papilloma virus, papova virus (e.g., SV40). A vector can comprise several components for controlling the expression, including, but not limited to, promoter sequence, transcription initiation sequence, enhancer sequence, selection component and reporter gene. Moreover, a vector can also comprise replication initiation site.

As used herein, the term "host cell" refers to cells which can be used for introduction of a vector, including, but not limited to, prokaryotic cells such as E. coli or Bacillus

*subtilis*, fungal cells such as yeast cells or *Aspergillus*, insect cells such as S2 *Drosophila* cell or Sf9, or animal cells such as fibroblast, CHO cell, COS cell, NSO cell, HeLa cell, BHK cell, HEK 293 cell or human cell.

As used herein, the term "identity" is used to describe the sequence matching between two polypeptides or between two nucleic acids. When the corresponding positions in two sequences compared are occupied by the same base or amino acid monomer subunit (for example, the corresponding positions in two DNA molecules are both occupied by adenine, or the corresponding positions in two polypeptides are both occupied by lysine), the molecules are identical at that position. The "percent identity" between two sequences is a function of the number of the matching positions shared by these two sequences divided by the number of the positions compared×100. For example, if 6 among 10 positions of two sequences match, these two sequences have 60% identity. For example, DNA sequences CTGACT and CAGGTT share 50% identity (3 among 6 positions match in total). Generally, two sequences are compared after alignment to generate maximal identity. For example, such alignment can be conveniently achieved using a computer program, e.g., the Align program (DNAstar, Inc.), by the method of Needleman et al. (1970) *J. Mol. Biol.* 48: 443-453. Furthermore, the algorithm of E. Meyers and W. Miller (Comput. Appl. Biosci., 4: 11-17 (1988)) incorporated into the ALIGN program (version 2.0) can be used to determine the percent identity between two amino acid sequences, using the PAM120 weight residue table, a Gap length penalty of 12 and a gap penalty of 4. Moreover, the algorithm of Needleman and Wunsch (J Mol Biol. 48: 444-453 (1970)) incorporated into the GAP program of the GCG package (available at www.gcg.com) can be used to determine the percent identity between two amino acid sequences, using the Blossum 62 matrix or PAM250 matrix, a gap weight of 16, 14, 12, 10, 8, 6, or 4 and a length weight of 1, 2, 3, 4, 5, or 6.

As used herein, the term "conservative substitution" refers to amino acid substitutions that do not disadvantageously affect or alter the essential properties of the protein/polypeptide comprising the amino acid sequence. For example, conservative substitutions can be introduced by standard techniques known in the art, such as site-directed mutagenesis and PCR-mediated mutagenesis. Conservative amino acid substitutions include those wherein an amino acid residue is replaced with an amino acid residue having a similar side chain, e.g., a residue similar to the corresponding amino acid residue in terms of physics or function (e.g., having similar size, shape, charge, chemical properties, including the ability to form a covalent bond or hydrogen bond, or the like). Families of amino acid residues having similar side chains have been defined in the art. These families include amino acids having a basic side chain (e.g., lysine, arginine and histidine), an acidic side chain (e.g., aspartic acid and glutamic acid), an uncharged polar side chain (e.g., glycine, asparagine, glutamine, serine, threonine, tyrosine, cysteine, and tryptophan), a non-polar side chain (e.g., alanine, valine, leucine, isoleucine, proline, phenylalanine, and methionine), a beta-branched side chain (e.g., threonine, valine and isoleucine), and an aromatic side chain (e.g., tyrosine, phenylalanine, tryptophan, and histidine). Thus, it is preferred to replace the corresponding amino acid residue with another amino acid residue from the same side chain family. Methods of identifying amino acid conservative substitutions are well known in the art (see, e.g., Brummell et al., Biochem., 32: 1180-1187 (1993); Kobayashi et al., Protein Eng. 12(10): 879-884 (1999); and Burks et al., Proc. Natl. Acad. Sci. USA, 94: 412-417 (1997), which are incorporated herein by reference).

As used herein, the term "immunogenicity" refers to the ability to stimulate the body to generate specific antibodies or sensitize lymphocytes. It not only refers to the properties of the antigen which can stimulate specific immune cells so as to induce activation, proliferation and differentiation of the immune cells, and ultimately production of immune effector substances such as antibodies, and can sensitize lymphocytes, but also refers to the specific immune responses by the body's immune system to produce antibodies or sensitize T lymphocytes after the stimulation of the body by the antigen. Immunogenicity is the most important property of the antigen. Whether an antigen can successfully induce immune response in a host depends on three factors: the nature of the antigen, the reactivity of the host and the manner of immunization.

As used herein, the term "specific binding" refers to the non-random binding reaction between two molecules, such as the reaction between an antibody and its targeted antigen. In some embodiments, an antibody specifically binding an antigen (or an antibody specific for an antigen) means the antibody binds the antigen with an affinity ($K_D$) less than about $10^{-5}$ M, e.g., less than about $10^{-6}$ M, $10^{-7}$ M, $10^{-8}$ M, $10^{-9}$ M, or $10^{-10}$ M or less.

As used herein, the term "$K_D$" refers to the dissociation equilibration constant of a particular antibody-antigen interaction, which is used to describe the binding affinity between the antibody and the antigen. The less the equilibration dissociation constant is, the tighter the antibody-antigen binding is and the higher the affinity between the antibody and antigen is. Generally, an antibody (e.g., the monoclonal antibodies 4B3, 13A10, 12B9, or 4H4 of the present invention) binds the antigen (e.g., the L1 protein) with a dissociation equilibration constant ($K_D$) less than about $10^{-5}$ M, e.g., less than about $10^{-6}$ M, $10^{-7}$ M, $10^{-8}$ M, $10^{-9}$ M, or $10^{-10}$ M or less, e.g., as determined using Surface Plasmon Resonance (SPR) on a BIACORE instrument.

As used herein, the terms "monoclonal antibody" and "mAb" have the same meaning, and can be used interchangeably. Also, the terms "polyclonal antibody" and "pAb" have the same meaning, and can be used interchangeably. Again, the terms "polypeptide" and "protein" have the same meaning, and can be used interchangeably. Furthermore, in the present invention, amino acids are generally represented by single-letter or three-letter abbreviations well known in the art. For example, alanine can be represented by A or Ala.

As used herein, the terms "hybridoma" and "hybridoma cell line" can be used interchangeably. Moreover, when reference is made to the term "hybridoma" or "hybridoma cell line", it also comprises the subclones and descendent cells of the hybridoma. For example, when reference is made to the hybridoma cell line 4B3, it also comprises the subclones and descendent cells of the hybridoma cell line 4B3.

As used herein, the term "pharmaceutically acceptable vector and/or excipient" refers to vector and/or excipient compatible to the subject and the active component in pharmacology and/or physiology, which are well known in the art (see, e.g., Remington's Pharmaceutical Sciences. Edited by Gennaro A R, 19th ed. Pennsylvania: Mack Publishing Company, 1995), and include but not limited to: pH adjusting agent, surfactant, adjuvant, ionic intensity enhancer. For example, pH adjusting agent includes but not limited to phosphate buffer, surfactant includes but not limited to cationic, anionic or nonionic surfactant, e.g., Tween-80; and ionic intensity enhancer includes but not limited to sodium chloride.

As used herein, the term "adjuvant" refers to non-specific immune enhancer, which can enhance the immune response of the body to the antigen or change the type of the immune response when delivered together with an antigen or in advance into the body. There are many adjuvants, including but not limited to aluminum adjuvant (e.g., aluminum hydroxide), Freund's adjuvant (e.g., complete Freund's adjuvant and incomplete Freund's adjuvant), *Corynebacterium parvum*, lipopolysaccharide, cytokine, and the like. Freund's adjuvant is the most commonly used one in animal trials at present, and aluminum hydroxide is the widely used one in clinical experiments.

As used herein, the term "effective amount" refers to an amount sufficient to achieve or at least partially achieve the desired effects. For example, prophylactically effective amount for a disease (e.g., a disease associated with excessive binding of CTLA4 to B7 or CTLA4 activity such as tumor) refers to an amount sufficient to prevent, arrest, or delay the development of a disease (e.g., a disease associated with excessive binding of CTLA4 to B7 or CTLA4 activity such as tumor); and therapeutically effective amount for a disease refers to an amount sufficient to cure or at least partially arrest a disease and its complications in a patient suffering from the disease. It is well within the skills of those skilled in the art to determine such effective amount. For example, a therapeutically effective amount will depend on the severity of the disease to be treated, the general status of the immune system of the patient, the general status of the patient, e.g., age, body weight and sex, administration mode of the agent, other therapies administrated simultaneously, and the like.

Beneficial Effects of the Invention

The monoclonal antibody 8D2 and its humanized antibodies of the present invention can specifically bind to CTLA4 very well. Among them, the antibodies 8D2 and 8D2(Re) bind to the murine CTLA4 antigen at a binding efficiency better than the control antibodies 10D1 (Alan J. Korman, Edward L. Halk, et al., HUMAN CTLA-4 ANTIBODIES, U.S. Pat. No. 6,984,720 B1) and 11.2.1 (Douglas Charles Hanson, Mark Joseph Neveu, et al., Human monoclonal antibodies to CTLA-4, U.S. Pat. No. 682,736 B1). The humanized antibody 8D2H1L1 binds to the murine CTLA4 antigen at a binding efficiency better than the control antibody 10D1, and comparable to 11.2.1. The humanized antibody 8D2H2L2 binds to the human CTLA4 antigen at a binding efficiency comparable to 10D1. The humanized antibodies 8D2H2L2 and 8D2H3L3 bind to the monkey CTLA4 antigen at a binding efficiency comparable to 10D1. The antibodies 8D2H2L15 and 8D2H2L17 bind to the human CTLA4 antigen at a binding efficiency better than the control antibodies 10D1 and 11.2.1.

The antibodies 8D2, 8D2(Re), and the 8D2 humanized antibodies 8D2H1L1, 8D2H2L2, 8D2H3L3, 8D2H2L15, and 8D2H2L17 can compete with B7 for binding to the antigen CTLA4. Among them, 8D2, 8D2(Re), 8D2H1L1, and 8D2H2L2 are stronger than 10D1 in competing with B7-2 for binding to CTLA4; and 8D2H1L1, 8D2H2L2, 8D2H3L3, 8D2H2L15, and 8D2H2L17 are all stronger than the antibodies 10D1 and 11.2.1 in competing with B7-1 and B7-2 for binding to CTLA4.

The monoclonal antibody 8D2 and its humanized antibodies of the present invention can block the binding of CLTA4 to B7, specifically relieve the immunosuppression on the body by CTLA4, and activate T lymphocytes very effectively. Among them, 8D2H2L2 and 8D2H2L15 are stronger than the control antibodies 10D1 and 11.2.1 in activating T lymphocytes.

BRIEF DESCRIPTION OF THE DRAWINGS

FIG. 15. The $EC_{50}$ results of the binding of 8D2H3L3 to the labeled 293F-CTLA4 cells.

FIG. 16. Determination of the binding of the antibodies 8D2, 8D2H1L1, and 8D2(Re) and control antibodies 10D1 and 11.2.1 to CTLA4 using the ELISA method.

FIG. 19. Determination of the binding of the recombinant antibodies 8D2H2L2(20150327), 8D2H2L15, 8D2H2L17, and 8D2H2L2 (20140422) and control antibodies 10D1 and 11.2.1 to monkey CTLA4 using the ELISA method.

FIG. 20. Results of ELISA for competition of the antibodies 8D2H1L1 and control antibodies 10D1 and 11.2.1 with B7-1.

SPECIFIC EMBODIMENTS

Figure 1:
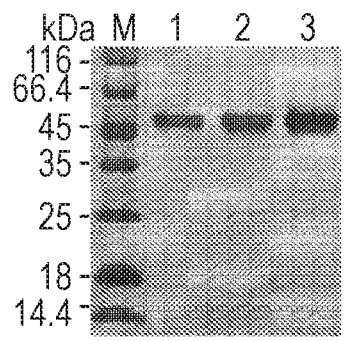
FIG. 1. Results of SDS-PAGE of the CTLA4ECD-mFc fusion protein. The samples and their loading amounts in the 4 lanes, from left to right, were: M, Marker, 10 µL; CTLA4ECD-mFc fusion protein. 1 µg; CTLA4ECD-mFc fusion protein, 2 µg; CTLA4ECD-mFc fusion protein. 3 µg.

The embodiments of the invention will be described below in details with reference to the Examples. Those skilled in the art will understand that the following Examples are provided merely to illustrate the invention. They should not be construed, whatsoever, as to limit the scope of the invention. Examples, for which specific techniques or conditions are not described, were performed using the techniques or conditions disclosed in the literatures of the art (e.g., written by J. Sambrook et al., translated by Peitang HUANG et al., Molecular Cloning: A Laboratory Manual, Third Edition, Science Press) or following the instructions provided with the products. Reagents and instruments, for which the supplier is not indicated, are conventional products which are commercially available.

In the following Examples of the invention, the BALB/C mice were purchased from Guangdong Medical Laboratory Animal Center.

In the following Examples of the invention, the T cells used were obtained from Akeso Biopharma Inc., Zhongshan.

The control antibody. 10D1, was prepared according to U.S. Pat. No. 6,984,720 B1; and 11.2.1 according to U.S. Pat. No. 6,682,736 B1.

Example 1. Generation of the CTLA4-8D2 Hybridoma Cell Line LT001 and Preparation of the Monoclonal Antibody 8D2

Recombinant CTLA4 was expressed in a mammalian cell expression system for immunizing mice as antigen, and hybridoma cells were obtained by fusing mouse spleen cells with myeloma cells. A hybridoma cell line (the CTLA4-8D2 hybridoma cell line LT001) was obtained after screening a great number of samples. Said cell line could secret the monoclonal antibody 8D2, which specifically binds CTLA4. The specific methods are described below.

1. Synthesis of the CTLA4ECD-mFc Gene

According to the design (SEQ ID NO: 3), the amino acid sequence (SEQ ID NO: 2) corresponding to the extracellular fragment of the CTLA4 gene (Cytotoxic T-Lymphocyte Antigen 4, NCBI Gene ID: 1493, SEQ ID NO: 1) (CTLA4ECD) was fused to the Fc protein fragment of mouse IgG (mFc), wherein mFc refers to the Fc protein fragment of mouse IgG with the amino acid sequence as shown by the underlined part of SEQ ID NO: 3.

In order to increase the expression efficiency of the gene of interest in the 293f cell expression system, the nucleic acid sequence encoding the SEQ ID NO: 3 protein sequence was optimized at Genscript Co., mainly taking the factors such as codon preference, GC content, secondary structures of mRNA, and repeated sequences into consideration. The final optimized gene encoding the CTLA4ECD-mFc fusion protein has the following sequence (SEQ ID NO: 4), and was synthesized at Genscript Co.

The sequence of the CTLA4ECD gene (375 bp):

(SEQ ID NO: 1)
GCAATGCACGTGGCCCAGCCTGCTGTGGTACTGGCCAGCACCCGAGGCATC

GCCAGCTTTGTGTGTGAGTATGCATCTCCAGGCAAAGCCACTGAGGTCCGG

GTGACAGTGCTTCGGCAGGCTGACAGCCAGGTGACTGAAGTCTGTGCGGCA

ACCTACATGATGGGGAATGAGTTGACCTTCCTAGATGATTCCATCTGCACG

GGCACCTCCAGTGGAAATCAAGTGAACCTCACTATCCAAGGACTGAGGGCC

ATGGACACGGGACTCTACATCTGCAAGGTGGAGCTCATGTACCCACCGCCA

TACTACCTGGGCATAGGCAACGGAACCCAGATTTATGTAATTGATCCAGAA

CCGTGCCCAGATTCTGAC

The sequence of the protein encoded by CTLA4ECD (125 aa):

(SEQ ID NO: 2)
AMHVAQPAVVLASSRGIASFVCEYASPGKATEVRVTVLRQADSQVTEVCAA

TYMMGNELTFLDDSICTGTSSGNQVNLTIQGLRAMDTGLYICKVELMYPPP

YYLGIGNGTQIYVIDPEPCPDSD

The sequence of the CTLA4ECD-mFc fusion protein (364 aa):
wherein the CTLA4ECD portion is underlined with a waving line, and the mFc portion is underlined with a solid line.

(SEQ ID NO: 3)
AMHVAQPAVVLASSRGIASFVCEYASPGKATEVRVTVLRQADS

QVTEVCAATYMMGNELTFLDDSICTGTSSGNQVNLTIQGLRAMDT

GLYICKVELMYPPPYYLGIGNGTQIYVIDPEPCPDSDENLYFQGPRG

PTIKPCPPCKCPAPNLLGGPSVFIFPPKIKDVLMISLSPIVTCVVVDVS

EDDPDVQISWFVNNVEVHTAQTQTHREDYNSTLRVVSALPIQHQD

WMSGKEFKCKVNNKDLPAPIERTISKPKGSVRAPQVYVLPPPEEEM

TKKQVTLTCMVTDFMPEDIYVEWTNNGKTELNYKNTEPVLDSDGS

YFMYSKLRVEKKNWVERNSYSCSVVHEGLHNHHTTKSFSRTPGK

The coding sequence of the gene corresponding to the CTLA4ECD-mFc fusion protein (1092 bp):
wherein the CTLA4ECD portion is underlined with a waving line, and the mFc portion is underlined with a solid line.

(SEQ. ID NO: 4)
GCAATGCATGTCGCACAGCCTGCAGTGGTCCTGGCAAGCTC

CAGGGGAATCGCTAGCTTCGTGTGCGAATACGCTTCCCCAGGCA

AGGCAACCGAGGTCCGGGTGACAGTCCTGAGACAGGCCGACAG

CCAGGTGACAGAAGTCTGCGCCGCTACTTATATGATGGGCAACG

AGCTGACCTTTCTGGACGATAGCATTTGTACCGGGACATCTAGT

GGAAACCAAGTGAATCTGACCATCCAGGGCCTGCGCGCTATGG

ACACAGGGCTGTACATTTGTAAAGTGGAGCTGATGTATCCCCCT

CCATACTATCTGGGAATCGGCAACGGGACCCAGATCTACGTGAT

TGATCCTGAACCATGCCCCGACTCCGATGAGAATCTGTATTTCC

AGGGACCACGAGGCCCCACAATTAAGCCATGTCCCCCTTGCAAA

TGTCCTGCACCAAACCTGCTGGGAGGACCAAGCGTGTTCATCTT

TCCACCCAAGATCAAGGACGTGCTGATGATCTCACTGAGCCCCA

TTGTGACCTGCGTGGTCGTGGACGTGAGCGAGGACGATCCTGA

TGTGCAGATCAGTTGGTTCGTCAACAATGTGGAAGTCCACACAG

CTCAGACTCAGACCCATAGGGAGGATTACAATAGTACTCTGCGC

GTCGTGTCAGCACTGCCCATTCAGCACCAGGACTGGATGAGCG

GCAAGGAGTTCAAGTGCAAAGTGAACAACAAGGATCTGCCCGC

ACCTATCGAGAGAACTATTTCCAAGCCTAAAGGGTCTGTGAGGG

CCCCACAGGTGTATGTCCTGCCTCCACCCGAGGAAGAGATGACT

AAGAAACAGGTGACACTGACTTGTATGGTCACCGACTTCATGCC

CGAAGATATCTACGTGGAGTGGACTAACAATGGGAAGACCGAA

CTGAACTATAAAAATACAGAGCCTGTGCTGGACTCAGATGGAAG

CTACTTTATGTATAGCAAGCTGCGAGTGGAAAAGAAAAACTGGG

TCGAGCGGAACAGCTACTCTTGTAGTGTGGTCCACGAAGGGCTG

CATAATCACCACACCACTAAATCATTCTCCCGAACTCCAGGCAA

A

2. Generation of the pUC57simple-CTLA4ECD-mFc Plasmid

The synthesized CTLA4ECD-mFc fusion gene (SEQ ID NO: 4) was cloned into the pUC57simple expression vector (provided by Genscript Co.) at Genscript Co., resulting in the pUC57simple-CTLA4ECD-mFc plasmid.

3. Construction of the pcDNA3.1-CTLA4ECD-mFc Recombinant Plasmid

The pUC57simple-CTLA4ECD-mFc plasmid was digested with the endonucleases Xba I and BamH I. The CTLA4ECD-mFc fusion gene fragment was recovered via electrophoresis and was ligated into the pcDNA3.1 expression vector (purchased from Invitrogen Co.). The resultant pcDNA3.1-CTLA4ECD-mFc plasmid was used to transfect the competent cells of the DH5a strain of *E. coli* (purchased from TIANGEN Co.). Transfection and culture were performed following the instructions. *E. coli* colonies positive for pcDNA3. I-CTLA4ECD-mFc were screened out and propagated following conventional methods. Then, the pcDNA3.1-CTLA4ECD-mFc recombinant plasmid was extracted using a kit (purchased from Tiangen Biotech (Beijing) Co. LTD, DP103-03) following the instructions provided with the kit.

4. Cells of 293F (purchased from Invitrogen Co.) were transfected with the pcDNA3.1-CTLA4ECD-mFc recombinant plasmid using the lipofectamin transfection kit (purchased from Invitrogen Co.).

5. Seven days after transfecting 293F cells with the pcDNA3, 1-CTLA4ECD-mFc recombinant plasmid, the CTLA4ECD-mFc fusion protein was purified from the culture liquid by high speed centrifugation, vacuum filtration through a microporous filter membrane, and HiTrap protein A HP column chromatography. After purification, samples were taken, added into the reductive loading buffer for protein electrophoresis, and examined by SDS-PAGE electrophoresis. As shown in FIG. 1, the protein of interest is shown as a band at about 45 kD.

6. Generation of the CTLA4-8D2 Hybridoma Cell Line LT001

Using the CTLA4ECD-mFc fusion protein as the antigen, hybridoma cells were obtained by fusing the splenic cells from the immunized BALB/C mice (purchased from Guangdong Medical Laboratory Animal Center) with mouse myeloma cells following an established method (e.g., Stewart, S. J., "Monoclonal Antibody Production", in Basic Methods in antibody Production and Characterization, Eds. G. C. Howard and D. R. Bethell, Boca Raton: CRC Press, 2000).

CTLA4 was used as the antigen to coat an ELISA plate, and hybridoma cells secreting novel antibodies specifically binding to CTLA4 were obtained by an indirect ELISA screening. Hybridoma cell lines secreting monoclonal antibodies which competed with the ligand B7-1 (CD80, NCBI Gene ID: 941) or B7-2 (CD86, NCBI Gene ID: 942) for binding to CTLA4 were obtained by a competitive ELISA screening from the hybridoma cells obtained in the indirect ELISA screening. A stable hybridoma cell line was obtained via limited dilution. The hybridoma cell line was designated as the CTLA4-8D2 hybridoma cell line, and the CTLA4-8D2 stable cell line was obtained via limited dilution (also referred to as LT001 in the present invention; the monoclonal antibody secreted by it was designated as 8D2).

7. Preparation of the Antibody 8G2

The CTLA4-8D2 (LT001) cell line of the present invention was cultured in a medium supplemented with 10% fetal bovine serum with low IgG. Seven days later, the supernatant of the cell culture was collected to purify the antibody 8D2.

8. Detection of the 8D2 Antibody by SDS-PAGE

Figure 2:
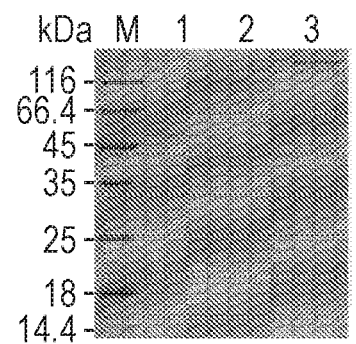
FIG. 2. Results of SDS-PAGE of the 8D2 antibody. The samples and their loading amounts in the 4 lanes, from left to right, were: M, marker, 10 µL; an antibody sample in the reductive loading buffer for protein electrophoresis, 0.3 µg; the non-reductive loading buffer for protein electrophoresis, 2 µL: an antibody sample in the non-reductive loading buffer for protein electrophoresis, 0.3 µg.

Purified samples were added into the reductive loading buffer for protein electrophoresis and the non-reductive loading buffer for protein electrophoresis. After boiling, detection was performed. The results show that the protein of interest is shown as two band at about 50 kD and 25 kD for the reductive protein sample, or as a band at about 150 kD for the non-reductive protein sample (FIG. 2).

Example 2. Determination of the Light Chain and Heavy Chain Sequences of the Monoclonal Antibody 8D2

Following the instructions of the Cultured Cell/Bacteria Total RNA Extraction Kit (Tiangen, Cat. No. DP430), mRNA was extracted from the CTLA4-8D2 hybridoma cell line (LT001 cell) generated in Example 1.

Following the instructions of the Invitrogen SuperScript® III First-Strand Synthesis System for RT-PCR kit, cDNA was synthesized and amplified by PCR. The PCR amplication product was immediately subjected to TA cloning, following the instructions of the pEASY-TI Cloning Kit (TransGen, Cat. No. CT101). The product of TA cloning was immediately subjected to sequencing, and the sequencing results are provided below.

The results of DNA sequencing of the heavy chain variable region (345 bp):

(SEQ ID NO: 5)
GAGGTGAAACTGGACGAAACTGGCGGGGGGCTGGTGCAGCCCGGACGACCT

ATGAAGCTGTCATGCGTCGCCAGCGGCTTCACCTTTAGCGACAACTGGATG

AATTGGGTGAGGCAGAGCCCAGAGAAGGGGCTGGAATGGCTGGCTCAGATC

CGCAACAAACCCTACAATTATGAGACCTACTATTCTGACAGTGTGAAGGGC

CGGTTCACAATTTCCAGAGACGATTCTAAAAGCTCCGTCTACCTGCAGATG

AACAATCTGAGAGGCGAAGATATGGGGATCTACTATTGCACAGCACAGTTC

GCTTATTGGGGACAGGGCACTCTGGTCACAGTCTCCGCC

The protein sequence encoded by it (115 aa):

(SEQ ID NO: 6)
EVKLDETGGGLVQPGRPMKLSCVASGFTFSDNWMNWVRQSPEKGLEWLAQI

RNKPYNYETYYSDSVKGRFTISRDDSKSSVYLQMNNLRGEDMGIYYCTAQF

AYWGQGTLVTVSA

The results of DNA sequencing of the light chain variable region (318 bp):

(SEQ ID NO: 7)
GACATTCAGATGACACAGAGTCCTGCTTCCCTGAGTGCCTCAGTGGGGGAG

ACCGTCACAATCACTTGCGGCACCTCTGAAAACATCTACGGCGGGCTGAAT

TGGTATCAGCGGAAGCAGGGCAAAAGTCCCCAGCTGCTGATCTTCGGAGCA

ACAAACCTGGCCGACGGCATGAGCTCCCGGTTTAGCGGGTCCGGATCTGGC

AGACAGTACAGCCTGAAGATTTCTAGTCTGCACCCAGACGATGTGGCTACT

TACTATTGCCAGAATGTCCTGAGGAGTCCCTTCACCTTTGGGTCAGGAACA

AAGCTGGAGATC

The protein sequence encoded by it (106 aa):

(SEQ ID NO: 8)
DIQMTQSPASLSASVGETVTITCGTSENIYGGLNWYQRKQGKSPQLLIFGA

TNLADGMSSRFSGSGSGRQYSLKISSLHPDDVATYYCQNVLRSPFTFGSGT

KLEI

Example 3. Design of the Light Chain and Heavy Chain Sequences of the Humanized Antibodies 8D2H1L1, 8D2H2L2, 8D2H3L3, 8D2H2L15 and 8D2H2L17

Based on the three-dimensional crystal structure of the CTLA4 protein (Nat. Struct. Biol. (1997) 4, p. 527) and the sequences of the 8D2 antibody obtained in Example 2, the structure of the antibody was modeled on computer. The variable region sequences of the antibodies 8D2H1L1, 8D2H2L2, 8D2H3L3, 8D2H2L15 and 8D2H2L17 were designed based on the antibody sequences and the structural model (the constant region sequences of the antibodies were from the NCBI database). The variable region sequences are provided below.

1. The Light Chain and Heavy Chain Sequences of the Monoclonal Antibody 8D2H1L1

The DNA Sequence of the Heavy Chain Variable Region (345 bp):

(SEQ ID NO: 9)
GAAGTGCAGCTGGTCGAGTCCGGGGGGGGCCTGGTGCAGCCAGGAGGATCA

ATGCGACTGAGCTGCGCCGCCTTCCGGCTTCACCTTCAGCGACAACTGGATG

```
AATTGGGTCAGGCAGGCACCAGGAAAGGGACTGGAGTGGCTGGCACAGATC

CGCAACAAACCTTACAACTACGAAACTTACTACAGCGACTCCGTGAAGGGG

CGGTTCACCATTTCTAGAGACGATTCTAAAAACAGTGTGTACCTGCAGATG

AATAGCCTGAAGACCGAGGATACAGGAGTCTACTATTGTACCGCACAGTTT

GCTTATTGGGGGCAGGGCACTCTGGTGACAGTCTCTTCA
```

The Protein Sequence Encoded by it (115 Aa):

(SEQ ID NO: 10)
```
EVQLVESGGGLVQPGGSMRLSCAASGFTFSDNWMNWVRQAPGKGLEWLAQI
RNKPYNYETYYSDSVKGRFTISRDDSKNSVYLQMNSLKTEDTGVYYCTAQF
AYWGQGTLVTVSS
```

The DNA Sequence of the Light Chain Variable Region (321 bp):

(SEQ ID NO: 11)
```
GACATTCAGATGACTCAGAGCCCTTCAAGCCTGTCCGCATCTGTGGGCGAC

CGAGTCACCATCACATGCAGAACCTCCGAGAACATCTACGGCGGGCTGAAT

TGGTATCAGCGAAAGCAGGGGAAAAGTCCCAAGCTGCTGATCTACGGGCA

ACAAACCTGGCCAGCGGAATGAGCTCCAGATTCAGTGGATCAGGCAGCGGG

ACAGATTATACTCTGAAAATTTCTAGTCTGCACCCAGACGATGTGGCAACC

TACTATTGCCAGAATGTCCTGAGGTCACCCTTCACCTTTGGAAGCGGCACA

AAACTGGAGATCAAG
```

The Protein Sequence Encoded by it (107 Aa):

(SEQ ID NO: 12)
```
DIQMTQSPSSLSASVGDRVTITCRTSENIYGGLNWYQRKQGKSPKLLIYGA
TNLASGMSSRFSGSGSGTDYTLKISSLHPDDVATYYCQNVLRSPFTFGSGT
KLEIK
```

2. The Light Chain and Heavy Chain Sequences of the 8D2 Humanized Monoclonal Antibody 8D2H2L2

The DNA Sequence of the Heavy Chain Variable Region (345 bp):

(SEQ ID NO: 13)
```
GAAGTGCAGCTGGTCGAGTCCGGGGGGGCCTGGTGCAGCCAGGAGGATCA

ATGCGACTGAGCTGCGCCGCTTCCGGCTTCACCTTCAGCGACAACTGGATG

AATTGGGTCAGGCAGGCACCAGGAAAGGGACTGGAGTGGCTGGCACAGATC

CGCAACAAACCTTACAACTACGAAACTTACTACAGCGCCTCCGTGAAGGGG

CGGTTCACCATTTCTAGAGACGATTCTAAAAACAGTGTGTACCTGCAGATG

AATAGCCTGAAGACCGAGGATACAGGAGTCTACTATTGTACCGCACAGTTT

GCTTATTGGGGGCAGGGCACTCTGGTGACAGTCTCTTCA
```

The Protein Sequence Encoded by it (115 Aa):

(SEQ ID NO: 14)
```
EVQLVESGGGLVQPGGSMRLSCAASGFTFSDNWMNWVRQAPGKGLEWLAQI
RNKPYNYETYYSASVKGRFTISRDDSKNSVYLQMNSLKTEDTGVYYCTAQF
AYWGQGTLVTVSS
```

The DNA Sequence of the Light Chain Variable Region (321 bp):

(SEQ ID NO: 15)
```
GACATTCAGATGACTCAGAGCCCTTCAAGCCTGAGTGCCTCATCTACGGCG

GCCTGAACTGGTATCAGCGAAAGCCAGGCAAGAGCCCCAAGCTGCTGATCT

ACGGGGCAACCAACCTGGCCTCTGGAGTGAGCTCCAGATTCAGCGGCAGCG

GCTCTGGGACCGACTATACTCTGACCATTTCTAGTCTGCAGCCTGAAGATG

TGGCAACATACTATTGCCAGAATGTCCTGAGGTCCCCATTCACCTTTGGAT

CTGGCACCAAGCTGGAGATCAAG
```

The Protein Sequence Encoded by it (107 Aa):

(SEQ ID NO: 16)
```
DIQMTQSPSSLSASVGDRVTITCRTSENIYGGLNWYQRKPGKSP
KLLIYGATNLASGVSSRFSGSGSGTDYTLTISSLQPEDVATYYCQNV
LRSPFTFGSGTKLEIK
```

3. The Light Chain and Heavy Chain Sequences of the 8D2 Humanized Monoclonal Antibody 8D2H3L3

The DNA Sequence of the Heavy Chain Variable Region (345 bp):

(SEQ ID NO: 17)
```
GAGGTGCAGCTGGTCGAGTCTGGAGGCGGCCTGGTGCAGC

CCGGCGGGTCACTGCGACTGAGCTGCGCCGCTTCCGGCTTCAC

CTTCAGCGACAACTGGATGAATTGGGTGAGGCAGGCACCCGGG

AAGGGGCTGGAGTGGGTCGCTCAGATCCGCAACAAACCTTACA

ATTATGAGACAGAATACGCAGCCTCTGTGAAGGGGCGGTTCACT

ATTAGTAGAGACGATAGCAAGAACAGCGCCTATCTGCAGATGAA

TAGCCTGAAGACCGAAGATACAGCCGTCTACTATTGTACAGCTC

AGTTTGCATACTGGGGCCAGGGAACTCTGGTGACCGTCAGCTCC
```

The Protein Sequence Encoded by it (115 aa):

(SEQ ID NO: 18)
```
EVQLVESGGGLVQPGGSLRLSCAASGFTFSDNWMNWVRQAPG
KGLEWVAQIRNKPYNYETEYAASVKGRFTISRDDSKNSAYLQMNSL
KTEDTAVYYCTAQFAYWGQGTLVTVSS
```

The DNA Sequence of the Light Chain Variable Region (321 bp):

(SEQ ID NO: 19)
```
GACATTCAGATGACTCAGAGCCCTTCTTCTCTGTCCGCATCT

GTGGGAGACCGGGTCACCATCACATGCAGAGCCAGCGAGAACA

TCTACGGCGGCCTGAACTGGTATCAGCAGAAGCCAGGCAAAGC

TCCCAAGCTGCTGATCTACGGAGCAACCTCCCTGGCATCTGGAG

TGCCATCCCGGTTCAGTGGATCAGGCAGCGGGACCGACTATACT
```

-continued

```
CTGACCATTAGCTCCCTGCAGCCTGAAGACTTCGCCACATACTA

TTGCCAGAACGTGCTGAGGTCCCCATTCACCTTTGGATCTGGCA

CCAAGCTGGAGATCAAG
```

The Protein Sequence Encoded by it (107 Aa):

```
                                  (SEQ ID NO: 20)
DIQMTQSPSSLSASVGDRVTITCRASENIYGGLNWYQQKPGKA

PKLLIYGATSLASGVPSRFSGSGSGTDYTLTISSLQPEDFATYYCQNV

LRSPFTFGSGTKLEIK
```

4. The Light Chain and Heavy Chain Sequences of the 8D2 Humanized Monoclonal Antibody 8D2H2L15

The DNA Sequence of the Heavy Chain Variable Region (345 bp):

```
                                  (SEQ ID NO: 13)
GAAGTGCAGCTGGTCGAGTCCGGGGGGGGCCTGGTGC

AGCCAGGAGGATCAATGCGACTGAGCTGCGCCGCTTCCGG

CTTCACCTTCAGCGACAACTGGATGAATTGGGTCAGGCAGG

CACCAGGAAAGGGACTGGAGTGGCTGGCACAGATCCGCAA

CAAACCTTACAACTACGAAACTTACTACAGCGCCTCCGTGA

AGGGGCGGTTCACCATTTCTAGAGACGATTCTAAAAACAGT

GTGTACCTGCAGATGAATAGCCTGAAGACCGAGGATACAGG

AGTCTACTATTGTACCGCACAGTTTGCTTATTGGGGGCAGG

GCACTCTGGTGACAGTCTCTTCA
```

The Protein Sequence Encoded by it (115 Aa):

```
                                  (SEQ ID NO: 14)
EVQLVESGGGLVQPGGSMRLSCAASGFTFSDNWMNWVR

QAPGKGLEWLAQIRNKPYNYETYYSASVKGRFTISRDDSKNSV

YLQMNSLKTEDTGVYYCTAQFAYWGQGTLVTVSS
```

The DNA Sequence of the Light Chain Variable Region (321 bp):

```
                                  (SEQ ID NO: 21)
GACATCCAGATGACTCAGTCTCCCAGCTCCCTGTCCGC

TTCTGTGGGCGATCGGGTCACTATCACCTGTAGAACCAGCG

AGAACATTTACGGCGGACTGAATTGGTATCAGAGGAAGCCC

GGGAAAAGTCCTAAGCTGCTGATCTACGGAGCAACAAACCT

GGCCTCCGGCGTGTCTAGTCGCTTCAGTGGATCAGGCAGCG

GGACCGACTATACACTGACTATTTCAAGCCTGCAGCCAGAG

GATGTGGCCACATACTATTGCCAGAATGTCCTGAGCCGGCA

CCCCGGATTTGGCTCAGGGACCAAACTGGAAATTAAG
```

The Protein Sequence Encoded by it (107 Aa):

```
                                  (SEQ ID NO: 22)
DIQMTQSPSSLSASVGDRVTITCRTSENIYGGLNWYQRKP

GKSPKLLIYGATNLASGVSSRFSGSGSGTDYTLTISSLQPEDVAT

YYCQNVLSRHPGFGSGTKLEIK
```

5. The Light Chain and Heavy Chain Sequences of the 8D2 Humanized Monoclonal Antibody 8D2H2L17

The DNA Sequence of the Heavy Chain Variable Region (345 bp):

```
                                  (SEQ ID NO: 13)
GAAGTGCAGCTGGTCGAGTCCGGGGGGGGCCTGGTGC

AGCCAGGAGGATCAATGCGACTGAGCTGCGCCGCTTCCGG

CTTCACCTTCAGCGACAACTGGATGAATTGGGTCAGGCAGG

CACCAGGAAAGGGACTGGAGTGGCTGGCACAGATCCGCAA

CAAACCTTACAACTACGAAACTTACTACAGCGCCTCCGTGA

AGGGGCGGTTCACCATTTCTAGAGACGATTCTAAAAACAGT

GTGTACCTGCAGATGAATAGCCTGAAGACCGAGGATACAGG

AGTCTACTATTGTACCGCACAGTTTGCTTATTGGGGGCAGG

GCACTCTGGTGACAGTCTCTTCA
```

The Protein Sequence Encoded by it (115 Aa):

```
                                  (SEQ ID NO: 14)
EVQLVESGGGLVQPGGSMRLSCAASGFTFSDNWMNWVR

QAPGKGLEWLAQIRNKPYNYETYYSASVKGRFTISRDDSKNSV

YLQMNSLKTEDTGVYYCTAQFAYWGQGTLVTVSS
```

The DNA Sequence of the Light Chain Variable Region (321 bp):

```
                                  (SEQ ID NO: 23)
GACATCCAGATGACTCAGTCACCCAGCTCCCTGAGTG

CTTCAGTGGGCGATCGGGTCACTATCACCTGTAGAACCAGC

GAGAACATTTACGGCGGACTGAATTGGTATCAGAGGAAGCC

CGGGAAAAGCCCTAAGCTGCTGATCTACGGAGCAACAAACC

TGGCCTCCGGCGTGTCTAGTCGCTTCAGCGGCAGCGGCTCT

GGAACCGACTATACACTGACTATTTCAAGCCTGCAGCCAGA

GGATGTGGCCACATACTATTGCCAGAATGTCCTGTCCTCTC

GACCCGGATTTGGCAGTGGGACCAAACTGGAAATTAAG
```

The Protein Sequence Encoded by it (107 Aa):

```
                                  (SEQ ID NO: 24)
DIQMTQSPSSLSASVGDRVITCRTSENIYGGLNWYQRKP

GKSPKLLIYGATNLASGVSSRFSGSGSGTDYTLTISSLQPEDVAT

YYCQNVLSSRPGFGSGTKLEIK
```

Example 4. Preparation of the 8D2 Recombinant Antibody, 8D2(Re), and the 8D2 Humanized Antibodies, 8D2H1L1, 8D2H2L3, 8D2H3L3, 8D2H2L15 and 8D2H2L17, and Detection by SDS-PAGE 1. Preparation of the 8D2 Recombinant Antibody, 8D2 (Re), and Detection by SDS-PAGE The cDNA sequence of the heavy chain (its variable region sequence is shown in SEQ ID NO: 5) and the cDNA sequence of the light chain (its variable region sequence is shown in SEQ ID NO: 7) of 8D2 were cloned into the pUC57simple vector (provided by Genscript Co.), respectively, resulting in the plasmids pUC57simple-8D2H and pUC57simple-8D2L.

Figure 3:
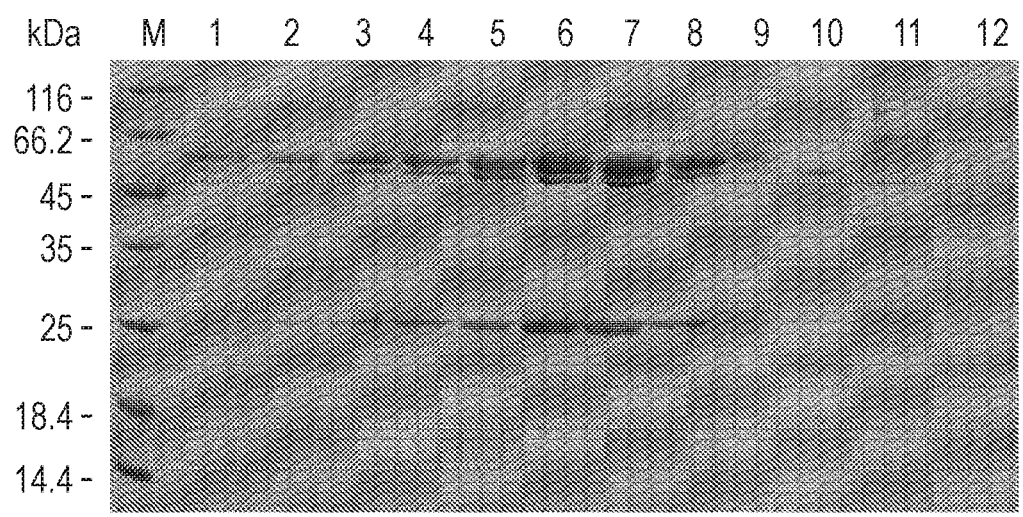
FIG. 3. Results of SDS-PAGE of the 8D2 recombinant antibody (8D2(Re)). The samples and their loading amounts in the 4 lanes, from left to right, were: M, marker, 10 µL; an antibody sample in the reductive loading buffer for protein electrophoresis, 1 µg; the non-reductive loading buffer for protein electrophoresis, 2 µL; an antibody sample in the non-reductive loading buffer for protein electrophoresis, 1 µg.
Figure 4:
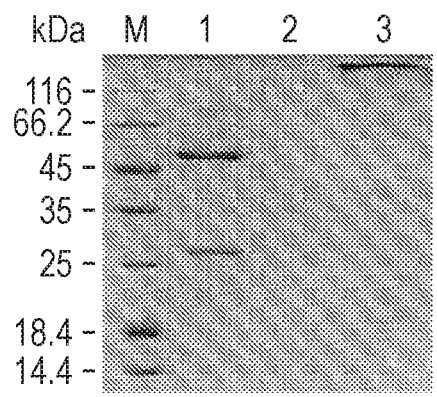
FIG. 4. Results of SDS-PAGE of the humanized antibody of 8D2, 8D2H1L1. The samples and their loading amounts in the 4 lanes, from left to right, were: M, marker, 10 µL; lane 1, an antibody sample in the reductive loading buffer for protein electrophoresis, 1 µg; lane 2, the non-reductive loading buffer for protein electrophoresis, 2 µL; lane 3, an antibody sample in the non-reductive loading buffer for protein electrophoresis, 1 µg.
Figure 5:
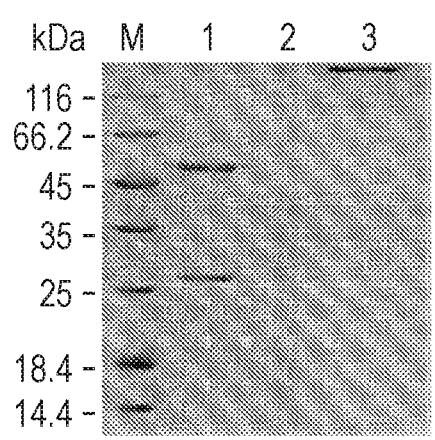
FIG. 5. Results of SDS-PAGE of the humanized antibody of 8D2, 8D2H2L2. The samples and their loading amounts in the 4 lanes, from left to right, were: M, marker, 10 µL; lane 1, an antibody sample in the reductive loading buffer for protein electrophoresis, 1 µg; lane 2, the non-reductive loading buffer for protein electrophoresis, 2 µL; lane 3, an antibody sample in the non-reductive loading buffer for protein electrophoresis, 1 µg.
Figure 6:
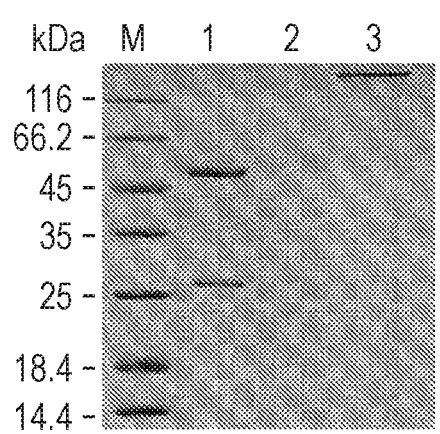
FIG. 6. Results of SDS-PAGE of the humanized antibody of 8D2, 8D2H3L3. The samples and their loading amounts in the 4 lanes, from left to right, were: M, marker, 10 µL; lane 1, an antibody sample in the reductive loading buffer for protein electrophoresis, 1 µg; lane 2, the non-reductive loading buffer for protein electrophoresis, 2 µL; lane 3, an antibody sample in the non-reductive loading buffer for protein electrophoresis, 1 µg.
Figure 7:
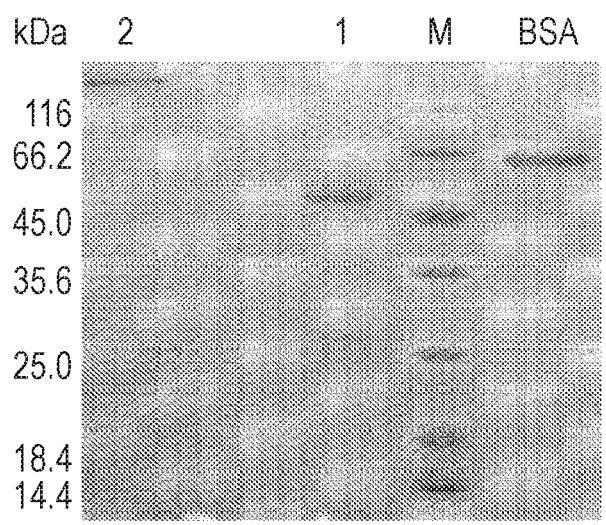
FIG. 7. Results of SDS-PAGE of the humanized antibody of 8D2, 8D2H2L15. The samples and their loading amounts were: M, marker, 10 µL; lane 2, an antibody sample in the non-reductive loading buffer for protein electrophoresis, 1 µg; lane 1, an antibody sample in the reductive loading buffer for protein electrophoresis, 1 µg.
Figure 8:
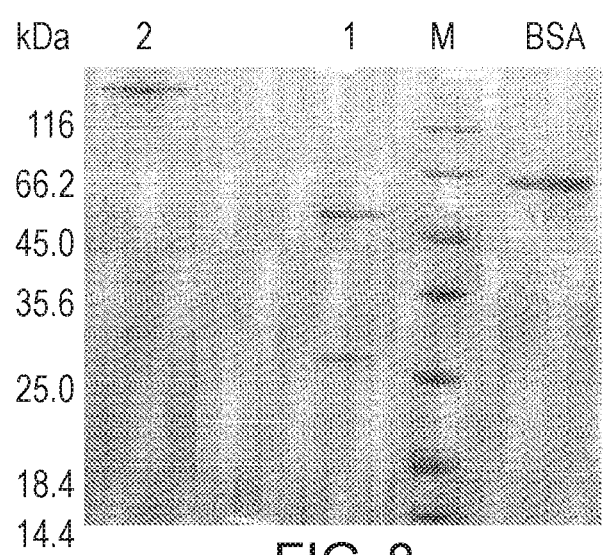
FIG. 8. Results of SDS-PAGE of the humanized antibody of 8D2, 8D2H2L17. The samples and their loading amounts were: M, marker, 10 µL; lane 2, an antibody sample in the non-reductive loading buffer for protein electrophoresis, 1 µg; lane 1, an antibody sample in the reductive loading buffer for protein electrophoresis, 1 µg.

The plasmids pUC57simple-8D2H and pUC57simple-8D2L were digested with the endonucleases (Hind III and EcoR I), respectively. The fragments encoding the heavy chain and light chain recovered via electrophoresis were separately subcloned into the pcDNA3.1 vector. The recombinant plasmids were extracted and co-transfected into cells of 293F. After 7 days of cell culture, the culture liquid was subjected to high speed centrifugation, vacuum filtration through a microporous filter membrane and purification on a HiTrap Protein A HP column. Purified samples were added into the reductive loading buffer for protein electrophoresis and the non-reductive loading buffer for protein electrophoresis. After boiling, detection was performed by SDS-PAGE. As shown in FIG. 3, the protein of interest is shown as two band at about 50 kD and 25 kD for the reductive protein sample, or as a band at about 150 kD for the non-reductive protein sample.

2. Preparation of the 8D2 Humanized Antibodies, 8D2H1L1, 8D2H2L2 and 8D2H3L3, and Detection by SDS-PAGE The cDNA sequences of the heavy chain (their variable region sequences are shown in SEQ ID NO: 9, SEQ ID NO: 13, SEQ ID NO: 17, SEQ ID NO: 13, SEQ ID NO: 13, respectively) and the cDNA sequences of the light chain (their variable region sequences are shown in SEQ ID NO: 11, SEQ ID NO: 15, SEQ ID NO: 19. SEQ ID NO: 21, SEQ ID NO: 23, respectively) of 8D2H1L1, 8D2H2L2, 8D2H3L3, 8D2H2L15, and 8D2H2L17 were cloned into the pUC57simple vector (provided by Genscript Co.), respectively, resulting in the plasmids pUC57simple-8D2H1L1, pUC57simple-8D2H2L2, pUC57simple-8D2H3L3, pUC57simple-8D2H2L15, and pUC57simple-8D2H2L17. They were separately subcloned into the pcDNA3.1 vector following the procedure described above for 8D2(Re).

The recombinant plasmids were transfected into cells of 293F. The culture liquid of the 293F cells were subjected to detection after purification following the procedure described above for 8D2(Re). The results are shown in FIG. 4, FIG. 5, FIG. 6, FIG. 7, and FIG. 8. The reductive protein samples showed the proteins of interest as two bands at about 50 kD and 25 kD, and the non-reductive protein samples showed the proteins of interest as a band at about 150 kD.

The 8D2 recombinant antibody, 8D2(Re), and the 8D2 humanized antibodies, 8D2H1L1, 8D2H2L3, 8D2H3L3, 8D2H2L15 and 8D2H2L17 used in the following examples were prepared following the procedure described in this example.

Example 5. Determination of the Dynamic Parameters of the Antibodies

The dynamic parameters of the binding of the antibodies 8D2 and humanized 8D2H L1, 8D2H2L2 and 8D2H3L3 to the antigen CTLA4 (NCBI Gene ID: 1493, with the coding nucleic acid sequence as shown in SEQ ID NO: 25 and the encoded amino acid sequence as shown in SEQ ID NO: 26) were determined using the Fortebio molecular interaction analyzer.

1. The CTLA4-mFc protein (CTLA4-mFc was generated following the same method as that described in Example 1 for the synthesis of CTLA4ECD-mFc) was cleaved with the TEV protease, and the CTLA4 antigen was obtained by purification on a column.

The Sequence of the CTLA4 Gene (636 bp):

```
                                            (SEQ ID NO: 25)
ATGGGCGTCCTGCTGACTCAGAGAACCCTGCTGTCCCTGGT

GCTGGCACTGCTGTTTCCTTCAATGGCTTCAATGGCTATGCATG

TGGCTCAGCCAGCAGTGGTCCTGGCAAGCTCCAGGGGATCGC

CAGTTTCGTGTGCGAGTACGCCTCACCTGGAAAGGCTACAGAAG

TCCGGGTGACTGTCCTGAGACAGGCTGACTCTCAGGTGACCGA

GGTCTGCGCCGCTACATATATGATGGGCAACGAACTGACCTTTC

TGGACGATTCCATTTGTACTGGCACCTCTAGTGGGAACCAAGTG

AATCTGACTATCCAGGGACTGCGAGCAATGGACACCGGACTGTA

CATTTGCAAAGTGGAGCTGATGTATCCCCCTCCATACTATCTGG

GCATCGGGAATGGAACACAGATCTACGTGATTGATCCCGAACCT

TGTCCAGACAGCGATTTCCTGCTGTGGATTCTGGCAGCCGTGTC

AAGCGGCCTGTTCTTTTATAGCTTTCTGCTGACTGCCGTCTCCCT

GTCTAAGATGCTGAAGAAACGATCCCCCCTGACCACAGGGGTG

GTCGTGAAAATGCCACCTACCGAGCCCGAGTGCGAAAAACAGTT

CCAGCCATACTTTATCCCTATCAAT
```

The Encoded Corresponding Amino Acid Sequence (212 Aa):

```
                                            (SEQ ID NO: 26)
MGVLLTQRTLLSLVLALLFPSMASMAMHVAQPAVVLASSRGI

ASFVCEYASPGKATEVRVTVLRQADSQVTEVCAATYMMGNELTFL

DDSICTGTSSGNQVNLTIQGLRAMDTGLYICKVELMYPPPYYLGIG

NGTQIYVIDPEPCPDSDFLLWILAAVSSGLFFYSFLLTAVSLSKMLK

KRSPLTTGVVVKMPPTEPECEKQFQPYFIPIN
```

2. The antibody 8D2 and its humanized antibodies 8D2H1L1, 8D2H2L2, 8D2H3L3, 8D2H2L15, and 8D2H2L17 were immobilized on the surface of the AR2G sensor by amino coupling, and blocked with ethanolamine. After equilibration in PBST, the CTLA4 antigen was added for binding. CTLA4 was serially 2× diluted in PBST, and the following concentrations were obtained: 300, 150, 75, 37.5, 18.75, 9.38, 4.69, 0 nM. Dissociation occurred in PBST. The humanized antibodies 8D2H1L1, H2L2, H3L3, H2L15, and H2L17 were detected by a method same as 8D2, and the antigen concentrations were 180, 90, 45, 22.5, 11.25, 5.625, 2.813, 0 nM.

The dynamic parameters of the antibody 8D2 and its humanized antibodies 8D2H1L1, 8D2H2L2, 8D2H3L3, 8D2H2L15, and 8D2H2L17 are provided in Table 1.

TABLE 1

Dynamic parameters of the antibodies 8D2, 8D2H1L1, 8D2H2L2, 8D2H3L3, 8D2H2L15, and 8D2H2L17

| Antibody Name | $K_D$ (M) | $k_{on}$ (1/Ms) | $k_{on}$ Error | $k_{dis}$ (1/s) | $k_{dis}$ Error |
|---|---|---|---|---|---|
| 8D2 | 1.66E−10 | 1.42E+05 | 1.22E+03 | 2.36E−05 | 2.09E−06 |
| 8D2H1L1 | 6.08E−10 | 3.40E+05 | 1.17E+04 | 2.07E−04 | 1.81E−05 |
| 8D2H2L2 | 9.55E−10 | 4.07E+05 | 1.59E+04 | 3.88E−04 | 1.60E−05 |
| 8D2H3L3 | 1.05E−09 | 3.12E+05 | 1.01E+04 | 3.27E−04 | 1.41E−05 |
| 8D2H2L15 | 1.02E−09 | 4.54E+05 | 8.18E+03 | 4.65E−04 | 9.50E−06 |
| 8D2H2L17 | 7.66E−10 | 4.59E+05 | 8.21E+03 | 3.52E−04 | 8.30E−06 |
| 10D1 | 1.21E−09 | 4.67E+05 | 1.15E+04 | 5.65E−04 | 1.51E−05 |
| 11.2.1 | 9.03E−10 | 3.87E+05 | 5.46E+03 | 3.49E−04 | 7.32E−06 |

$K_D$, affinity constant; $k_{on}$, antigen - antibody association rate; $k_{dis}$, antigen - antibody dissociation rate; $K_D = k_{dis}/k_{on}$.

The results demonstrate that all of the six antibodies have a good affinity for the antigen, which is comparable or even superior than the control antibodies 10D1 and 11.2.1.

Example 6. Determination of the Activity of the Antibodies to Bind to the Antigen CTLA4 on the Surface of the Hybridoma Cell Line by Flow Cytometry First, 293F host cells expressing the CTLA4 antigen were generated, and labeled with the monoclonal antibody 8D2 (Example 1) and 8D2(Re) and the 8D2 humanized antibodies 8D2H1L1, 8D2H2L2 and 8D2H3L3 (Example 4) prepared in the present invention, respectively. Then, the ability of the antibodies to specifically bind to the antigen having native conformation on the surface of cells was verified by flow cytometry.

The specific steps are provided below.

1. Generation of 293F Host Cells Expressing the CTLA4 Antigen

Cells of 293F were transfected with the plasmid pLenti6.3-CTLA4 for CTLA4 (the vector pLenti6.3 was purchased from Invitrogen Co.) using the Lipofectamin transfection kit (purchased from Invitrogen Co.). After screening, a clonal population of cells stably expressing CTLA4 (293F-CTLA4) was obtained.

2. Labeling with the Antibodies and Detection Using a Flow Cytometer

The 293F host cells expressing the CTLA4 antigen obtained by the above steps were digested with trypsin following a conventional method, and $2 \times 10^5$ cells were added to each collection tube. The diluted solutions of the 8D2 antibody in PBS containing 1% BSA were prepared to achieve the concentrations of 20 nM, 10 nM, 5 nM, 1 nM, 0.1 nM, 0.01 nM, and 0 nM, respectively. After incubation with 293F cells expressing CTLA4 on ice for 2 hours, 100 μL FITC-Goat-Anti-Mouse IgG (1:500) was added to each tube, and the tubes were incubated on ice for 1 hour. After addition of 300 μL PBS, the fluorescent signal was detected using the FITC channel on the flow cytometer. Other antibodies were detected in a similar way to the 8D2 antibody.

3. Results

Figure 9:
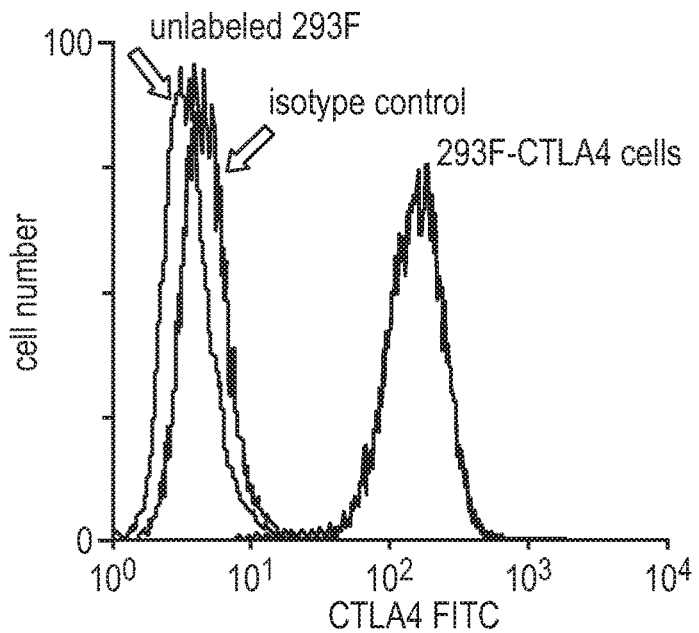
FIG. 9. A histogram showing the expression of CTLA4 on non-labeled 293F cells, isotype control, and 293F-CTLA4 cells as detected using a flow cytometry (cell number—fluorescence (FITC)).
Figure 10:
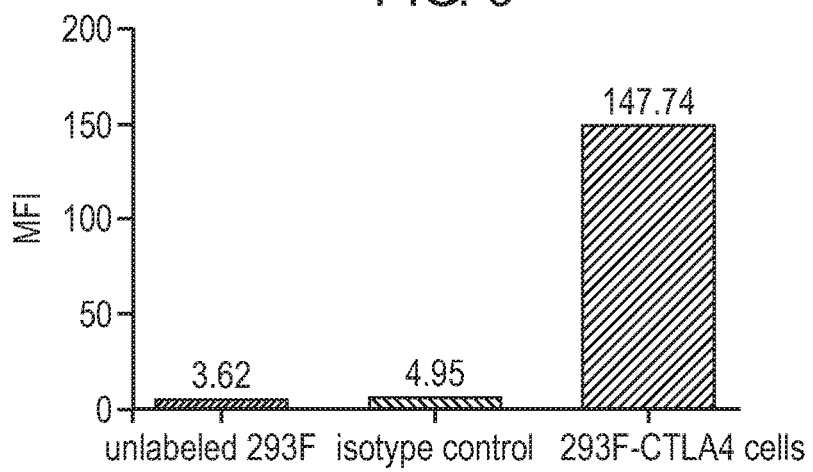
FIG. 10. Mean fluorescence intensity (MFI) of the expression of CTLA4 on non-labeled 293F cells, isotype control, and 293F-CTLA4 cells as detected using a flow cytometry.
Figure 11:
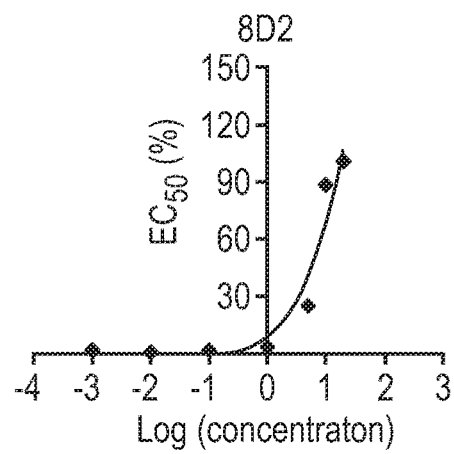
FIG. 11. The $EC_{50}$ results of the binding of the mAb 8D2 to the labeled 293F-CTLA4 cells.
Figure 12:
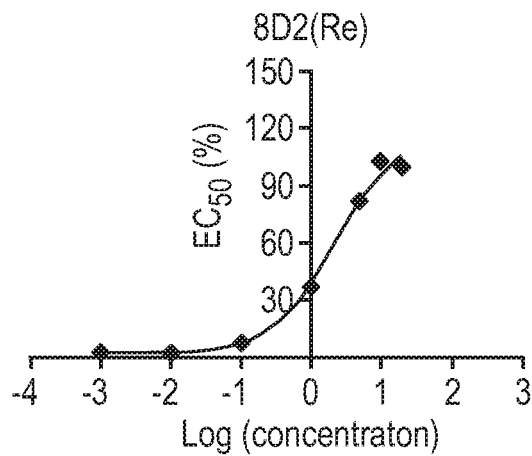
FIG. 12. The $EC_{50}$ results of the binding of the 8D2(Re) antibody to the labeled 293F-CTLA4 cells.
Figure 13:
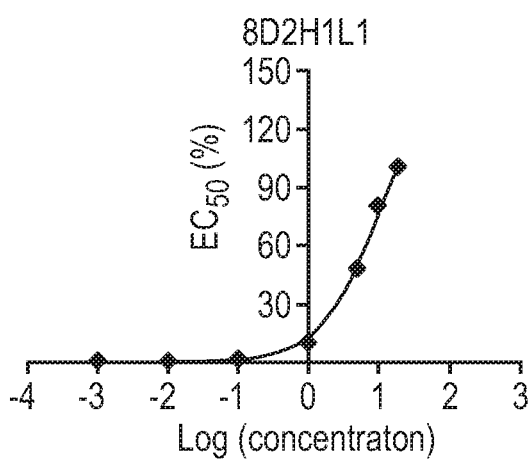
FIG. 13. The $EC_{50}$ results of the binding of 8D2H1L1 to the labeled 293F-CTLA4 cells.
Figure 14:
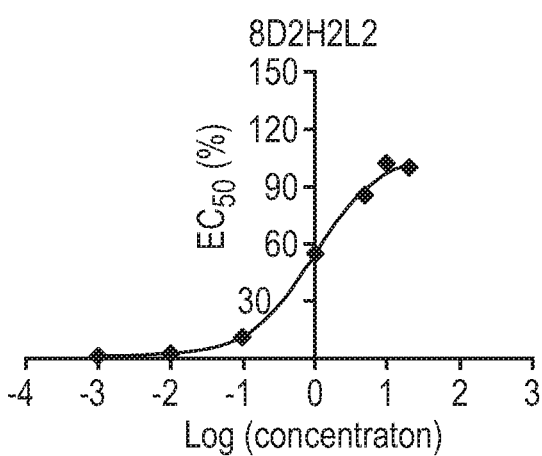
FIG. 14. The $EC_{50}$ results of the binding of 8D2H2L2 to the labeled 293F-CTLA4 cells.
Figure 17:
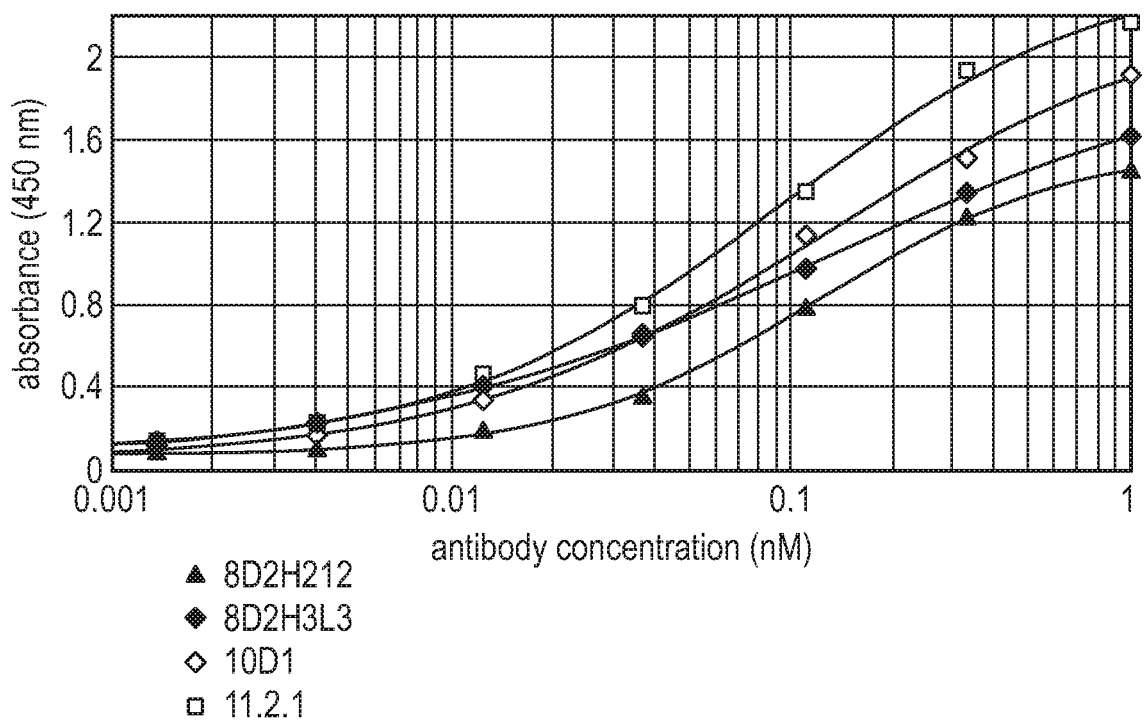
FIG. 17. Determination of the binding of the recombinant antibodies 8D2H2L2 and 8D2H3L3 and control antibodies 10D1 and 11.2.1 to human CTLA4 using the ELISA method.
Figure 18:
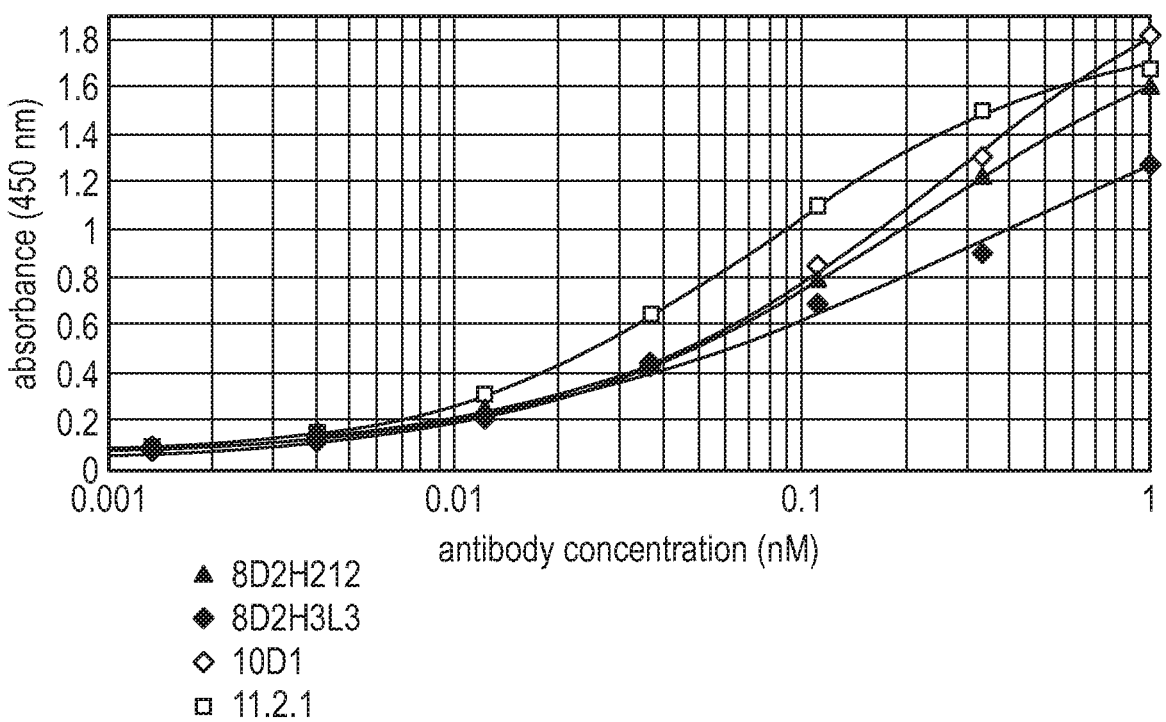
FIG. 18. Determination of the binding of the recombinant antibodies 8D2H2L2 and 8D2H3L3 and control antibodies 10D1 and 11.2.1 to monkey CTLA4 using the ELISA method.
Figure 21:
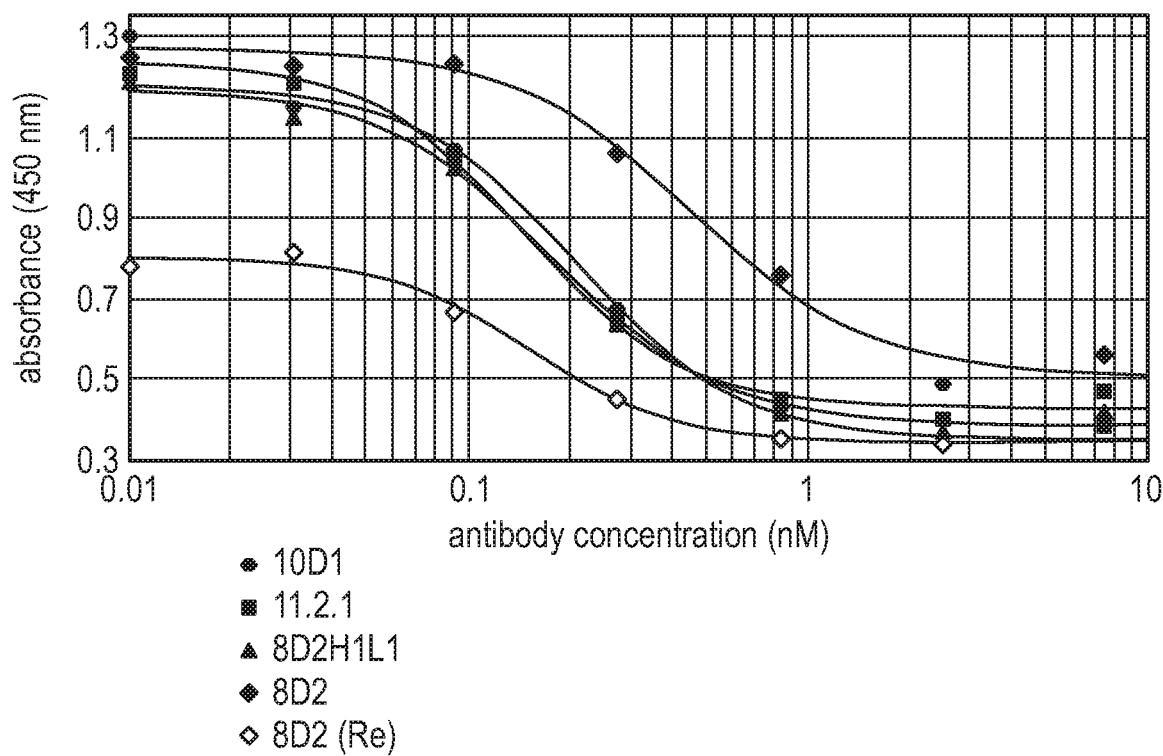
FIG. 21. Results of ELISA for competition of the antibodies 8D2, 8D2H1L1, and 8D2(Re), and control antibodies 10D1 and 11.2.1 with B7-2.
Figure 22:
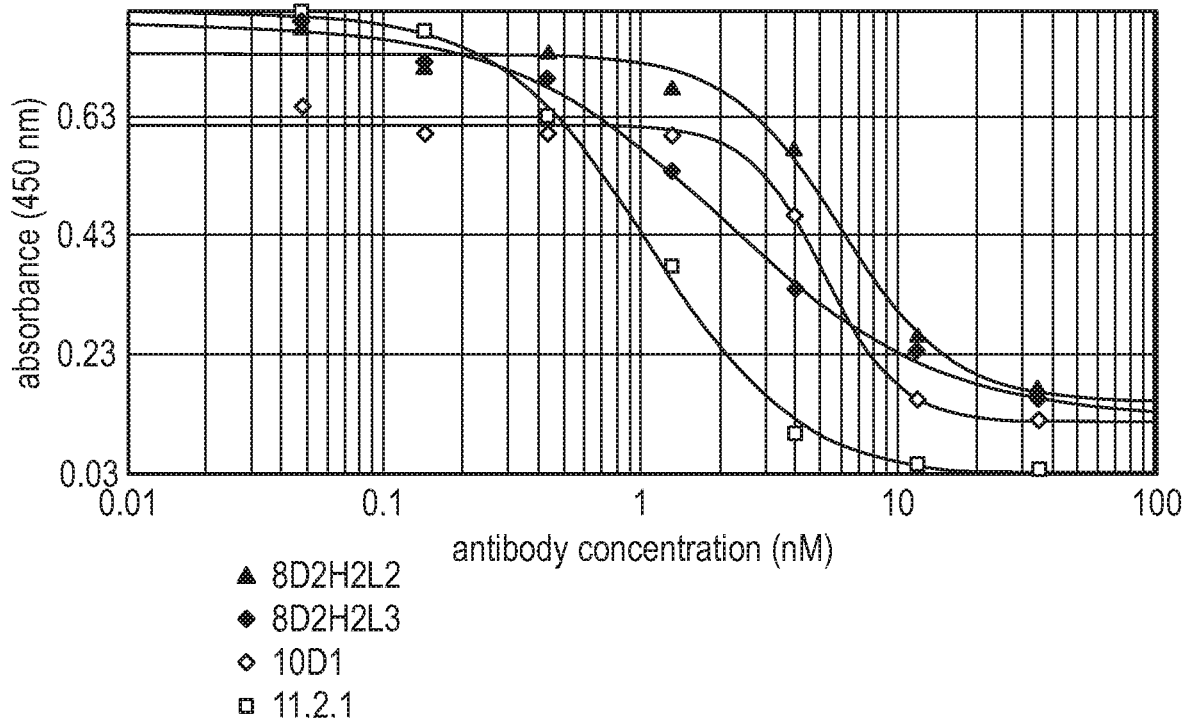
FIG. 22. Results of ELISA for competition of the 8D2H2L2 and 8D2H3L3 antibodies and control antibodies 10D1 and 11.2.1 with B7-1.
Figure 23:
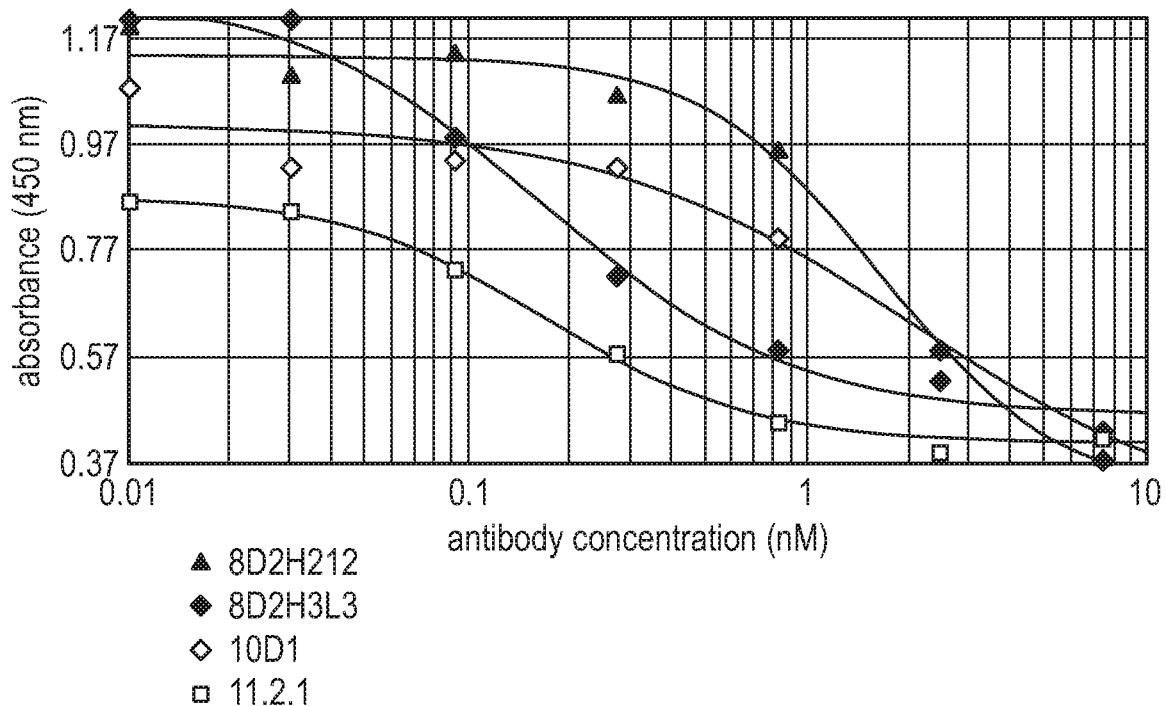
FIG. 23. Results of ELISA for competition of the 8D2H2L2 and 8D2H3L3 antibodies and control antibodies 10D1 and 11.2.1 with B7-2.
Figure 24:
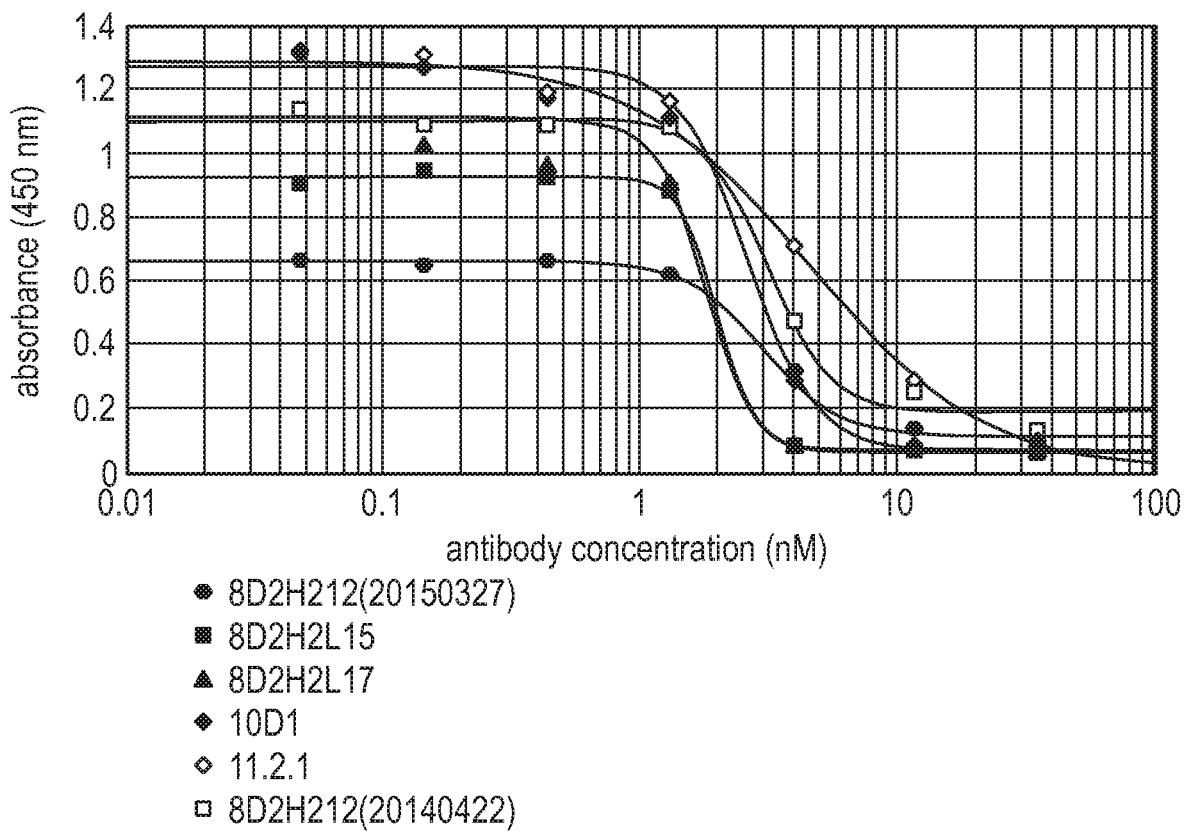
FIG. 24. Results of ELISA for competition of the 8D2H2L2(20150327), 8D2H2L15, 8D2H2L17, 8D2H2L2 (20140422) antibodies and control antibodies 10D1 and 11.2.1 with B7-1.
Figure 25:
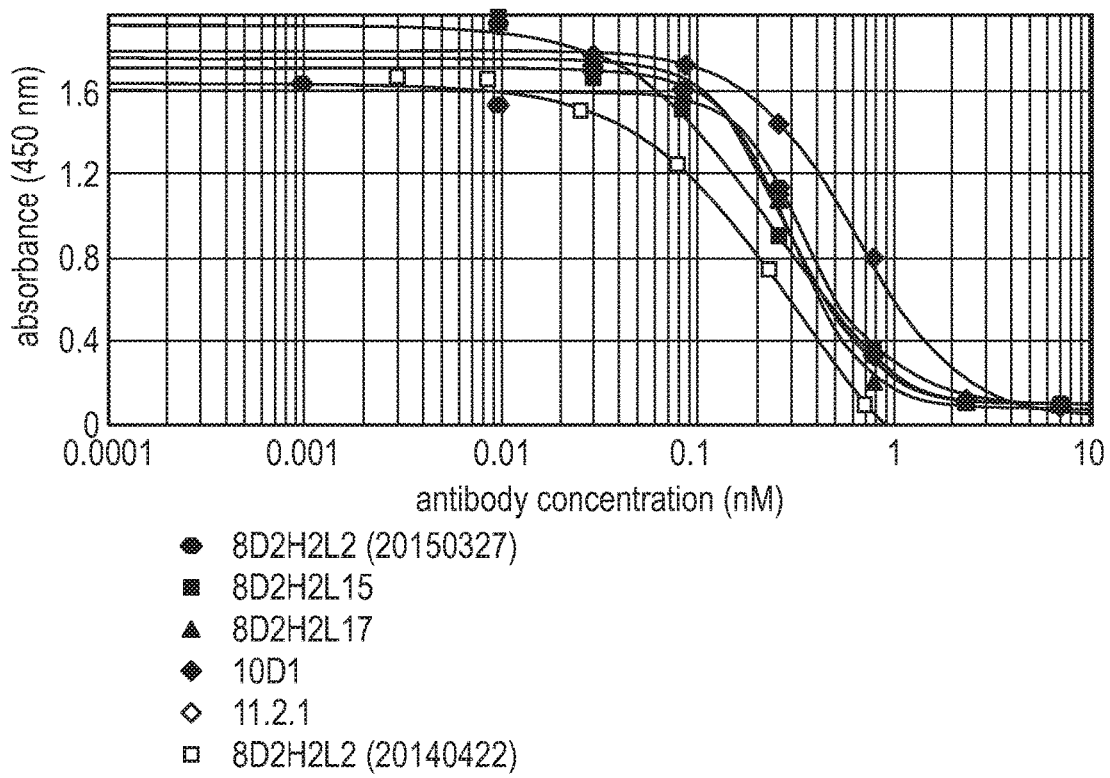
FIG. 25. Results of ELISA for competition of the 8D2H2L2(20150327), 8D2H2L15, 8D2H2L17, 8D2H2L2 (20140422) antibodies and control antibodies 10D1 and 11.2.1 with B7-2.

The results of verifying the expression of CTLA4 on 293F-CTLA4 cells are shown in FIG. 9 and FIG. 10, respectively. The results of the binding of the antibodies 8D2, 8D2(Re), and the three humanized antibodies to 293F cells are shown in FIGS. 11 to 15, respectively. As shown in the figures, the 8D2 antibody and its humanized antibodies can effectively bind to the CTLA4 target protein on the surface of the 293F host cell, and their binding efficiency is dose-dependent. The fluorescent intensities at each dose are provided in Table 2.

The binding efficiency, $EC_{50}$, of 8D2 and its humanized antibodies was obtained by curve simulation in the fluorescent quantitative analysis of the bound antibodies 8D2 and its humanized antibodies, which is shown in Table 3.

TABLE 2

Fluorescent intensity analysis determining the binding of 8D2, 8D2(Re) and the 8D2 humanized antibodies 8D2H1L1, 8D2H2L2 and 8D2H3L3 to the CTLA4 antigen on the surface of the 293F-CTLA4 host cell by flow cytometry

| concentration (nM) | 8D2 | 8D2(Re) | 8D2H1L1 | 8D2H2L2 | 8D2H3L3 |
|---|---|---|---|---|---|
| | | | fluorescence intensity | | |
| 0.001 | 7.60 | 24.62 | 10.84 | 10.85 | 10.85 |
| 0.01 | 7.70 | 24.72 | 10.85 | 32.48 | 25.14 |
| 0.1 | 9.10 | 66.72 | 21.25 | 124.03 | 108.29 |
| 1 | 25.50 | 321.27 | 103.04 | 624.65 | 623.25 |
| 5 | 182.60 | 713.87 | 558.75 | 972.03 | 970.80 |
| 10 | 638.60 | 897.63 | 943.84 | 1159.24 | 1084.74 |
| 25 | 721.80 | 873.24 | 1170.64 | 1132.39 | 1091.77 |

TABLE 3

The binding efficiency, $EC_{50}$, of 8D2, 8D2(Re) and the 8D2 humanized antibodies 8D2H1L1, 8D2H2L2 and 8D2H3L3 to the CTLA4 antigen on the surface of the 293F-CTLA4 host cell obtained by curve simulation in the analysis by flow cytometry

| | 8D2 | 8D2(Re) | 8D2H1L1 | 8D2H2L2 | 8D2H3L3 |
|---|---|---|---|---|---|
| $EC_{50}$ (nM) | 3.84 | 1.38 | 5.06 | 4.37 | 4.54 |

The results demonstrate that the antibodies 8D2, 8D2(Re) and the 8D2 humanized antibodies 8D2H1L1, 8D2H2L2 and 8D2H3L3 all have a very strong capability to bind to the CTLA4 antigen on the surface of the 293F-CTLA4 host cells.

Example 7. Determination of the Activity of the Antibodies to Bind to the CTLA4 Antigen by ELISA The ELISA plate was coated with CTLA4 at 4° C. over night. After blocking with 1% BSA at 37° C. for 2 h, the CTLA4 antibodies 8D2, 8D2(Re) and the 8D2 humanized antibodies 8D2H1L1, 8D2H2L2, 8D2H3L3, 8D2H2L15, and 8D2H2L17, and the control antibodies 10D1 (Alan J. Korman. Edward L. Halk, et al., HUMAN CTLA-4 ANTIBODIES, U.S. Pat. No. 6,984,720 B1) and 11.2.1 (Douglas Charles Hanson, Mark Joseph Neveu, et al., Human monoclonal antibodies to CTLA-4, U.S. Pat. No. 682,736 B1) were added for reaction for 30 min. The enzyme conjugated secondary antibody was added for incubation for 30 min. Then, the absorbance at 450 nm was determined on an ELISA plate reader.

The results of detecting the binding of the 8D2 antibody and its humanized antibodies to the CTLA4 antigen are shown in FIGS. 14 to 19, respectively. As shown in the figures, the antibodies 8D2, 8D2(Re) and the 8D2 humanized antibodies all can effectively bind to the CTLA4 protein, and their binding efficiency is dose-dependent. The fluorescent intensities at each dose are provided in Tables 4 to 8. The binding efficiency, $EC_{50}$, of 8D2, 8D2(Re) and the humanized antibodies was obtained by curve simulation in the fluorescent quantitative analysis of the bound 8D2, 8D2(Re) and the humanized antibodies (Table 9).

TABLE 4

Binding of 8D2 and 8D2(Re) to murine CTLA4 (ELISA)

| Antibody concentration | Antigen coating: murine CTLA4 at 0.5 µg/ml | | | | | |
|---|---|---|---|---|---|---|
| (µg/ml) | 8D2 | | 8D2(Re) | | 10D1 | |
| 1 | 2.823 | 2.682 | 2.672 | 2.769 | 2.995 | 2.975 |
| 0.3 | 2.806 | 2.763 | 2.690 | 2.735 | 2.852 | 2.900 |
| 0.1 | 2.754 | 2.718 | 2.796 | 2.685 | 2.429 | 2.538 |
| 0.03 | 2.336 | 2.381 | 2.305 | 2.259 | 1.507 | 1.704 |
| 0.01 | 1.614 | 1.560 | 1.397 | 1.446 | 0.673 | 0.794 |
| 0.003 | 0.784 | 0.760 | 0.662 | 0.674 | 0.292 | 0.328 |
| 0.001 | 0.358 | 0.355 | 0.315 | 0.321 | 0.136 | 0.142 |
| 0 | 0.063 | 0.052 | 0.053 | 0.046 | 0.046 | 0.050 |
| Secondary antibody | Goat Anti Mouse Secondary Antibody | | | | Goat Anti Human Secondary Antibody | |

TABLE 5

Binding of 8D2, 8D2H1L1 and 8D2(Re) to human CTLA4 (ELISA)

| Antibody concentration | Antigen coating: human CTLA4 at 0.5 µg/ml | | | | | | | | | |
|---|---|---|---|---|---|---|---|---|---|---|
| (µg/ml) | 10D1 | | 11.2.1 | | 8D2H1L1 | | 8D2 | | 8D2(Re) | |
| 1 | 3.479 | 3.432 | 3.584 | 3.547 | 3.016 | 3.031 | 3.029 | 3.107 | 3.058 | 3.085 |
| 1:3 | 3.323 | 3.155 | 3.499 | 3.479 | 2.834 | 2.904 | 3.076 | 3.074 | 2.930 | 3.072 |
| 1:9 | 2.506 | 2.293 | 3.211 | 3.187 | 2.610 | 2.670 | 2.878 | 2.988 | 2.805 | 2.868 |
| 1:27 | 1.331 | 1.194 | 2.337 | 2.293 | 1.834 | 1.944 | 2.265 | 2.287 | 2.052 | 2.064 |
| 1:81 | 0.552 | 0.528 | 1.254 | 1.267 | 0.969 | 0.996 | 1.335 | 1.479 | 1.398 | 1.271 |
| 1:243 | 0.202 | 0.222 | 0.536 | 0.552 | 0.450 | 0.515 | 0.666 | 0.770 | 0.634 | 0.649 |
| 1:729 | 0.141 | 0.115 | 0.253 | 0.263 | 0.204 | 0.206 | 0.277 | 0.351 | 0.307 | 0.309 |
| 0 | 0.090 | 0.086 | 0.072 | 0.064 | 0.067 | 0.064 | 0.067 | 0.071 | 0.086 |
| Secondary Antibody | Goat Anti Human IgG Secondary antibody | | | | | | Goat Anti Mouse IgG Secondary Antibody | | | |

TABLE 6

Binding of 8D2H2L2 and 8D2H3L3 to human CTLA4 (ELISA)

| Antibody concentration | Antigen coating: human CTLA4 at 0.5 µg/ml | | | | | | | |
|---|---|---|---|---|---|---|---|---|
| (µg/ml) | 8D2H2L2 | | 8D2H3L3 | | 10D1 | | 11.2.1 | |
| 1 | 1.489 | 1.411 | 1.631 | 1.601 | 1.775 | 2.069 | 2.206 | 2.150 |
| 1:3 | 1.178 | 1.262 | 1.192 | 1.455 | 1.527 | 1.480 | 1.825 | 2.047 |
| 1:9 | 0.710 | 0.872 | 0.943 | 1.007 | 1.073 | 1.204 | 1.292 | 1.409 |
| 1:27 | 0.336 | 0.370 | 0.642 | 0.658 | 0.663 | 0.585 | 0.893 | 0.682 |
| 1:81 | 0.192 | 0.195 | 0.415 | 0.374 | 0.349 | 0.323 | 0.499 | 0.426 |
| 1:243 | 0.097 | 0.109 | 0.230 | 0.214 | 0.132 | 0.146 | 0.223 | 0.219 |
| 1:729 | 0.075 | 0.083 | 0.100 | 0.130 | 0.099 | 0.099 | 0.127 | 0.136 |
| 0 | 0.052 | 0.055 | 0.052 | 0.057 | 0.056 | 0.053 | 0.057 | 0.061 |
| Secondary antibody | HRP Conjugated Goat Anti Human IgG Secondary Antibody | | | | | | | |

TABLE 7

Binding of 8D2H2L2 and 8D2H3L3 to monkey CTLA4 (ELISA)

| Antibody concentration | Antigen coating: monkey CTLA4-hFc at 0.25 µg/ml | | | | | | | |
|---|---|---|---|---|---|---|---|---|
| (µg/ml) | 8D2H2L2 | | 8D2H3L3 | | 10D1 | | 11.2.1 | |
| 1 | 1.576 | 1.624 | 1.235 | 1.321 | 1.788 | 1.846 | 1.718 | 1.632 |
| 1:3 | 1.223 | 1.199 | 0.921 | 0.873 | 1.250 | 1.344 | 1.540 | 1.460 |
| 1:9 | 0.793 | 0.775 | 0.654 | 0.724 | 0.845 | 0.868 | 1.114 | 1.054 |
| 1:27 | 0.471 | 0.426 | 0.441 | 0.403 | 0.429 | 0.402 | 0.625 | 0.665 |
| 1:81 | 0.220 | 0.230 | 0.239 | 0.218 | 0.190 | 0.191 | 0.297 | 0.313 |
| 1:243 | 0.114 | 0.117 | 0.123 | 0.119 | 0.104 | 0.108 | 0.130 | 0.172 |
| 1:729 | 0.071 | 0.076 | 0.088 | 0.096 | 0.063 | 0.067 | 0.082 | 0.094 |
| 0 | 0.048 | 0.048 | 0.048 | 0.050 | 0.049 | 0.053 | 0.048 | 0.051 |
| Secondary antibody | HRP Conjugated Goat Anti Human IgG, F(ab')$_2$ Secondary Antibody | | | | | | | |

TABLE 8

Binding of 8D2H2L15 and 8D2H2L17 to human CTLA4 (ELISA)

| Antibody concentration (μg/ml) | 8D2H2L2 20150327 | | 8D2H2L15 | | 8D2H2L17 | | 10D1 | | 11.2.1 | | 8D2H2L2 20140422 | |
|---|---|---|---|---|---|---|---|---|---|---|---|---|
| 1 | 2.34 | 2.37 | 2.58 | 2.55 | 2.61 | 2.81 | 2.56 | 2.74 | 2.75 | 2.69 | 2.23 | 2.40 |
| 1:3 | 2.22 | 2.09 | 2.65 | 2.72 | 2.73 | 2.78 | 2.42 | 2.44 | 2.56 | 2.66 | 2.09 | 2.07 |
| 1:9 | 2.03 | 1.87 | 2.79 | 2.45 | 2.59 | 2.73 | 2.20 | 2.20 | 2.69 | 2.44 | 1.92 | 1.95 |
| 1:27 | 1.82 | 1.93 | 2.43 | 2.21 | 2.41 | 2.28 | 1.81 | 1.70 | 2.13 | 2.28 | 1.47 | 1.63 |
| 1:81 | 1.10 | 1.17 | 1.95 | 1.83 | 1.80 | 1.68 | 1.03 | 1.09 | 1.37 | 1.53 | 1.10 | 1.01 |
| 1:243 | 0.65 | 0.58 | 1.05 | 1.02 | 1.14 | 1.19 | 0.51 | 0.53 | 0.75 | 0.79 | 0.49 | 0.50 |
| 1:729 | 0.26 | 0.21 | 0.53 | 0.44 | 0.57 | 0.50 | 0.21 | 0.24 | 0.32 | 0.31 | 0.23 | 0.20 |
| 0 | 0.04 | 0.05 | 0.05 | 0.04 | 0.04 | 0.05 | 0.04 | 0.05 | 0.05 | 0.05 | 0.05 | 0.05 |

Secondary Antibody: HRP Conjugated Goat Anti Human IgG (1:5000)

TABLE 9

The binding efficiency, $EC_{50}$, of 8D2, 8D2(Re) and the 8D2 humanized antibodies 8D2H1L1, 8D2H2L2, 8D2H3L3, 8D2H2L15, and 8D2H2L17 to the CTLA4 antigen obtained by curve simulation in the analysis by ELISA

| | Source of the CTLA4 antigen | Antibody $EC_{50}$ (nM) | 10D1 $EC_{50}$ (nM) | 11.2.1 $EC_{50}$ (nM) |
|---|---|---|---|---|
| 8D2 | Mouse | 0.015 0.071 | 0.062 0.24 | 0.023 |
| 8D2(Re) | Mouse | 0.015 0.085 | 0.062 0.24 | 0.023 |
| 8D2H1L1 | Mouse | 0.025 | 0.062 | 0.023 |
| 8D2H2L2 | Human | 0.12 | 0.125 | 0.09 |
| 8D2H2L2 | Human | 0.082 | 0.125 | 0.09 |
| 8D2H2L2 | Human | 0.118 | 0.125 | 0.09 |
| 8D2H3L3 | Human | 0.129 | 0.125 | 0.09 |
| 8D2H2L2 | Monkey | 0.227 | 0.258 | 0.075 |
| 8D2H3L3 | Monkey | 0.385 | 0.258 | 0.075 |
| 8D2H2L15 | Human | 0.042 | 0.138 | 0.075 |
| 8D2H2L17 | Human | 0.047 | 0.138 | 0.075 |

Note:
8D2H2L2 was measured in triplicate.

The above results demonstrate that the antibodies 8D2 and 8D2(Re) bind to the murine CTLA4 antigen with an efficiency better than that of the control antibodies 10D1 and 11.2.1. The humanized antibody 8D2H1L1 binds to the murine CTLA4 antigen with an efficiency stronger than that of the control antibody 10D1 and comparable to that of 11.2.1.

The humanized antibody 8D2H2L2 binds to the human CTLA4 antigen with an efficiency comparable to that of 10D1. The humanized antibodies 8D2H2L2 and 8D2H3L3 bind to the monkey CTLA4 antigen with an efficiency comparable to that of 10D1. The humanized antibody 8D2H2L15 and 8D2H2L17 bind to the human CTLA4 antigen with an efficiency significantly stronger than that of the control antibodies 10D1 and 11.2.1.

Example 8. Detection of the Activity of the Antibodies to Compete with B7-1/2 for Binding to the CTLA4 Antigen by Competitive ELISA 1. Detection of the Activity of the Antibodies to Compete with B7-1 for Binding to the CTLA4 Antigen by ELISA The ELISA plates were coated with B7-1 at 4° C. overnight. After blocking with 1% BSA at 37° C. for 2 h, the anti-CTLA4 antibodies, i.e., the monoclonal antibodies 8D2 and 8D2(Re) and the 8D2 humanized antibodies 8D2H1L1, 8D2H2L2, 8D2H3L3, 8D2H2L15, and 8D2H2L17, as well as the control antibodies 10D1 and 11.2.1 were added. After incubation for 10 minutes, CTLA4-mFc was added. After incubation at 37° C. for 40 minutes, the enzyme conjugated secondary antibody was added. After incubation at 37° C. for 30 minutes, the absorbance at 450 nm was detected on an ELISA plate reader.

2. Detection of the Activity of the Antibodies to Compete with B7-2 for Binding to the CTLA4 Antigen by ELISA The ELISA plates were coated with CTLA4-mFc at 4° C. overnight. After blocking with 1% BSA at 37° C. for 2 h, the anti-CTLA4 antibodies, i.e., the monoclonal antibodies 8D2 and 8D2(Re) and the 8D2 humanized antibodies 8D2H1L1, 8D2H2L2, 8D2H3L3, 8D2H2L15, and 8D2H2L17, as well as the control antibodies 10D1 and 11.2.1 were added. After incubation for 10 minutes, B7-2-his was added. After incubation at 37° C. for 40 minutes, the enzyme conjugated secondary antibody was added. After incubation at 37° C. for 30 minutes, the absorbance at 450 nm was detected on an ELISA plate reader. The results of detecting the binding of the 8D2, 8D2(Re) and humanized antibodies to the CTLA4 antigen are shown in FIGS. 20 to 25, respectively. As shown in the figures, the 8D2, 8D2(Re) antibodies and the 8D2 humanized antibodies could effectively bind to the CTLA protein, and their binding efficiency is dose-dependent. The fluorescent intensities at each dose are provided in Tables 10 to 16. The binding efficiency, $EC_{50}$, of 8D2, 8D2(Re) and the humanized antibodies was obtained by curve simulation in the fluorescent quantitative analysis of the bound antibodies 8D2, 8D2(Re) and the humanized antibodies (Table 17).

TABLE 10

8D2 and 8D2(Re) compete with B7-1 in ELISA

| Antibody concentration (μg/ml) | Antigen coating: CTLA4-mFc at 0.2 μg/ml. | | | |
|---|---|---|---|---|
| | 8D2 | | 8D2(Re) | |
| 3 | 0.163 | 0.149 | 0.176 | 0.215 |
| 1 | 0.208 | 0.188 | 0.200 | 0.214 |
| 0.3 | 0.354 | 0.347 | 0.355 | 0.390 |
| 0.1 | 0.680 | 0.695 | 0.668 | 0.721 |
| 0.03 | 1.378 | 1.262 | 1.430 | 1.708 |
| 0.01 | 1.758 | 1.612 | 1.630 | 1.824 |
| 0.003 | 1.982 | 1.711 | 1.890 | 1.937 |
| 0 | 2.228 | 1.766 | 1.805 | 1.779 |
| | B7/1-hFc (0.3 μg/ml) | | | |
| Secondary antibody | Goat Anti Human Secondary Antibody | | | |

TABLE 11

8D2, 8D2H1L1 and 8D2(Re) compete with B7-1 in ELISA

| Antibody concentration (μg/ml) | 10D1 | | 11.2.1 | | 8D2 H1L1 | | CTLA4-mFc (0.6 μg/ml) 1:2 | |
|---|---|---|---|---|---|---|---|---|
| 3 | 0.168 | 0.158 | 0.101 | 0.105 | 0.123 | 0.138 | 0.824 | 0.791 |
| 1:3 | 0.258 | 0.232 | 0.119 | 0.133 | 0.206 | 0.231 | 0.640 | 0.768 |
| 1:9 | 0.515 | 0.466 | 0.381 | 0.485 | 0.445 | 0.529 | 0.750 | 0.717 |
| 1:27 | 0.577 | 0.508 | 0.597 | 0.579 | 0.509 | 0.659 | 0.653 | 0.626 |
| 1:81 | 0.801 | 0.730 | 0.650 | 0.613 | 0.669 | 0.723 | 0.571 | 0.522 |
| 1:243 | 0.814 | 0.848 | 0.900 | 0.520 | 0.841 | 0.821 | 0.459 | 0.327 |
| 1:729 | 0.854 | 0.732 | 0.993 | 0.841 | 0.848 | 0.822 | 0.312 | 0.232 |
| 0 | 0.856 | 0.812 | 0.826 | 0.550 | 0.672 | 0.600 | 0.071 | 0.074 |
| Antigen | CTLA4-mFc 0.3 μg/ml | | | | | | Control | |
| Second antibody | HRP Conjugated Goat Anti Mouse IgG Second Antibody | | | | | | | |

TABLE 12

8D2, 8D2H1L1 and 8D2(Re) compete with B7-2 in ELISA

| Antibody concentration μg/ml | Antigen coating: CTLA4-mFc at 0.5 μg/ml | | | | | | | | | |
|---|---|---|---|---|---|---|---|---|---|---|
| | 10D1 | | 11.2.1 | | 8D2 H1L1 | | 8D2 | | 8D2(Re) | |
| 3 | 0.569 | 0.550 | 0.492 | 0.442 | 0.450 | 0.384 | 0.407 | 0.336 | 0.367 | 0.375 |
| 1:3 | 0.500 | 0.466 | 0.387 | 0.402 | 0.404 | 0.332 | 0.359 | 0.306 | 0.331 | 0.289 |
| 1:9 | 0.736 | 0.782 | 0.412 | 0.482 | 0.467 | 0.371 | 0.456 | 0.355 | 0.384 | 0.315 |
| 1:27 | 0.982 | 1.137 | 0.676 | 0.585 | 0.671 | 0.633 | 0.675 | 0.675 | 0.464 | 0.443 |
| 1:81 | 1.196 | 1.355 | 1.120 | 0.965 | 1.038 | 1.007 | 1.091 | 1.050 | 0.713 | 0.622 |
| 1:243 | 1.171 | 1.380 | 1.237 | 1.214 | 1.215 | 1.069 | 1.154 | 1.172 | 0.862 | 0.766 |
| 1:729 | 1.307 | 1.388 | 1.362 | 1.229 | 1.231 | 1.253 | 1.242 | 1.264 | 0.826 | 0.725 |
| 0 | 1.030 | 1.171 | 1.187 | 1.100 | 1.130 | 1.076 | 1.034 | 1.183 | 0.915 | 0.861 |
| Receptor | B7/2-His at 1 μg/ml | | | | | | | | | |
| Secondary antibody | HRP Conjugated Mouse Anti His Secondary Antibody | | | | | | | | | |

TABLE 13

The 8D2H2L2 and 8D2H3L3 antibodies compete with B7-1 in ELISA

| Antibody concentration (μg/ml) | Coating: B7/1-hFc at 0.3 μg/ml | | | | | | | |
|---|---|---|---|---|---|---|---|---|
| | 8D2 H2L2 | | 8D2 H3L3 | | 10D1 | | 11.2.1 | |
| 5 | 0.207 | 0.232 | 0.187 | 0.202 | 0.166 | 0.172 | 0.080 | 0.089 |
| 1:3 | 0.346 | 0.267 | 0.286 | 0.327 | 0.210 | 0.194 | 0.090 | 0.097 |
| 1:9 | 0.625 | 0.702 | 0.416 | 0.388 | 0.486 | 0.548 | 0.160 | 0.138 |
| 1:27 | 0.577 | 0.727 | 0.590 | 0.503 | 0.673 | 0.621 | 0.488 | 0.369 |
| 1:81 | 0.830 | 0.743 | 0.747 | 0.617 | 0.663 | 0.647 | 0.698 | 0.660 |
| 1:243 | 0.707 | 0.760 | 0.673 | 0.768 | 0.652 | 0.775 | 0.755 | 0.900 |
| 1:729 | 0.780 | 0.882 | 0.840 | 0.842 | 0.705 | 0.691 | 0.909 | 0.793 |
| 0 | 0.577 | 0.752 | 0.632 | 0.745 | 0.732 | 0.909 | 0.683 | 0.735 |
| Antigen | CTLA4-mFc at 0.3 μg/ml | | | | | | | |
| Secondary antibody | HRP Conjugated Goat Anti Mouse IgG Secondary Antibody | | | | | | | |

TABLE 14

The 8D2H2L2 and 8D2H3L3 antibodies compete with B7-2 for binding to CTLA4 in ELISA

| Antibody concentration (μg/ml) | Antigen Coating: CTLA4-mFc at 0.5 μg/ml | | | | | | | |
|---|---|---|---|---|---|---|---|---|
| | 8D2 H2L2 | | 8D2 H3L3 | | 10D1 | | 11.2.1 | |
| 1.5 | 0.377 | 0.376 | 0.417 | 0.432 | 0.449 | 0.408 | 0.372 | 0.494 |
| 1:3 | 0.616 | 0.537 | 0.540 | 0.511 | 0.553 | 0.602 | 0.437 | 0.348 |
| 1:9 | 0.988 | 0.927 | 0.548 | 0.614 | 0.806 | 0.788 | 0.479 | 0.412 |
| 1:27 | 1.085 | 1.038 | 0.717 | 0.728 | 0.969 | 0.890 | 0.622 | 0.529 |
| 1:81 | 1.227 | 1.059 | 1.010 | 0.951 | 0.974 | 0.916 | 0.805 | 0.649 |
| 1:243 | 1.136 | 1.066 | 1.255 | 1.160 | 0.935 | 0.921 | 0.930 | 0.754 |
| 1:729 | 1.218 | 1.158 | 1.239 | 1.162 | 1.108 | 1.045 | 0.981 | 0.746 |
| 0 | 1.094 | 1.068 | 1.198 | 1.214 | 1.082 | 1.047 | 0.987 | 0.819 |
| Ligand | B7/2-His at 1 μg/ml | | | | | | | |
| Secondary antibody | HRP Conjugated Mouse Anti His Secondary Antibody | | | | | | | |

TABLE 15

The 8D2H2L15 and 8D2H2L17 antibodies compete with B7-1 for binding to CTLA4 in ELISA Antigen coating: B7/1-hFc at 0.5 µg/ml

| Dilution of Antibody | 8D2 H2L2 (20150327) | | 8D2 H2L15 | | 8D2 H2L17 | | 10D1 | | 11.2.1 | | 8D2 H2L2 (20140422) | |
|---|---|---|---|---|---|---|---|---|---|---|---|---|
| 5 µg/ml | 0.09 | 0.10 | 0.07 | 0.07 | 0.06 | 0.07 | 0.08 | 0.11 | 0.06 | 0.06 | 0.12 | 0.14 |
| 1:3 | 0.13 | 0.14 | 0.07 | 0.07 | 0.06 | 0.07 | 0.33 | 0.24 | 0.09 | 0.08 | 0.26 | 0.24 |
| 1:9 | 0.29 | 0.26 | 0.07 | 0.09 | 0.08 | 0.08 | 0.71 | 0.78 | 0.33 | 0.30 | 0.45 | 0.49 |
| 1:27 | 0.66 | 0.58 | 0.70 | 1.03 | 0.89 | 0.93 | 1.11 | 1.17 | 1.14 | 1.19 | 1.06 | 1.10 |
| 1:81 | 0.69 | 0.62 | 0.68 | 1.18 | 0.97 | 0.79 | 1.16 | 1.35 | 1.17 | 1.20 | 1.09 | 1.09 |
| 1:243 | 0.66 | 0.64 | 0.75 | 1.13 | 1.05 | 0.99 | 1.27 | 1.48 | 1.30 | 1.31 | 1.19 | 0.99 |
| 1:729 | 0.69 | 0.64 | 0.74 | 1.07 | 1.25 | 1.35 | 1.33 | 1.56 | 1.32 | 1.31 | 1.16 | 1.12 |
| 0 | 0.59 | 0.66 | 0.53 | 1.09 | 1.18 | 1.18 | 1.33 | 1.29 | 1.28 | 1.30 | 1.11 | 1.04 |
| Ligand | CTLA4-mFc at 0.3 µg/ml | | | | | | | | | | | |
| Secondary antibody | HRP Conjugated Mouse Anti His Secondary Antibody | | | | | | | | | | | |

TABLE 16

The 8D2H2L15 and 8D2H2L17 antibodies compete with B7-2 for binding to CTLA4 in ELISA CTLA4-mFc at 2 µg/ml

| Dilution of Antibody | 8D2H2L2 20140422 | | 8D2H2L15 | | 8D2H2L17 | | 10D1 | | 11.2.1 | | 8D2H2L2 20150327 | |
|---|---|---|---|---|---|---|---|---|---|---|---|---|
| 1 µg/ml | 0.05 | 0.05 | 0.05 | 0.05 | 0.05 | 0.05 | 0.05 | 0.05 | 0.04 | 0.04 | 0.05 | 0.05 |
| 1:3 | 0.05 | 0.05 | 0.05 | 0.05 | 0.05 | 0.05 | 0.07 | 0.07 | 0.05 | 0.05 | 0.47 | 0.37 |
| 1:9 | 0.15 | 0.16 | 0.17 | 0.19 | 0.06 | 0.12 | 0.44 | 0.35 | 0.17 | 0.16 | 0.65 | 0.58 |
| 1:27 | 0.55 | 0.59 | 0.42 | 0.48 | 0.50 | 0.57 | 0.73 | 0.70 | 0.57 | 0.57 | 0.79 | 0.70 |
| 1:81 | 0.76 | 0.84 | 0.75 | 0.75 | 0.77 | 0.81 | 0.85 | 0.86 | 0.84 | 0.76 | 0.86 | 0.77 |
| 1:243 | 0.84 | 0.79 | 0.83 | 0.84 | 0.82 | 0.87 | 0.86 | 0.89 | 0.84 | 0.85 | 0.83 | 0.84 |
| 1:729 | 0.77 | 0.76 | 0.94 | 1.00 | 0.97 | 0.98 | 0.99 | 0.91 | 0.87 | 0.85 | 0.82 | 0.80 |
| 0 | 0.77 | 0.78 | 0.92 | 0.97 | 0.81 | 0.82 | 0.76 | 0.96 | 0.91 | 0.80 | 0.80 | 0.76 |
| Ligand | B7/2-His, 0.5 µg/ml | | | | | | | | | | | |
| Secondary antibody | HRP Conjugated Mouse Anti His Secondary Antibody (1:4000) | | | | | | | | | | | |

TABLE 17

The binding efficiency, $EC_{50}$, of 8D2, 8D2(Re) and the 8D2 humanized antibodies 8D2H1L1, 8D2H2L2, 8D2H3L3, 8D2H2L15, and 8D2H2L17 to the CTLA4 antigen in competition with B7 obtained by curve simulation in the analysis by competitive ELISA

| | Antibody $EC_{50}$ (nM) | | 10D1 $EC_{50}$ (nM) | | 11.2.1 $EC_{50}$ (nM) | |
|---|---|---|---|---|---|---|
| | B7-1 | B7-2 | B7-1 | B7-2 | B7-1 | B7-2 |
| 8D2 | 0.44 | 0.208 | — | 0.464 | — | 0.15 |
| 8D2(Re) | 0.514 | 0.153 | — | 0.464 | — | 0.15 |
| 8D2H1L1 | 2.478 | 0.178 | 1.91 | 0.464 | 1.691 | 0.15 |
| 8D2H2L2 | 5.932 | 1.643 | 5.15 | 2.056 | 1.073 | 0.172 |
| 8D2H2L2 | 2.973 | 0.368 | — | — | — | — |
| 8D2H2L2 | 3.118 | 0.301 | — | — | — | — |
| 8D2H3L3 | 2.144 | 0.167 | 5.15 | 2.056 | 1.073 | 0.172 |
| 8D2H2L15 | 1.973 | 0.227 | 4.586 | 0.629 | 2.606 | 0.349 |
| 8D2H2L17 | 1.787 | 0.296 | 4.586 | 0.629 | 2.606 | 0.349 |

Note:
8D2H2L2 was tested in triplicate.

The above results demonstrated that the antibodies 8D2, 8D2 (Re) and the 8D2 humanized antibodies 8D2H1L1, 8D2H2L2, 8D2H3L3, 8D2H2L15, and 8D2H2L17 all can compete with B7 for binding to the CTLA4 antigen. Particularly, 8D2, 8D2(Re), 8D2H1L1, and 8D2H2L2 are stronger than 10D1 in competing with B7-2 for binding to CTLA4, while 8D2H2L17 is stronger than the antibodies 10D1 and 11.2.1 in competing with both of B7-1 and B7-2 for binding to CTLA4.

Example 9. Analysis of the Biological Activities of the Monoclonal Antibody 8D2 and the Humanized Antibodies 8D2H1L1, 8D2H2L2, 8D2H3L3, 8D2H2L5, and 8D2H2L17 in Cells To detect the effect of the monoclonal antibody 8D2 and the humanized antibodies 8D2H1L1, 8D2H2L2, 8D2H3L3, 8D2H2L15, and 8D2H2L17, and the control antibodies 10D1 and 11.2.1 on the IL-2 expression of peripheral blood mononuclear cells (PBMC's), peripheral blood from healthy donors was collected into collection tubes containing heparin sodium. PBMC's were obtained as a cell suspension after dilution in PBS and centrifugation on separation medium (at 2550 rpm for 20 min). The cell suspension was added with SEB (1 µg/mL)/PHA (30 µl/ml) and placed in an incubator at 37° C. with saturated humidity containing 5% $CO_2$ for further culture. Raji lymphocytes and the antibody were added. After co-incubation for 48 hours, PBMC's were washed with PBS twice, and were add to 96 well plates at 10,000 cell/well. Then, the corresponding concentration gradient of the antibodies was added. After inoculation for 20 minutes, Raji cells treated with MMC for 1 hour were added at 10,000 cell/well for co-culture of 72 hours. After co-culture for 72 hours, the cell culture was collected for supernatant and the IL-2 expression profile in the supernatant of the cell co-culture was detected using an ELISA kit following the instructions provided with the kit (Dakewe Co., DKW12-1020-096).

Figure 26:
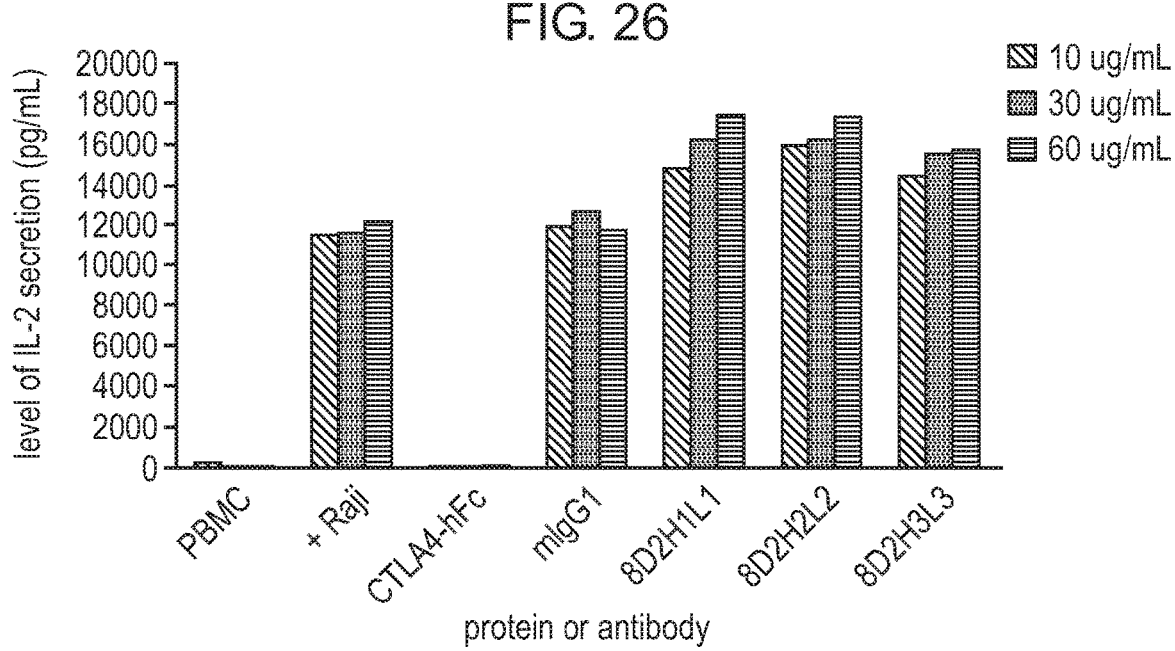
FIG. 26. Effects on the level of IL-2 secretion by the T lymphocytes as detected by the ELISA method after co-culture of 72 hours with peripheral blood mononuclear cells (PBMC), Raji cells and the humanized antibodies 8D2H1L1, 8D2H2L2, or 8D2H3L3, respectively. The results show that the humanized antibodies of the mAb 8D2 increased the IL-2 secretion by the T lymphocytes by preventing the receptor of CTLA4.
Figure 27:
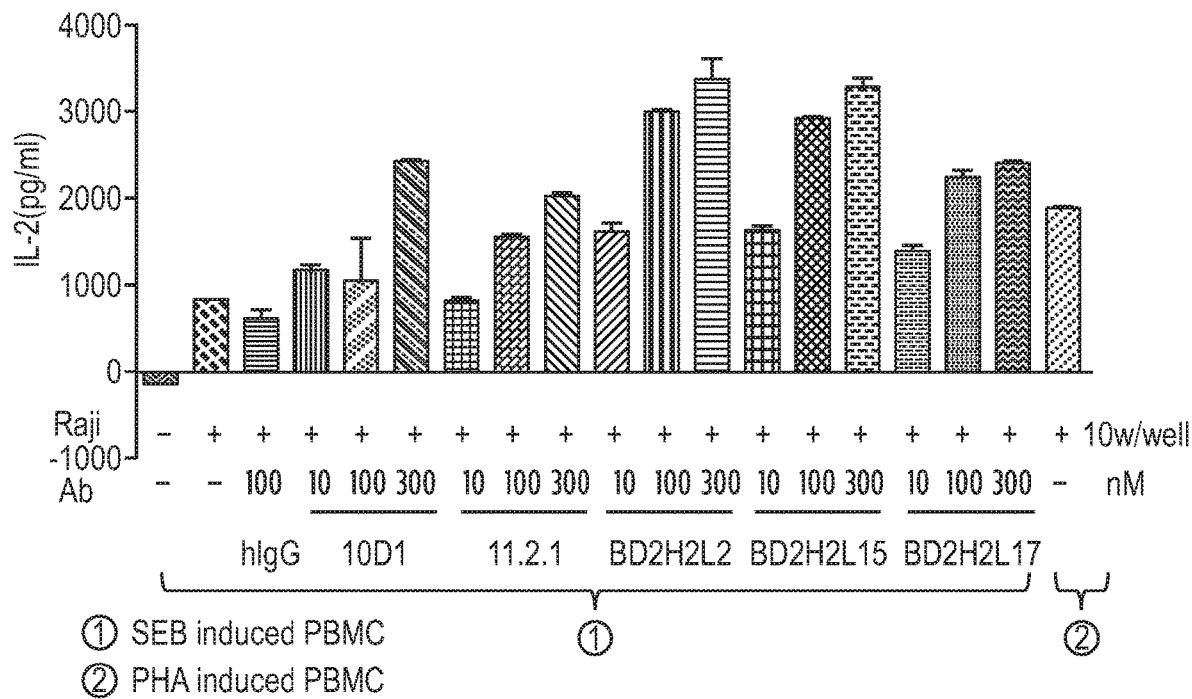
FIG. 27. Effects on the level of IL-2 secretion by the T lymphocytes as detected by the ELISA method after co-culture of 72 hours with peripheral blood mononuclear cells (PBMC), Raji cells and the humanized antibodies 8D2H2L2, 8D2H2L15, or 8D2H2L17 and control antibodies 10D1 and 11.2.1, respectively. The results show that the humanized antibodies of the mAb 8D2 increased the IL-2 secretion by the T lymphocytes by preventing the receptor of CTLA4.

After statistical analysis, the results of the experiments are showed in FIGS. 26 and 27. As compared with the T cell group and the Raji cell group, for the monoclonal antibody 8D2, all its humanized antibodies 8D2H1L1, 8D2H2L2, 8D2H3L3, 8D2H2L15, and 8D2H2L17 can effectively block binding of CTLA4 to B7 and improve the IL-2 expression in T lymphocytes (FIGS. 26 and 27). Particularly, the inventor surprisingly discovered that 8D2H2L2, 8D2H2L15 and 8D2H2L17 are significantly superior than the control antibodies 10D1 and 11.2.1. At the concentration of 10 nM, they achieved an IL-2 level comparable or even better than that achieved by 10D1 or 11.2.1 at the concentration of 100 nM. Thus, the antibodies of the present invention can increase the level of IL-2 at a lower concentration, e.g., about 10 nM.

Example 10. The In Vivo Anti-Tumor Activity of the Monoclonal Antibody 8D2H2L2

The in vivo anti-tumor activity of 8D2H2L2 was evaluated using the hu-SCID-raji animal model. Human peripheral blood mononuclear cells (PBMC's) were isolated using the Ficoll reagent, and activated using SEB at 1 µg/ml for 3 days. Then, $1.25 \times 10^6$ activated PBMC's were mixed with $5 \times 10^6$ raji Burkitt lymphoma cells and 8D2H2L2 (20 mg/kg), and were injected subcutaneously on the back of SCID-beige mice. At the same time, an isotype control group was set up, 5 animals per group. Subsequently, a dose of 20 mg/kg was administered by intravenous injection once a week for three consecutive weeks. The tumor volume was measured twice a week until the end of the experiments or when the tumor volume reached 1000 $mm^3$.

Figure 28:
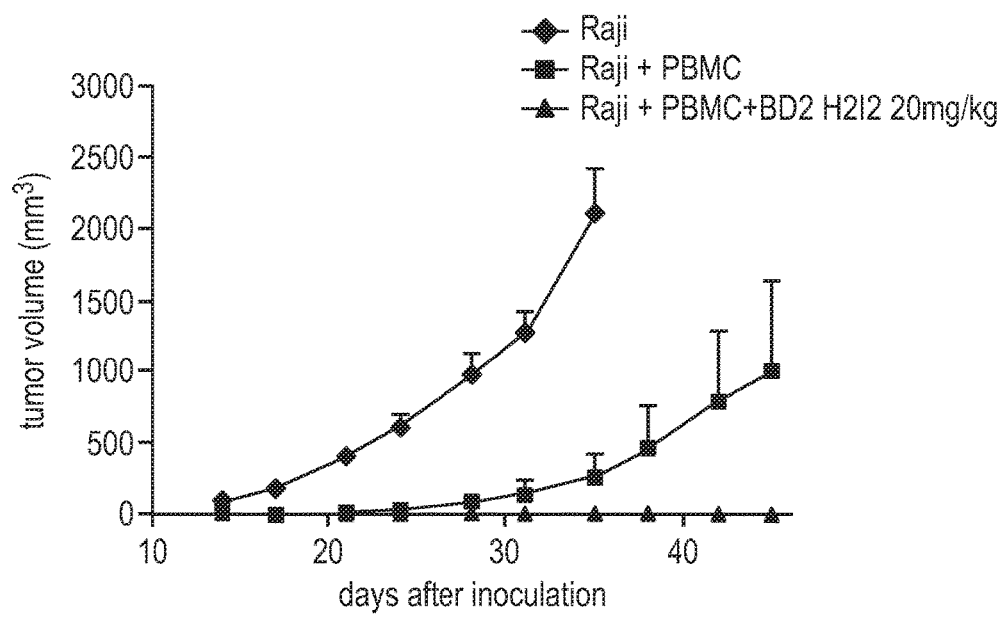
FIG. 28. The growth curve of the tumor subcutaneously transplanted in the hu-SCID-Raji model treated with 8D2H2L2.

As shown in FIG. 28, 8D2H2L2 could notably inhibit tumor growth in the hu-SCID-raji model. This result indicated that this antibody can be used clinically to treat lymphoma.

While the specific embodiments of the invention have been described in details, those skilled in the art, in light of the teaching disclosed in the specification, will understand that various changes and modifications can be made to the details, all of which fall into the protection scope of the present invention. The full scope of the invention is set forth in the appended claims and any equivalents thereof.

The invention claimed is:

1. A monoclonal antibody or antigen binding fragment thereof, wherein the monoclonal antibody or antigen binding fragment thereof binds to human CTLA4 and comprises a heavy chain variable region and a light chain variable region,
wherein the heavy chain variable region comprises:
  a. an HCDR1 comprising the amino acid sequence of SEQ ID NO: 27,
  b. an HCDR2 comprising the amino acid sequence of SEQ ID NO: 28, and
  c. an HCDR3 comprising the amino acid sequence of SEQ ID NO: 29;
and the light chain variable region comprises:
  d. an LCDR1 comprising the amino acid sequence of SEQ ID NO: 30,
  e. an LCDR2 comprising the amino acid sequence of SEQ ID NO: 31, and
  f. an LCDR3 comprising an amino acid sequence selected from SEQ ID NO: 32, SEQ ID NO: 33, and SEQ ID NO: 34, wherein the monoclonal antibody or antigen binding fragment thereof has an activity selected from the group consisting of: blocks the binding of human CTLA4 to human B7, down-regulates human CTLA4 activity, increases IL-2 expression by T-lymphocytes when administered to a host, and reduces immunosuppression in a subject when administered to the subject.

2. The monoclonal antibody or antigen binding fragment thereof according to claim 1, wherein
  the amino acid sequence of the heavy chain variable region (VH) of the monoclonal antibody is selected from the group consisting of: SEQ ID NO: 6, SEQ ID NO: 10, SEQ ID NO: 14, SEQ ID NO: 18, and any of SEQ ID NO: 6, SEQ ID: 10, and SEQ ID NO: 14, wherein the methionine at position 18 in SEQ ID NO: 6, SEQ ID NO: 10, and SEQ ID NO: 14 is substituted with an amino acid selected from the group consisting of: leucine, valine, isoleucine, and alanine; and
  the amino acid sequence of the light chain variable region (VL) of the monoclonal antibody is selected from the group consisting of: SEQ ID NO: 8, SEQ ID NO: 12, SEQ ID NO: 16, SEQ ID NO: 20, SEQ ID NO: 22, and SEQ ID NO: 24.

3. The monoclonal antibody or antigen binding fragment thereof according to claim 2, wherein the monoclonal antibody comprises:
  (1) the VH as set forth in SEQ ID NO: 6 and the VL as set forth in SEQ ID NO: 8;
  (2) the VH as set forth in SEQ ID NO: 10 and the VL as set forth in SEQ ID NO: 12;
  (3) the VH as set forth in SEQ ID NO: 14 and the VL as set forth in SEQ ID NO: 16;
  (4) the VH as set forth in SEQ ID NO: 18 and the VL as set forth in SEQ ID NO: 20;
  (5) the VH as set forth in SEQ ID NO: 14 and the VL as set forth in SEQ ID NO: 22; or
  (6) the VH as set forth in SEQ ID NO: 14 and the VL as set forth in SEQ ID NO: 24;
  (7) the VH as set forth in SEQ ID NO: 6, wherein the methionine at amino acid position 18 is substituted with leucine, valine, isoleucine, or alanine, and the VL as set forth in SEQ ID NO: 8;
  (8) the VH as set forth in SEQ ID NO: 10, wherein the methionine at amino acid position 18 is substituted with leucine, valine, isoleucine, or alanine, and the VL as set forth in SEQ ID NO: 12;
  (9) the VH as set forth in SEQ ID NO: 14, wherein the methionine at amino acid position 18 is substituted with leucine, valine, isoleucine, or alanine, and the VL as set forth in SEQ ID NO: 16;
  (10) the VH as set forth in SEQ ID NO: 14, wherein the methionine at amino acid position 18 is substituted with leucine, valine, isoleucine, or alanine, and the VL as set forth in SEQ ID NO: 22; and
  (11) the VH as set forth in SEQ ID NO: 14, wherein the methionine at amino acid position 18 is substituted with leucine, valine, isoleucine, or alanine, and the VL as set forth in SEQ ID NO: 24.

4. The monoclonal antibody or antigen binding fragment thereof of claim 3, wherein the methionine at amino acid position 18 of SEQ ID NO: 6, SEQ ID NO: 10, or SEQ ID NO: 14 is substituted with leucine.

5. The monoclonal antibody or antigen binding fragment thereof according to claim 1, wherein the monoclonal antibody or antigen binding fragment thereof is selected from the group consisting of: an Fab, an Fab', an F(ab')$_2$, an Fd, an Fv, a dAb, a complementarity determining region fragment, a single chain antibody, a humanized antibody, a chimeric antibody, and a diabody.

6. The monoclonal antibody or antigen binding fragment thereof according to claim 1, wherein the monoclonal antibody or antigen binding fragment thereof binds to the human CTLA4 protein with a K$_D$ less than about $10^{-5}$ M.

7. The monoclonal antibody or antigen binding fragment thereof according to claim 1, wherein the monoclonal antibody or antigen binding fragment thereof comprises non-CDR regions and the non-CDR regions are from a human.

8. A conjugate comprising the monoclonal antibody or antigen binding fragment thereof according to claim 1 and a conjugated moiety, wherein the conjugated moiety is a detectable label; specifically, the conjugated moiety is a radioisotope, a fluorescent substance, a luminescent substance, a chromogenic substance, or an enzyme.

9. An in vitro method of relieving CTLA4 immunosuppression comprising contacting cells with an effective amount of the monoclonal antibody or antigen binding fragment thereof according to claim 1 or the conjugate according to claim 8, where immunosuppression is measured by blocking binding of human CTLA4 to human B7 or by measuring an increase in IL-2 expression in T lymphocytes.

10. A method of diagnosing a tumor, comprising the step of administrating an effective amount of a monoclonal antibody or antigen binding fragment thereof to a sample of the tumor obtained from a patient and assessing whether the sample of the tumor binds to the monoclonal antibody or antigen binding fragment thereof, wherein the sample of the tumor is a biopsy of the patient, wherein the tumor is selected from the group consisting of: a melanoma, a kidney tumor, a prostate cancer, a bladder cancer, a colorectal cancer, a cancer of gastrointestinal tract, and a liver cancer, and wherein the monoclonal antibody or antigen binding fragment thereof comprises the complementary determining regions (CDR's) selected from the following:
  a. an HCDR1 comprising the amino acid sequence of SEQ ID NO: 27,
  b. an HCDR2 comprising the amino acid sequence of SEQ ID NO: 28, and
  c. an HCDR3 comprising the amino acid sequence of SEQ ID NO: 29;
  and/or
  d. an LCDR1 comprising the amino acid sequence of SEQ ID NO: 30,
  e. an LCDR2 comprising the amino acid sequence of SEQ ID NO: 31, and
  f. an LCDR3 comprising an amino acid sequence selected from SEQ ID NO: 32, SEQ ID NO: 33, and SEQ ID NO: 34, and wherein the monoclonal antibody or antigen binding fragment thereof is linked to a detectable compound.

11. An isolated nucleic acid molecule comprising a nucleic acid sequence that encodes a heavy chain variable region of an antibody, wherein the heavy chain variable region of the antibody comprises: CDRs with the amino acid sequences of SEQ ID NOs: 27-29.

12. An isolated nucleic acid molecule comprising a nucleic acid sequence that encodes a light chain variable region of an antibody, wherein the light chain variable region of the antibody comprises: CDRs with the amino acid sequences of SEQ ID NOs: 30-32.

13. A vector comprising the isolated nucleic acid molecule of claim 11 or claim 12.

14. A host cell comprising the vector of claim 13.

15. A host cell comprising the isolated nucleic acid molecule of claim 11.

16. The isolated nucleic acid molecule of claim 11, wherein the nucleic acid sequence encodes the heavy chain variable region of an antibody, and the heavy chain variable region of the antibody has the amino acid sequence as set forth in SEQ ID NO: 6, SEQ ID NO: 10, SEQ ID NO: 14, or SEQ ID NO: 18, wherein the methionine at position 18 in SEQ ID NO: 6, SEQ ID NO: 10, and SEQ ID NO: 14 is independently substituted with an amino acid selected from the group consisting of: leucine, valine, isoleucine, and alanine.

17. A host cell comprising the isolated nucleic acid molecule of claim 16.

18. A vector comprising the isolated nucleic acid molecule of claim 16.

19. A host cell comprising the vector of claim 18.

20. The isolated nucleic acid molecule of claim 11, wherein the nucleic acid sequence has the nucleotide sequence as set forth in SEQ ID NO: 5, SEQ ID NO: 9, SEQ ID NO: 13, or SEQ ID NO: 17.

21. A host cell comprising the isolated nucleic acid molecule of claim 20.

22. A vector comprising the isolated nucleic acid molecule of claim 20.

23. A host cell comprising the vector of claim 22.

24. The isolated nucleic acid molecule of claim 12, wherein the isolated nucleic acid molecule comprises a nucleic acid sequence capable of encoding a light chain variable region of an antibody, wherein the light chain variable region of the antibody has the amino acid sequence as set forth in SEQ ID NO: 8, SEQ ID NO: 12, SEQ ID NO: 16, SEQ ID NO: 20, SEQ ID NO: 22, or SEQ ID NO: 24.

25. A host cell comprising the isolated nucleic acid molecule of claim 24.

26. A vector comprising the isolated nucleic acid molecule of claim 24.

27. A host cell comprising the vector of claim 26.

28. The isolated nucleic acid molecule of claim 12, wherein the isolated nucleic acid molecule comprises the nucleotide sequence as set forth in SEQ ID NO: 7, SEQ ID NO: 11, SEQ ID NO: 15, SEQ ID NO: 19, SEQ ID NO: 21, or SEQ ID NO: 23.

29. A host cell comprising the isolated nucleic acid molecule of claim 28.

30. A vector comprising the isolated nucleic acid molecule of claim 28.

31. A host cell comprising the vector of claim 30.

32. A vector comprising the isolated nucleic acid molecule of claim 11.

33. A host cell comprising the vector of claim 32.

34. A host cell comprising an isolated nucleic acid molecule comprising a nucleic acid sequence that encodes:
  (i) a heavy chain variable region of an antibody, wherein the heavy chain variable region of the antibody comprises: CDRs with the amino acid sequences of SEQ ID NOs: 27-29; and
  (ii) a light chain variable region of an antibody, wherein the light chain variable region of the antibody comprises: CDRs with the amino acid sequences of SEQ ID NOs: 30-32.

35. A method of preparing the monoclonal antibody or antigen binding fragment thereof comprising culturing the host cell of claim 34 under suitable conditions, collecting a supernatant from the cell culture; and purifying the supernatant to recover the monoclonal antibody or antigen binding fragment thereof.

\* \* \* \* \*